United States Patent
Petrini et al.

(10) Patent No.: US 7,091,037 B1
(45) Date of Patent: Aug. 15, 2006

(54) DNA ENCODING A DNA REPAIR PROTEIN

(75) Inventors: John H. J. Petrini, Madison, WI (US); William Francis Morgan, Mill Valley, CA (US); Richard Scott Maser, Madison, WI (US); James Patrick Carney, El Cerrito, CA (US)

(73) Assignee: WARF Wisconsin Alumni Research Foundation, Madison, WI (US)

( * ) Notice: Subject to any disclaimer, the term of this patent is extended or adjusted under 35 U.S.C. 154(b) by 780 days.

(21) Appl. No.: 09/837,602

(22) Filed: Apr. 18, 2001

Related U.S. Application Data

(62) Division of application No. 09/067,641, filed on Apr. 27, 1998, now abandoned.

(51) Int. Cl.
C12N 15/63 (2006.01)
C12N 15/11 (2006.01)

(52) U.S. Cl. .................. 435/320.1; 435/69.1; 536/23.1

(58) Field of Classification Search ............... 536/23.1, 536/23.2, 23.4, 23.5; 530/350; 424/192.1
See application file for complete search history.

(56) References Cited

U.S. PATENT DOCUMENTS 5,965,427 A    10/1999    Dolganov et al. ........ 435/252.3

OTHER PUBLICATIONS

Burgess et al., J of Cell Bio. 111:2129-2138, 1990.*
Lazar et al. Molecular and Cellular Biology 8:1247-1252, 1988.*
(Bowie et al. Science, 247:1306-1310, 1990.*
Allemand, I., et al., "Transgenic and Knock-Out Models for Studying DNA Repair", *Biochimie*, 77, 826-832, (1995).
Baldwin, et al., *Monoclonal Antibodies for Cancer Detection and Therapy*, 20, (1985).
Brandon, E. P., et al., "Targeting the Mouse Genome: A Compendium of Knockouts (Part I)", *Current Biology*, 5, 625-634, (1995).
Brandon, E. P., et al., "Targeting the Mouse Genome: A Compendium of Knockouts (Part II)", *Current Biology*, 5, 758-765, (1995).
Choi, I. S., et al., "Expression of RAD4 gene of *Saccharomyces cerevisiae* that can be propagated in *Escherichia coli* without inactivation", *Biochemical and Biophysical Research Communications*, vol. 193 (1), 1991-197, (May 28, 1993).
de Vries, A., et al., "Xpa Knockout Mice", *Seminars in Cancer Biology*, 7 229-240, (1996).
Dolganov, G.M., et al., "Human Rad50 Is Physically Associated with Human Mre11: Identification of a Conserved Multiprotein Complex Implicated in Recombinational DNA Repair", *Molecular and Cellular Biology*, 16, 4832-4841, (Sep. 1996).
Majzoub, J.A., et al., "Knockout Mice", *The New England Journal of Medicine*, 334, 904-907, (Apr. 4, 1996).
Maser, R. S., et al., "hMre11 and hRad50 Nuclear Foci Are Induced during the Normal Cellular Response to DNA Double-Strand Breaks", *Molecular and Cellular Biology*, 17, 6087-6096, (Oct. 1997).
Petrini, J. H., et al., "Isolation and characterizatio of the human MRE11 homologue", *Genomics*, 29, 80-86, (1995).
Rosenberg, M. P., "Gene Knockout and Transgenic Technologies in Risk Assessment: The Nex Generation", *Molecular Carcinogenesis*, 20, 262-274, (1997).
Xiao, Y., et al., "Conditional gene Targeted deletion by Cre recombinase demonstrates the requirement for the double-strand break repair Mre11 protein in murine embryonic stem cells", *Nuclecid Acids Research*, vol. 25, 15, 2985-2991, (1997).
*NCBI* (AA577530), www.ncbi.nlm.nih.gov/entrez/query.fcgi?cmd=Retrieve&db=nucleotide&list_uids=. . . ,(1997),2.
*NCBI* (AA535711), www.ncbi.nlm.nih.gov/entrez/query.fcgi?cmd=Retrieve&db=nucleotide&list_uids=. . . , (1997),2.
Carney, J. P., et al., "The hMre11/hRad50 Protein Complex and Nijmegen Breakage Syndrome Linkage of Double-Strand Break Repair to the Cellular DNA Damage Response", *Cell*, 93, (May 1, 1998), 477-486.
Varon, R., et al. "Nibrin, a Novel DNA Double-Strand Break Repair Protein, Is Mutated in Nijmegen Breakage Syndrome", *Cell Press*, 93, (May 1, 1998), 467-476.

* cited by examiner

*Primary Examiner*—Misook Yu
(74) *Attorney, Agent, or Firm*—Schweggman, Lundberg, Woessner & Kluth P.A.

(57) ABSTRACT

An isolated and purified DNA molecule encoding a DNA repair protein, p95, is provided, as is isolated and purified p95. Also provided are methods of detecting p95 and DNA encoding p95. The invention further provides p95 knock-out mice.

11 Claims, 13 Drawing Sheets

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 12

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 13

```
ttcggcacgaggcgcggttgcacgtcggccccagccctgaggagccggaccgatgtggaaactgctgcccgccgcgggcc
cggcaggaggagaaccatacagacttttgactggcgttgagtacgttgttggaaggaaaaactgtgccattctaattgaa
aatgatcagtcgatcagccgaaatcatgctgtgttaactgctaacttttctgtaaccaacctgagtcaaacagatgaaat
ccctgtattgacattaaaagataattctaagtatggtacctttgttaatgaggaaaaaatgcagaatggcttttcccgaa
ctttgaagtcgggggatggtattacttttggagtgtttggaagtaaattcagaatagagtatgagcctttggttgcatgc
tcttcttgtttagatgtctctgggaaaactgctttaaatcaagctatattgcaacttggaggatttactgtaaacaattg
gacagaagaatgcactcaccttgtcatggtatcagtgaaagttaccattaaaacaatatgtgcactcatttgtggacgtc
caattgtaaagccagaatatttactgaattcctgaaagcagttcagtccaagaagcagcctccacaaattgaaagttt
tacccacctcttgatgaaccatctattggaagtaaaaatgttgatctgtcaggacggcaggaaagaaaacaaatcttcaa
agggaaaacatttatattttgaatgccaaacagcataagaaattgagttccgcagttgtctttggaggtggggaagcta
ggttgataacagaagagaatgaagaagaacataatttcttttggctccgggaacgtgtgttgttgatacaggaataaca
aactcacagaccttaattcctgactgtcagaagaaatggattcagtcaataatggatatgctccaaaggcaaggtcttag
acctattcctgaagcagaaattggattggcggtgattttcatgactacaaagaattactgtgatcctcagggccatccca
gtacaggattaaagacaacaactccaggaccaagcctttcacaaggcgtgtcagttgatgaaaaactaatgccaagcgcc
ccagtgaacactacaacatacgtagctgacacagaatcagagcaagcagatacatgggatttgagtgaaaggccaaaaga
aatcaaagtctccaaaatggaacaaaaattcagaatgctttcacaagacgcacccactgtaaaggagtcctgcaaaacaa
gctctaataataatagtatggtatcaaatactttggctaagatgagaatcccaaactatcagctttcaccaactaaattg
ccaagtataaataaaagtaaagataggcgcttctcagcagcagcagaccaactccatcagaaactactttcagccgtctac
caaaaaaagggaaagggatgaagaaaatcaagaaatgtcttcatgcaaatcagcaagaatagaaacgtcttgttctcttt
tagaacaaacacaacctgctacaccctcattgtggaaaaataaggagcagcatctatctgagaatgagcctgtggacaca
aactcagacaataacttatttacagatacagatttaaaatctattgtgaaaaattctgccagtaaatctcatgctgcaga
aaagctaagatcaaataaaaaagggaaatggatgatgtggccatagaagatgaagtattggaacagttattcaaggaca
caaaaccagagttagaaattgatgtgaaagttcaaaaacaggaggaagatgtcaatgttagaaaaaggccaaggatggat
atagaaacaaatgacactttcagtgatgaagcagtaccagaaagtagcaaaatatctcaagaaaatgaaattgggaagaa
acgtgaactcaaggaagactcactatggtcagctaaagaaatatctaacaatgacaaacttcaggatgatagtgagatgc
ttccaaaaaagctgttattgactgaatttagatcactggtgattaaaaactctacttccagaaatccgtctggcataaat
gatgattatggtcaactaaaaaatttcaagaaattcaaaaaggtcacatatcctggagcaggaaaacttccacacatcat
tggaggatcagatctaatagctcatcatgctcgaaagaatacagaactagaagagtggctaaggcaggaaatggaggtac
aaaatcaacatgcaaaagaagagtctcttgctgatgatcttttagatacaatccttatttaaaaaggagaagataactg
aggattttaaaaagaagccatggaaaaacttcctagtaagcatctacttcaggccaacaaggttatatgaatatatagtg
tatagaagcgatttaagttacaatgttttatggcctaaatttattaaataaaatgcacaaaactttgattcttttgtatg
taacaattgtttgtyctgttttccaggctttgtcattgcatctttttttcattttttaaatgtgttttgtttattaaatagt
taatatagtcacagttcaaaattctaaatrtacgtaaggtaaaggactaaagtcacccttccaccattgtcctagctact
tggttccctcagaaaaaaattcatggatactcatttcttatgratcttttccagggatttttgagtcctattcaaattcc
tattttttaaataatttcctacacaaatgatagcataacatatgcagtgttctacaccttgcttttttacttagtaagatt
aaaaattataggaatatcaatataatgttttaatatttttcttttccattatgctgtagtcttacctaaactctggtg
atccaaacaaatggcttcagtggtgcagatgtcacctacatgttattctagtactagaaactgaagaccatgtggagac
ttcatcaaacatgggtttagttttcaccagaatggaaagacctgtacccttttggtggtcttactgagctgggtgggt
gtctgttttgagcttatttagagtcctagttttcctacttataaagtagaaatggtgagattgttttctttttctacckt
aaagggagatggtaagaaacaatgaatgtcttttttcaaacttttattgacaagtgattttcaagtctgtgttcaaaaata
tattcatgtacctgtgatccagcaagaagggagttccagtcaagagtcactacaactgattagttgtttagagaatgaga
aatggaacagtgaggaatggaggccatatttccatgacttcccttgtaaacagaagcaacagaagggacaagaggctggc
ctctacatcactctcaccttccaaatcttgtggaagtgcatctacttgccagaaccaaattaacttacttccaagttctg
gctgcttgcaggtggaactccagctgcagggagttagggaaatgaaggtcttttttaaaagcttctcagccttcctag
ggaacagaaattgggtgagccaatctgcaatttctactacaggcattgagaccagttagattattgaaatattatagaga
gttatgaacacttaaattatgatagtggtatgacattggatagaacatgggatactttagaagtagaattgacagggcat
attagttgatgaaatggagtcatttgagtctcttaatagccatgtatcataattaccaagtgaagctggtggaacatatg
gtctccatttttacagttaaggaatataatggacagattaatattgttytctgtcatgcccacaatccctttctaaggaag
actgccctactatagcagttttttatatttgtcaattatgaatataatgaatgaggagttctggtacctcctgtctttac
aaatattgggtgttgtccagtattttccctttttaaccmttcccaattcgggtgtgtaggtggatgtttccatttgggt
tttaatttgtatatccctgatagctataattgggtcatagaaattctttatacattctagatgcaagtctcttgycggat
atacgtattgagatattacacctagtctgtggcttgactgttttctttatgtcttttgatgaataaagttttaaattt
gacaaggtcaaattttattttttctttttgtttgatattttttctctccaatttaacccaagatttcagatattctgctc
tattatataaacttttatattttatattttgtgatctaccttgaattgatatgtatgttgtgaattatggatcagggttct
tttttccccatacaagtatccagtcattgtaacactgtttattgaaagaattatcctttcctcattaaattaccttgc
caattagtaaaaaatcaattaaccatrmarmmmmrrrggatccactagttctagagcggccgccaccgcggtggagctcca
gct
```

FIG. 14

MWKLLPAAGPAGGEPYRLLTGVEYVVGRKNCAILIENDQSISRNHAVLTANFSVTNLSQTDEIPVLTLKDNSKYGTFVNE
EKMQNGFSRTLKSGDGITFGVFGSKFRIEYEPLVACSSCLDVSGKTALNQAILQLGGFTVNNWTEECTHLVMVSVKVTIK
TICALICGRPIVKPEYFTEFLKAVQSKKQPPQIESFYPPLDEPSIGSKNVDLSGRQERKQIFKGKTFIFLNAKQHKKLSS
AVVFGGGEARLITEENEEEHNFFLAPGTCVVDTGITNSQTLIPDCQKKWIQSIMDMLQRQGLRPIPEAEIGLAVIFMTTK
NYCDPQGHPSTGLKTTTPGPSLSQGVSVDEKLMPSAPVNTTTYVADTESEQADTWDLSERPKEIKVSKMEQKFRMLSQDA
PTVKESCKTSSNNNSMVSNTLAKMRIPNYQLSPTKLPSINKSKDRASQQQQTNSIRNYFQPSTKKRERDEENQEMSSCKS
ARIETSCSLLEQTQPATPSLWKNKEQHLSENEPVDTNSDNNLFTDTDLKSIVKNSASKSHAAEKLRSNKKREMDDVAIED
EVLEQLFKDTKPELEIDVKVQKQEEDVNVRKRPRMDIETNDTFSDEAVPESSKISQENEIGKKRELKEDSLWSAKEISNN
DKLQDDSEMLPKKLLLTEFRSLVIKNSTSRNPSGINDDYGQLKNFKKFKKVTYPGAGKLPHIIGGSDLIAHHARKNTELE
EWLRQEMEVQNQHAKEESLADDLFRYNPYLKRRR.

FIG. 15

SEQUENCE LISTING

```
<160> NUMBER OF SEQ ID NOS: 24

<210> SEQ ID NO 1
<211> LENGTH: 4403
<212> TYPE: DNA
<213> ORGANISM: Homo sapiens

<400> SEQUENCE: 1
ttcggcacga ggcgcggttg cacgtcggcc ccagccctga ggagccggac cgatgtggaa      60
```

| | |
|---|---|
| actgctgccc gccgcgggcc cggcaggagg agaaccatac agacttttga ctggcgttga | 120 |
| gtacgttgtt ggaaggaaaa actgtgccat tctaattgaa aatgatcagt cgatcagccg | 180 |
| aaatcatgct gtgttaactg ctaactttc tgtaaccaac ctgagtcaaa cagatgaaat | 240 |
| ccctgtattg acattaaaag ataattctaa gtatggtacc tttgttaatg aggaaaaaat | 300 |
| gcagaatggc ttttcccgaa cttttgaagtc gggggatggt attacttttg gagtgtttgg | 360 |
| aagtaaattc agaatagagt atgagccttt ggttgcatgc tcttcttgtt tagatgtctc | 420 |
| tgggaaaact gctttaaatc aagctatatt gcaacttgga ggatttactg taaacaattg | 480 |
| gacagaagaa tgcactcacc ttgtcatggt atcagtgaaa gttaccatta aaacaatatg | 540 |
| tgcactcatt tgtggacgtc caattgtaaa gccagaatat tttactgaat tcctgaaagc | 600 |
| agttcagtcc aagaagcagc ctccacaaat tgaaagtttt tacccacctc ttgatgaacc | 660 |
| atctattgga agtaaaaatg ttgatctgtc aggacggcag gaaagaaaac aaatcttcaa | 720 |
| agggaaaaca tttatatttt tgaatgccaa acagcataag aaattgagtt ccgcagttgt | 780 |
| ctttggaggt ggggaagcta ggttgataac agaagagaat gaagaagaac ataatttctt | 840 |
| tttggctccg ggaacgtgtg ttgttgatac aggaataaca aactcacaga ccttaattcc | 900 |
| tgactgtcag aagaaatgga ttcagtcaat aatggatatg ctccaaaggc aaggtcttag | 960 |
| acctattcct gaagcagaaa ttggattggc ggtgattttc atgactacaa agaattactg | 1020 |
| tgatcctcag ggccatccca gtacaggatt aaagacaaca actccaggac caagcctttc | 1080 |
| acaaggcgtg tcagttgatg aaaaactaat gccaagcgcc ccagtgaaca ctacaacata | 1140 |
| cgtagctgac acagaatcag agcaagcaga tacatgggat ttgagtgaaa ggccaaaaga | 1200 |
| aatcaaagtc tccaaaatgg aacaaaaatt cagaatgctt tcacaagacg cacccactgt | 1260 |
| aaaggagtcc tgcaaaacaa gctctaataa taatagtatg gtatcaaata ctttggctaa | 1320 |
| gatgagaatc ccaaactatc agctttcacc aactaaattg ccaagtataa ataaaagtaa | 1380 |
| agatagggct tctcagcagc agcagaccaa ctccatcaga aactactttc agccgtctac | 1440 |
| caaaaaaagg gaaagggatg aagaaaatca agaaatgtct tcatgcaaat cagcaagaat | 1500 |
| agaaacgtct tgttctcttt tagaacaaac acaacctgct acaccctcat tgtggaaaaa | 1560 |
| taaggagcag catctatctg agaatgagcc tgtggacaca aactcagaca ataacttatt | 1620 |
| tacagataca gatttaaaat ctattgtgaa aaattctgcc agtaaatctc atgctgcaga | 1680 |
| aaagctaaga tcaaataaaa aaagggaaat ggatgatgtg gccatagaag atgaagtatt | 1740 |
| ggaacagtta ttcaaggaca caaaaccaga gttagaaatt gatgtgaaag ttcaaaaaca | 1800 |
| ggaggaagat gtcaatgtta gaaaaaggcc aaggatggat atagaaacaa atgcactttt | 1860 |
| cagtgatgaa gcagtaccag aaagtagcaa aatatctcaa gaaaatgaaa ttgggaagaa | 1920 |
| acgtgaactc aaggaagact cactatggtc agctaaagaa atatctaaca atgacaaact | 1980 |
| tcaggatgat agtgagatgc ttccaaaaaa gctgttattg actgaattta gatcactggt | 2040 |
| gattaaaaac tctacttcca gaaatccgtc tggcataaat gatgattatg gtcaactaaa | 2100 |
| aaatttcaag aaattcaaaa aggtcacata tcctggagca ggaaaacttc cacacatcat | 2160 |
| tggaggatca gatctaatag ctcatcatgc tcgaaagaat acagaactag aagagtggct | 2220 |
| aaggcaggaa atgagggtac aaaatcaaca tgcaaagaa gagtctcttg ctgatgatct | 2280 |
| ttttagatac aatccttatt taaaaaggag aagataactg aggattttaa aaagaagcca | 2340 |
| tggaaaaact tccagtaag catctacttc aggccaacaa ggttatatga atatatagtg | 2400 |
| tatagaagcg atttaagtta caatgttta tggcctaaat ttattaaata aaatgcacaa | 2460 |

-continued

```
aactttgatt cttttgtatg taacaattgt ttgtyctgtt ttcaggcttt gtcattgcat    2520 cttttttttca ttttaaatg tgttttgttt attaaatagt taatatagtc acagttcaaa    2580
attctaaatr tacgtaaggt aaaggactaa agtcacccctt ccaccattgt cctagctact   2640
tatttttaaa taatttccta cacaaatgat agcataacat atgcagtgtt ctacaccttg    2700
cttttttact tagtaagatt aaaaattata ggaatatcaa tataatgttt ttaatatttt    2760
ttcttttcca ttatgctgta gtcttaccta aactctggtg atccaaacaa aatggcttca    2820
gtggtgcaga tgtcacctac atgttattct agtactagaa actgaagacc atgtggagac    2880
ttcatcaaac atgggtttag ttttcaccag aatggaaaga cctgtacccc tttttggtgg    2940
tcttactgag ctgggtgggt gtctgttttg agcttattta gagtcctagt tttcctactt    3000
ataaagtaga aatggtgaga ttgttttctt tttctacckt aaagggagat ggtaagaaac    3060
aatgaatgtc ttttttcaaa ctttattgac aagtgatttt caagtctgtg ttcaaaaata    3120
tattcatgta cctgtgatcc agcaagaagg gagttccagt caagagtcac tacaactgat    3180
tagttgttta gagaatgaga atgaacag tgaggaatgg aggccatatt tccatgactt      3240
cccttgtaaa cagaagcaac agaagggaca agaggctggc ctctacatca ctctcacctt    3300
ccaaatcttg tggaagtgca tctacttgcc agaaccaaat taacttactt ccaagttctg    3360
gctgcttgca ggtggaactc cagctgcaag ggagttaggg aaatgaaggt cttttttttaa   3420 aagcttctca gccttcctag ggaacagaaa ttgggtgagc caatctgcaa tttctactac    3480
aggcattgag accagttaga ttattgaaat attatagaga gttatgaaca cttaaattat    3540
gatagtggta tgacattgga tagaacatgg gatactttag aagtagaatt gacagggcat    3600
attagttgat gaaatggagt catttgagtc tyttaatagc catgtatcat aattaccaag    3660
tgaagctggt ggaacatatg gtctccattt tacagttaag gaatataatg gacagattaa    3720
tattgttytc tgtcatgccc acaatccctt tctaaggaag actgccctac tatagcagtt    3780
tttatatttg tcaatttatg aatataatga atgaggagtt ctggtaccte ctgtctttac    3840 aaatattggg tgttgtccag tattttttccc tttttaaccm ttcccaattc gggtgtgtag    3900
gtggatgttt ccatttgggt tttaatttgt atatccctga tagctataat tgggtcatag    3960 aaattctttta tacattctag atgcaagtct cttgycggat atacgtattg agatattaca    4020
cctagtctgt ggcttgactg ttttctttat gtcttttgat gaatagaagt tttaaatttt    4080
gacaaggtca aattttattt tttctttttgt ttgatatttt ttctctccaa tttaacccca    4140
agatttcaga tattctgctc tattatataa actttatatt tttatattttg tgatctacct    4200 tgaattgata tgtatgttgt gaattatgga tcagggttct tttttttcccc catacaagta   4260 tccagtcatt gtaacactgt ttattgaaag aattatcctt tcctcattaa attaccttgc    4320
caattagtaa aaaatcaatt aaccatrmar mmmrrrggat ccactagttc tagagcggcc    4380
gccaccgcgg tggagctcca gct                                            4403
```

<210> SEQ ID NO 2
<211> LENGTH: 754
<212> TYPE: PRT
<213> ORGANISM: Homo sapiens

<400> SEQUENCE: 2

```
Met Trp Lys Leu Leu Pro Ala Ala Gly Pro Ala Gly Gly Glu Pro Tyr
 1               5                   10                  15

Arg Leu Leu Thr Gly Val Glu Tyr Val Val Gly Arg Lys Asn Cys Ala
```

```
                    20              25              30
Ile Leu Ile Glu Asn Asp Gln Ser Ile Ser Arg Asn His Ala Val Leu
            35              40                  45
Thr Ala Asn Phe Ser Val Thr Asn Leu Ser Gln Thr Asp Glu Ile Pro
50                      55                  60
Val Leu Thr Leu Lys Asp Asn Ser Lys Tyr Gly Thr Phe Val Asn Glu
65                  70                  75                  80
Glu Lys Met Gln Asn Gly Phe Ser Arg Thr Leu Lys Ser Gly Asp Gly
                85                  90                  95
Ile Thr Phe Gly Val Phe Gly Ser Lys Phe Arg Ile Glu Tyr Glu Pro
            100                 105                 110
Leu Val Ala Cys Ser Ser Cys Leu Asp Val Ser Gly Lys Thr Ala Leu
            115                 120                 125
Asn Gln Ala Ile Leu Gln Leu Gly Gly Phe Thr Val Asn Asn Trp Thr
            130                 135                 140
Glu Glu Cys Thr His Leu Val Met Val Ser Val Lys Val Thr Ile Lys
145                 150                 155                 160
Thr Ile Cys Ala Leu Ile Cys Gly Arg Pro Ile Val Lys Pro Glu Tyr
                165                 170                 175
Phe Thr Glu Phe Leu Lys Ala Val Gln Ser Lys Lys Gln Pro Pro Gln
            180                 185                 190
Ile Glu Ser Phe Tyr Pro Pro Leu Asp Glu Pro Ser Ile Gly Ser Lys
            195                 200                 205
Asn Val Asp Leu Ser Gly Arg Gln Glu Arg Lys Gln Ile Phe Lys Gly
210                 215                 220
Lys Thr Phe Ile Phe Leu Asn Ala Lys Gln His Lys Lys Leu Ser Ser
225                 230                 235                 240
Ala Val Val Phe Gly Gly Gly Glu Ala Arg Leu Ile Thr Glu Glu Asn
                245                 250                 255
Glu Glu Glu His Asn Phe Phe Leu Ala Pro Gly Thr Cys Val Val Asp
            260                 265                 270
Thr Gly Ile Thr Asn Ser Gln Thr Leu Ile Pro Asp Cys Gln Lys Lys
            275                 280                 285
Trp Ile Gln Ser Ile Met Asp Met Leu Gln Arg Gln Gly Leu Arg Pro
            290                 295                 300
Ile Pro Glu Ala Glu Ile Gly Leu Ala Val Ile Phe Met Thr Thr Lys
305                 310                 315                 320
Asn Tyr Cys Asp Pro Gln Gly His Pro Ser Thr Gly Leu Lys Thr Thr
                325                 330                 335
Thr Pro Gly Pro Ser Leu Ser Gln Gly Val Ser Val Asp Glu Lys Leu
            340                 345                 350
Met Pro Ser Ala Pro Val Asn Thr Thr Thr Tyr Val Ala Asp Thr Glu
            355                 360                 365
Ser Glu Gln Ala Asp Thr Trp Asp Leu Ser Glu Arg Pro Lys Glu Ile
            370                 375                 380
Lys Val Ser Lys Met Glu Gln Lys Phe Arg Met Leu Ser Gln Asp Ala
385                 390                 395                 400
Pro Thr Val Lys Glu Ser Cys Lys Thr Ser Asn Asn Ser Met
                405                 410                 415
Val Ser Asn Thr Leu Ala Lys Met Arg Ile Pro Asn Tyr Gln Leu Ser
            420                 425                 430
Pro Thr Lys Leu Pro Ser Ile Asn Lys Ser Lys Asp Arg Ala Ser Gln
            435                 440                 445
```

```
Gln Gln Gln Thr Asn Ser Ile Arg Asn Tyr Phe Gln Pro Ser Thr Lys
    450                 455                 460
Lys Arg Glu Arg Asp Glu Glu Asn Gln Glu Met Ser Ser Cys Lys Ser
465                 470                 475                 480
Ala Arg Ile Glu Thr Ser Cys Ser Leu Leu Glu Gln Thr Gln Pro Ala
                485                 490                 495
Thr Pro Ser Leu Trp Lys Asn Lys Glu Gln His Leu Ser Glu Asn Glu
            500                 505                 510
Pro Val Asp Thr Asn Ser Asp Asn Asn Leu Phe Thr Asp Thr Asp Leu
        515                 520                 525
Lys Ser Ile Val Lys Asn Ser Ala Ser Lys Ser His Ala Ala Glu Lys
    530                 535                 540
Leu Arg Ser Asn Lys Lys Arg Glu Met Asp Asp Val Ala Ile Glu Asp
545                 550                 555                 560
Glu Val Leu Glu Gln Leu Phe Lys Asp Thr Lys Pro Glu Leu Glu Ile
                565                 570                 575
Asp Val Lys Val Gln Lys Gln Glu Glu Asp Val Asn Val Arg Lys Arg
            580                 585                 590
Pro Arg Met Asp Ile Glu Thr Asn Asp Thr Phe Ser Asp Glu Ala Val
        595                 600                 605
Pro Glu Ser Ser Lys Ile Ser Gln Glu Asn Glu Ile Gly Lys Lys Arg
    610                 615                 620
Glu Leu Lys Glu Asp Ser Leu Trp Ser Ala Lys Glu Ile Ser Asn Asn
625                 630                 635                 640
Asp Lys Leu Gln Asp Ser Glu Met Leu Pro Lys Lys Leu Leu Leu
                645                 650                 655
Thr Glu Phe Arg Ser Leu Val Ile Lys Asn Ser Thr Ser Arg Asn Pro
            660                 665                 670
Ser Gly Ile Asn Asp Asp Tyr Gly Gln Leu Lys Asn Phe Lys Lys Phe
        675                 680                 685
Lys Lys Val Thr Tyr Pro Gly Ala Gly Lys Leu Pro His Ile Ile Gly
    690                 695                 700
Gly Ser Asp Leu Ile Ala His His Ala Arg Lys Asn Thr Glu Leu Glu
705                 710                 715                 720
Glu Trp Leu Arg Gln Glu Met Glu Val Gln Asn Gln His Ala Lys Glu
                725                 730                 735
Glu Ser Leu Ala Asp Asp Leu Phe Arg Tyr Asn Pro Tyr Leu Lys Arg
            740                 745                 750
Arg Arg

<210> SEQ ID NO 3
<211> LENGTH: 87
<212> TYPE: PRT
<213> ORGANISM: Homo sapiens
<220> FEATURE:
<221> NAME/KEY: UNSURE
<222> LOCATION: (48)...(48)
<223> OTHER INFORMATION: Unsure

<400> SEQUENCE: 3

Tyr Val Val Gly Arg Lys Asn Cys Ala Ile Leu Ile Glu Asn Asp Gln
  1               5                  10                  15
Ser Ile Ser Arg Asn His Ala Val Leu Thr Ala Asn Phe Ser Val Thr
                20                  25                  30
Asn Leu Ser Gln Thr Asp Glu Ile Pro Val Leu Thr Leu Lys Asn Xaa
```

```
                35                  40                  45
Lys Tyr Gly Thr Phe Val Asn Glu Glu Lys Met Gln Asn Gly Phe Ser
        50                  55                  60

Arg Thr Leu Lys Ser Val Asp Gly Ile Thr Phe Gly Val Phe Gly Ser
 65                  70                  75                  80

Lys Phe Arg Ile Glu Tyr Glu
                85

<210> SEQ ID NO 4
<211> LENGTH: 87
<212> TYPE: PRT
<213> ORGANISM: Homo sapiens

<400> SEQUENCE: 4

Tyr Ser Ile Gly Arg Ser Ser Lys Asn Pro Leu Ile Ile Lys Asn Asp
 1               5                  10                  15

Lys Ser Ile Ser Arg Gln His Ile Thr Phe Lys Trp Glu Ile Asn Asn
                20                  25                  30

Ser Ser Asp Leu Lys His Ser Ser Leu Cys Leu Val Asn Lys Gly Lys
            35                  40                  45

Leu Thr Ser Leu Asn Lys Lys Phe Met Lys Val Gly Glu Thr Phe Thr
        50                  55                  60

Ile Asn Ala Ser Cys Val Leu Lys Ser Thr Ile Glu Leu Gly Thr Thr
 65                  70                  75                  80

Pro Ile Arg Ile Glu Phe Glu
                85

<210> SEQ ID NO 5
<211> LENGTH: 13
<212> TYPE: PRT
<213> ORGANISM: Homo sapiens

<400> SEQUENCE: 5

Asn Pro Ser Gly Leu Asn Asp Asp Tyr Gly Gln Leu Lys
 1               5                  10

<210> SEQ ID NO 6
<211> LENGTH: 680
<212> TYPE: PRT
<213> ORGANISM: Homo sapiens

<400> SEQUENCE: 6

Met Ser Thr Ala Asp Ala Leu Asp Asp Glu Asn Thr Phe Lys Ile Leu
 1               5                  10                  15

Val Ala Thr Asp Ile His Leu Gly Phe Met Glu Lys Asp Ala Ala Arg
                20                  25                  30

Gly Asn Asp Thr Phe Val Thr Leu Asp Glu Ile Leu Arg Leu Ala Gln
            35                  40                  45

Glu Asn Glu Val Asp Phe Ile Leu Leu Gly Gly Asp Leu Phe His Glu
        50                  55                  60

Asn Lys Pro Ser Arg Lys Thr Leu His Thr Cys Leu Glu Leu Leu Arg
 65                  70                  75                  80

Lys Tyr Cys Met Gly Asp Arg Pro Val Gln Phe Glu Ile Leu Ser Asp
                85                  90                  95

Gln Ser Val Asn Phe Gly Phe Ser Lys Phe Pro Trp Val Asn Tyr Gln
                100                 105                 110

Asp Gly Asn Leu Asn Ile Ser Ile Pro Val Phe Ser Ile His Gly Asn
            115                 120                 125
```

```
His Asp Asp Pro Thr Gly Ala Asp Ala Leu Cys Ala Leu Asp Ile Leu
    130                 135                 140
Ser Cys Ala Gly Phe Val Asn His Phe Gly Arg Ser Met Ser Val Glu
145                 150                 155                 160
Lys Ile Asp Ile Ser Pro Val Leu Leu Gln Lys Gly Ser Thr Lys Ile
                165                 170                 175
Ala Leu Tyr Gly Leu Gly Ser Ile Pro Asp Glu Arg Leu Tyr Arg Met
            180                 185                 190
Phe Val Asn Lys Lys Val Thr Met Leu Arg Pro Lys Glu Asp Glu Asn
        195                 200                 205
Ser Trp Phe Asn Leu Phe Val Ile His Gln Asn Arg Ser Lys His Gly
    210                 215                 220
Ser Thr Asn Phe Ile Pro Glu Gln Phe Leu Asp Asp Phe Ile Asp Leu
225                 230                 235                 240
Val Ile Trp Gly His Glu His Glu Cys Lys Ile Ala Pro Thr Lys Asn
                245                 250                 255
Glu Gln Gln Leu Phe Tyr Ile Ser Gln Pro Gly Ser Ser Val Val Thr
            260                 265                 270
Ser Leu Ser Pro Gly Glu Ala Val Lys Lys His Val Gly Leu Leu Arg
        275                 280                 285
Ile Lys Gly Arg Lys Met Asn Met His Lys Ile Pro Leu His Thr Val
    290                 295                 300
Arg Gln Phe Phe Met Glu Asp Ile Val Leu Ala Asn His Pro Asp Ile
305                 310                 315                 320
Phe Asn Pro Asp Asn Pro Lys Val Thr Gln Ala Ile Gln Ser Phe Cys
                325                 330                 335
Leu Glu Lys Ile Glu Glu Met Leu Glu Asn Ala Glu Arg Glu Arg Leu
            340                 345                 350
Gly Asn Ser His Gln Pro Glu Lys Pro Leu Val Arg Leu Arg Val Asp
        355                 360                 365
Tyr Ser Gly Gly Phe Glu Pro Phe Ser Val Leu Arg Phe Ser Gln Lys
    370                 375                 380
Phe Val Asp Arg Val Ala Asn Pro Lys Asp Ile Ile His Phe Phe Arg
385                 390                 395                 400
His Arg Glu Gln Lys Glu Lys Thr Gly Glu Glu Ile Asn Phe Gly Lys
                405                 410                 415
Leu Ile Thr Lys Pro Ser Glu Gly Thr Thr Leu Arg Val Glu Asp Leu
            420                 425                 430
Val Lys Gln Tyr Phe Gln Thr Ala Glu Lys Asn Val Gln Leu Ser Leu
        435                 440                 445
Leu Thr Glu Arg Gly Met Gly Glu Ala Val Gln Glu Phe Val Asp Lys
    450                 455                 460
Glu Glu Lys Asp Ala Ile Glu Glu Leu Val Lys Tyr Gln Leu Glu Lys
465                 470                 475                 480
Thr Gln Arg Phe Leu Lys Glu Arg His Ile Asp Ala Leu Glu Asp Lys
                485                 490                 495
Ile Asp Glu Glu Val Arg Arg Phe Arg Glu Thr Arg Gln Lys Asn Thr
            500                 505                 510
Asn Glu Glu Asp Asp Glu Val Arg Glu Ala Met Thr Arg Ala Arg Ala
        515                 520                 525
Leu Arg Ser Gln Ser Glu Glu Ser Ala Ser Ala Phe Ser Ala Asp Asp
    530                 535                 540
```

```
Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
            580                 585                 590

Gly Arg Ala Phe Lys Ser Thr Arg Gln Gln Pro Ser Arg Asn Val Thr
        595                 600                 605

Thr Lys Asn Tyr Ser Glu Val Ile Glu Val Asp Glu Ser Asp Val Glu
    610                 615                 620

Glu Asp Ile Phe Pro Thr Thr Ser Lys Thr Asp Gln Arg Trp Ser Ser
625                 630                 635                 640

Thr Ser Ser Ser Lys Ile Met Ser Gln Ser Gln Val Ser Lys Gly Val
                645                 650                 655

Asp Phe Glu Ser Ser Glu Asp Asp Asp Asp Pro Phe Met Asn Thr
            660                 665                 670

Ser Ser Leu Arg Arg Asn Arg Arg
            675                 680

<210> SEQ ID NO 7
<211> LENGTH: 2060
<212> TYPE: DNA
<213> ORGANISM: Homo sapiens

<400> SEQUENCE: 7
```

| | | | | |
|---|---|---|---|---|
| aattcgggcc gaaagaaga cagccttggg tcgcgattgt ggggcttcga agagtccagc | | | | 60 |
| agtgggaatt tctagaattt ggaatcgagt gcattttctg acatttgagt acagtaccca | | | | 120 |
| ggggttcttg gagaagaacc tggtcccaga ggagcttgac tgaccataaa atgagtact | | | | 180 |
| gcagatgcac ttgatgatga aaacacattt aaaatattag ttgcaacaga tattcatctt | | | | 240 |
| ggatttatgg agaaagatgc agccagagga atgatacgt tgtaacact cgatgaaatt | | | | 300 |
| ttaagacttg cccaggaaaa tgaagtggat tttatttgt taggtggtga tcttttcat | | | | 360 |
| gaaaataagc cctcaaggaa acattacat acctgcctcg agttattaag aaaatattgt | | | | 420 |
| atgggtgatc ggcctgtcca gtttgaaatt ctcagtgatc agtcagtcaa ctttggtttt | | | | 480 |
| agtaagtttc catgggtgaa ctatcaagat ggcaacctca acatttcaat tccagtgttt | | | | 540 |
| agtattcatg gcaatcatga cgatcccaca ggggcagatg cactttgtgc cttggacatt | | | | 600 |
| ttaagttgtg ctggatttgt aaatcacttt ggacgttcaa tgtctgtgga aagatagac | | | | 660 |
| attagtccgg ttttgcttca aaaggaagc acaaagattg cgctatatgg tttaggatcc | | | | 720 |
| attccagatg aaaggctcta tcgaatgttt gtcaataaaa aagtaacaat gttgagacca | | | | 780 |
| aaggaagatg agaactcttg gtttaactta tttgtgattc atcagaacag gagtaaacat | | | | 840 |
| ggaagtacta acttcattcc agaacaattt ttggatgact tcattgatct tgttatctgg | | | | 900 |
| ggccatgaac atgagtgtaa aatagctcca accaaaaatg aacaacagct gttttatatc | | | | 960 |
| tcacaacctg gaagctcagt ggttacttct ctttccccag gagaagctgt aaagaaacat | | | | 1020 |
| gttggtttgc tgcgtattaa agggaggaag atgaatatgc ataaaattcc tcttcacaca | | | | 1080 |
| gtgcggcagt ttttcatgga ggatattgtt ctagctaatc atccagacat tttaacccca | | | | 1140 |
| gataatccta agtaaccca agccatacaa agcttctgtt tggagaagat tgaagaaatg | | | | 1200 |
| cttgaaaatg ctgaacggga acgtctgggt aattctcacc agccagagaa gcctcttgta | | | | 1260 |
| cgactgcgag tggactatag tggaggtttt gaacctttca gtgttcttcg ctttagccag | | | | 1320 |

-continued

```
aaatttgtgg atcgggtagc taatccaaaa gacattatcc attttttcag gcatagagaa    1380
caaaaggaaa aaacaggaga agagatcaac tttgggaaac ttatcacaaa gccttcagaa    1440
ggaacaactt taagggtaga agatcttgta aaacagtact ttcaaaccgc agagaagaat    1500
gtgcagctct cactgctaac agaaagaggg atgggtgaag cagtacaaga atttgtggac    1560
aaggaggaga aagatgccat tgaggaatta gtgaaatacc agttggaaaa aacacagcga    1620
tttcttaaag aacgtcatat tgatgccctc gaagacaaaa tcgatgagga ggtacgtcgt    1680
ttcagagaaa ccagacaaaa aaatactaat gaagaagatg atgaagtccg tgaggctatg    1740
accagggcca gagcactcag atctcagtca gaggagtctg cttctgcctt tagtgctgat    1800
gaccttatga gtatagattt agcagaacag atggctaatg actctgatga tagcatctca    1860
gcagcaacca acaaaggaag aggccgagga agaggtcgaa gaggtggaag agggcagaat    1920
tcagcatcga gaggagggtc tcaaagagga agagccttta aatctacaag acagcagcct    1980
tcccgaaatg tcactactaa gaattattca gaggtgattg agtagatgaa atcagatgtg    2040
gaagaagaca ttttttcctac                                              2060
```

<210> SEQ ID NO 8
<211> LENGTH: 680
<212> TYPE: PRT
<213> ORGANISM: Homo sapiens

<400> SEQUENCE: 8

```
Met Ser Thr Ala Asp Ala Leu Asp Asp Glu Asn Thr Phe Lys Ile Leu
  1               5                  10                  15

Val Ala Thr Asp Ile His Leu Gly Phe Met Glu Lys Asp Ala Ala Arg
                 20                  25                  30

Gly Asn Asp Thr Phe Val Thr Leu Asp Glu Ile Leu Arg Leu Ala Gln
             35                  40                  45

Glu Asn Glu Val Asp Phe Ile Leu Leu Gly Gly Asp Leu Phe His Glu
         50                  55                  60

Asn Lys Pro Ser Arg Lys Thr Leu His Thr Cys Leu Glu Leu Leu Arg
 65                  70                  75                  80

Lys Tyr Cys Met Gly Asp Arg Pro Val Gln Phe Glu Ile Leu Ser Asp
                 85                  90                  95

Gln Ser Val Asn Phe Gly Phe Ser Lys Phe Pro Trp Val Asn Tyr Gln
                100                 105                 110

Asp Gly Asn Leu Asn Ile Ser Ile Pro Val Phe Ser Ile His Gly Asn
            115                 120                 125

His Asp Asp Pro Thr Gly Ala Asp Ala Leu Cys Ala Leu Asp Ile Leu
        130                 135                 140

Ser Cys Ala Gly Phe Val Asn His Phe Gly Arg Ser Met Ser Val Glu
145                 150                 155                 160

Lys Ile Asp Ile Ser Pro Val Leu Leu Gln Lys Gly Ser Thr Lys Ile
                165                 170                 175

Ala Leu Tyr Gly Leu Gly Ser Ile Pro Asp Glu Arg Leu Tyr Arg Met
            180                 185                 190

Phe Val Asn Lys Lys Val Thr Met Leu Arg Pro Lys Glu Asp Glu Asn
        195                 200                 205

Ser Trp Phe Asn Leu Phe Val Ile His Gln Asn Arg Ser Lys His Gly
    210                 215                 220

Ser Thr Asn Phe Ile Pro Glu Gln Phe Leu Asp Asp Phe Ile Asp Leu
225                 230                 235                 240
```

```
Val Ile Trp Gly His Glu His Glu Cys Lys Ile Ala Pro Thr Lys Asn
                245                 250                 255

Glu Gln Gln Leu Phe Tyr Ile Ser Gln Pro Gly Ser Ser Val Val Thr
                260                 265                 270

Ser Leu Ser Pro Gly Glu Ala Val Lys His Val Gly Leu Leu Arg
            275                 280                 285

Ile Lys Gly Arg Lys Met Asn Met His Lys Ile Pro Leu His Thr Val
290                 295                 300

Arg Gln Phe Phe Met Glu Asp Ile Val Leu Ala Asn His Pro Asp Ile
305                 310                 315                 320

Phe Asn Pro Asp Asn Pro Lys Val Thr Gln Ala Ile Gln Ser Phe Cys
                325                 330                 335

Leu Glu Lys Ile Glu Glu Met Leu Glu Asn Ala Glu Arg Glu Arg Leu
                340                 345                 350

Gly Asn Ser His Gln Pro Glu Lys Pro Leu Val Arg Leu Arg Val Asp
            355                 360                 365

Tyr Ser Gly Gly Phe Glu Pro Phe Ser Val Leu Arg Phe Ser Gln Lys
            370                 375                 380

Phe Val Asp Arg Val Ala Asn Pro Lys Asp Ile Ile His Phe Phe Arg
385                 390                 395                 400

His Arg Glu Gln Lys Glu Lys Thr Gly Glu Glu Ile Asn Phe Gly Lys
                405                 410                 415

Leu Ile Thr Lys Pro Ser Glu Gly Thr Thr Leu Arg Val Glu Asp Leu
                420                 425                 430

Val Lys Gln Tyr Phe Gln Thr Ala Glu Lys Asn Val Gln Leu Ser Leu
            435                 440                 445

Leu Thr Glu Arg Gly Met Gly Glu Ala Val Gln Glu Phe Val Asp Lys
        450                 455                 460

Glu Glu Lys Asp Ala Ile Glu Glu Leu Val Lys Tyr Gln Leu Glu Lys
465                 470                 475                 480

Thr Gln Arg Phe Leu Lys Glu Arg His Ile Asp Ala Leu Glu Asp Lys
                485                 490                 495

Ile Asp Glu Glu Val Arg Arg Phe Arg Glu Thr Arg Gln Lys Asn Thr
                500                 505                 510

Asn Glu Glu Asp Asp Glu Val Arg Glu Ala Met Thr Arg Ala Arg Ala
            515                 520                 525

Leu Arg Ser Gln Ser Glu Glu Ser Ala Ser Phe Ser Ala Asp Asp
        530                 535                 540

Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
            580                 585                 590

Gly Arg Ala Phe Lys Ser Thr Arg Gln Gln Pro Ser Arg Asn Val Thr
        595                 600                 605

Thr Lys Asn Tyr Ser Glu Val Ile Glu Val Asp Ser Asp Val Glu
            610                 615                 620

Glu Asp Ile Phe Pro Thr Thr Ser Lys Thr Asp Gln Arg Trp Ser Ser
625                 630                 635                 640

Thr Ser Ser Ser Lys Ile Met Ser Gln Ser Gln Val Ser Lys Gly Val
                645                 650                 655

Asp Phe Glu Ser Ser Glu Asp Asp Asp Asp Pro Phe Met Asn Thr
```

```
                    660                 665                 670
Ser Ser Leu Arg Arg Asn Arg Arg
            675                 680

<210> SEQ ID NO 9
<211> LENGTH: 20
<212> TYPE: PRT
<213> ORGANISM: Homo sapiens

<400> SEQUENCE: 9

Gln Pro Pro Gln Ile Glu Ser Phe Tyr Pro Pro Leu Asp Glu Pro Ser
1               5                   10                  15

Ile Gly Ser Lys
            20

<210> SEQ ID NO 10
<211> LENGTH: 13
<212> TYPE: PRT
<213> ORGANISM: Homo sapiens

<400> SEQUENCE: 10

Leu Ser Ser Ala Val Val Phe Gly Gly Gly Glu Ala Arg
1               5                   10

<210> SEQ ID NO 11
<211> LENGTH: 11
<212> TYPE: PRT
<213> ORGANISM: Homo sapiens

<400> SEQUENCE: 11

Trp Ile Gln Ser Ile Met Asp Met Leu Gln Arg
1               5                   10

<210> SEQ ID NO 12
<211> LENGTH: 21
<212> TYPE: PRT
<213> ORGANISM: Homo sapiens

<400> SEQUENCE: 12

Gln Gly Leu Arg Pro Ile Pro Glu Ala Glu Ile Gly Leu Ala Val Ile
1               5                   10                  15

Phe Met Thr Thr Lys
            20

<210> SEQ ID NO 13
<211> LENGTH: 17
<212> TYPE: PRT
<213> ORGANISM: Homo sapiens

<400> SEQUENCE: 13

Thr Thr Thr Pro Gly Pro Ser Leu Ser Gln Gly Val Ser Val Asp Glu
1               5                   10                  15

Lys

<210> SEQ ID NO 14
<211> LENGTH: 11
<212> TYPE: PRT
<213> ORGANISM: Homo sapiens

<400> SEQUENCE: 14

Met Leu Ser Gln Asp Ala Pro Thr Val Lys Glu
1               5                   10
```

```
<210> SEQ ID NO 15
<211> LENGTH: 15
<212> TYPE: PRT
<213> ORGANISM: Homo sapiens

<400> SEQUENCE: 15

Thr Ser Ser Asn Asn Asn Ser Met Val Ser Asn Thr Leu Ala Lys
 1               5                  10                  15

<210> SEQ ID NO 16
<211> LENGTH: 16
<212> TYPE: PRT
<213> ORGANISM: Homo sapiens

<400> SEQUENCE: 16

Ile Pro Asn Tyr Gln Leu Ser Pro Thr Lys Leu Pro Ser Ile Asn Lys
 1               5                  10                  15

<210> SEQ ID NO 17
<211> LENGTH: 9
<212> TYPE: PRT
<213> ORGANISM: Homo sapiens

<400> SEQUENCE: 17

Asn Tyr Phe Gln Pro Ser Thr Lys Lys
 1               5

<210> SEQ ID NO 18
<211> LENGTH: 27
<212> TYPE: PRT
<213> ORGANISM: Homo sapiens

<400> SEQUENCE: 18

Asn Lys Glu Gln His Leu Ser Glu Asn Glu Pro Val Asp Thr Asn Ser
 1               5                  10                  15

Asp Asn Asn Leu Phe Thr Asp Thr Asp Leu Lys
                20                  25

<210> SEQ ID NO 19
<211> LENGTH: 17
<212> TYPE: PRT
<213> ORGANISM: Homo sapiens

<400> SEQUENCE: 19

Glu Met Asp Asp Val Ala Ile Glu Asp Glu Val Leu Glu Gln Leu Phe
 1               5                  10                  15

Lys

<210> SEQ ID NO 20
<211> LENGTH: 19
<212> TYPE: PRT
<213> ORGANISM: Homo sapiens

<400> SEQUENCE: 20

Met Asp Ile Glu Thr Asn Asp Thr Phe Ser Asp Glu Ala Val Pro Glu
 1               5                  10                  15

Ser Ser Lys

<210> SEQ ID NO 21
<211> LENGTH: 9
<212> TYPE: PRT
<213> ORGANISM: Homo sapiens
```

-continued

```
<400> SEQUENCE: 21

Glu Leu Lys Glu Asp Ser Trp Ala Lys
 1               5

<210> SEQ ID NO 22
<211> LENGTH: 8
<212> TYPE: PRT
<213> ORGANISM: Homo sapiens

<400> SEQUENCE: 22

Lys Leu Leu Leu Thr Glu Phe Arg
 1               5

<210> SEQ ID NO 23
<211> LENGTH: 13
<212> TYPE: PRT
<213> ORGANISM: Homo sapiens

<400> SEQUENCE: 23

Asn Pro Ser Gly Ile Asn Asp Asp Tyr Gly Gln Leu Lys
 1               5                   10

<210> SEQ ID NO 24
<211> LENGTH: 10
<212> TYPE: PRT
<213> ORGANISM: Homo sapiens

<400> SEQUENCE: 24

Glu Glu Ser Leu Ala Asp Asp Leu Phe Arg
 1               5                   10
```

DNA ENCODING A DNA REPAIR PROTEIN

CROSS-REFERENCE TO RELATED APPLICATION

This application is a divisional of U.S. application Ser. No. 09/067,641 filed Apr. 27, 1998 now abandoned.

STATEMENT OF GOVERNMENT RIGHTS

This invention was made with grants from the Government of the United States of America (grants GM07133, GM52095, GM56888, RR11823, CA09215 and CA40046 from the National Institutes of Health, contract number 4459-011502 from the United States Department of Energy, and grant BIR9214821 from the National Science Foundation Science and Technology Center). The Government may have certain rights in the invention.

BACKGROUND OF THE INVENTION

Nijmegen Breakage Syndrome (NBS) is a rare autosomal recessive disorder characterized by microcephaly, growth retardation, immunodeficiency, and an increased incidence of cancer, e.g., hematopoietic malignancy (van der Burgt et al., 1996; and Weemaes et al., 1981). At the cellular level, NBS is characterized by cell cycle defects and radiation sensitivity. The clinical features of NBS overlap to some extent with those of ataxia telangiectasia (AT); thus it has been described as an AT variant syndrome (Saar et al., 1997). However, NBS is genetically distinct. The two syndromes are clinically distinguishable in that NBS patients do not exhibit neurological abnormalities, telangiectasia or increased α-feto protein levels observed in AT patients (reviewed in Shiloh, 1997).

Nonetheless, NBS and AT exhibit remarkably similar phenotypes at the cellular level, suggesting that the corresponding gene products function in the same pathway. Unlinked non-complementation of chromosome instability was observed in heterokaryons of AT and NBS fibroblasts, leading to speculation that the respective gene products are physically associated (Stumm et al., 1997). Cells from both NBS and AT patients show increased sensitivity to ionizing radiation (IR) as well as increased levels of spontaneous and induced chromosomal fragility. In addition, NBS and AT cells fail to induce p53 at the G1/S checkpoint, and fail to suppress DNA synthesis in response to ionizing radiation (radioresistant DNA synthesis) (Jongmans et al., 1997; Perez-Vera et al., 1997; Sullivan et al., 1997; Taalman et al., 1983; and Young and Painter, 1989) (AT reviewed in Hoekstra, 1997; and Shiloh, 1997). Together, these data suggest that the AT gene product, ATM, is a component of, or functions in close proximity to, the primary sensor of DNA damage.

Accordingly, AT phenotypes can be explained by the failure to signal the presence of DNA damage. Hence, IR sensitivity in AT cells is generally attributed to defects in the cellular DNA damage response. However, some data suggest that DNA repair functions in AT cells may also be affected (Blocher et al., 1991; Cornforth and Bedford, 1985; Murnane, 1995; and Pandita and Hittelman, 1992). Consistent with this notion, cells established from AT patients exhibit increased rates of intrachromosomal DNA recombination (Meyn, 1993).

DNA damage includes double strand breaks in the DNA. These breaks in DNA are repaired by the double strand break (DSB) repair complex. The human DSB complex, also referred to as the "hMre11/hRad50 complex", was shown to consist of five proteins: hMre11, hRad50, and three additional proteins of 95 kDa, 200 kDa, and 400 kDa (Dolganov et al., 1996; Petrini et al., 1995). The phenotypic features of yeast lacking the counterparts to hMre11 and hRad50, i.e., Scmre11 and Scrad50 mutants, include hyperrecombination, sensitivity to DNA damaging agents, and DNA repair deficiency (Ajimura et al., 1993; and Game, 1993). These features are reminiscent of chromosomal instability syndromes such as AT, NBS, Bloom syndrome and others (Ellis, 1997; Fukuchi et al., 1989; Gatti et al., 1991; Meyn, 1995; and van der Burgt et al., 1996). The conservation of Mre11 and Rad50 functions predicts that similar phenotypic outcomes would result from mutations in humans that affect the hMre11/hRad50 protein complex. However, deficiencies in hMre11 or hRad50 have not been associated with any known chromosomal instability syndromes. Recent attempts to create a null mre11 mutant in murine embryonic stem cells indicate that the gene is essential, suggesting that spontaneous homozygous null mutants of hMRE11 and hRAD50 will not be found in the human population (Xiao and Weaver, 1997).

Thus, there is a need to isolate and characterize genes encoding double strand DNA repair proteins.

SUMMARY OF THE INVENTION

The invention provides an isolated and purified nucleic acid molecule comprising a nucleic acid segment encoding a DNA repair polypeptide or protein, a biologically active subunit or variant thereof, wherein the polypeptide or protein has a molecular weight of about 95000 Da as determined by SDS-PAGE (herein referred to as "p95"). The DNA repair polypeptide forms part of a complex that is associated with the repair of DSB in nuclear DNA. Preferably, the nucleic acid molecule of the invention encodes a polypeptide having SEQ ID NO:2, e.g., a polypeptide which is encoded by a DNA segment comprising SEQ ID NO:1 or a variant thereof. The nucleic acid molecules of the invention may comprise RNA or DNA. Also provided are antisense nucleic acid molecules which are the complement of nucleic acid segments encoding a DNA repair polypeptide or protein, for example, an isolated and purified DNA molecule comprising a DNA segment complementary to SEQ ID NO:1, or a portion thereof.

As described hereinbelow, a gene encoding the p95 subunit of the hMre11/hRad50 complex was isolated and characterized by direct protein sequencing. Surprisingly, p95 has only limited homology to the 95 kDa *S. cerevisiae* Xrs2, a member of the *S. cerevisiae* hMre11/Rad50/Xrs2 protein complex. The locus encoding p95 maps to human chromosome segment 8q21.3, a region that was recently reported to contain the NBS locus (Saar et al., 1997). The isolated p95 cDNA was compared to the gene defective in NBS, NBS1, and it was found that p95 is the product of the NBS1 gene. The results described below also show that p95 protein is not present in cell lines established from NBS patients. Moreover, the results show that p95 is an integral member of the hMre11/hRad50 complex and that the function of the complex is impaired in cells from NBS patients as these cells fail to form hMre11/hRad50 ionizing radiation-induced foci. In light of the radiation sensitivity and DNA damage dependent cell cycle checkpoint defects in NBS cells, these results provide evidence for a direct molecular link between DSB repair and cell cycle checkpoint functions. Further, these data define a direct molecular link between proteins involved in DSB repair and the activation of cellular DNA damage responses.

The invention also provides probes and primers comprising at least a portion of the nucleic acid molecules of the invention. The probes or primers of the invention are preferably detectably labeled or have a binding site for a detectable label. Preferably, the probes or primers of the invention are at least about 7, more preferably at least about 15, contiguous nucleotides bases having at least about 80% identity, more preferably at least about 90% identity, to the isolated nucleic acid molecules of the invention. Such probes or primers are useful to detect, quantify, isolate and/or amplify DNA strands with complementary to sequences related to p95 in mammalian tissue samples.

Another embodiment of the invention is an expression cassette comprising a promoter operably linked to a DNA segment encoding p95, a biologically active subunit or variant thereof, as well as host cells comprising said expression cassettes. Preferably, the expression cassette of the invention encodes a fusion polypeptide comprising p95, biologically active subunit or variant thereof. A further embodiment of the invention is an expression cassette comprising a promoter operably linked to a DNA segment encoding a fusion polypeptide comprising Mre11, a biologically active subunit or variant thereof.

The expression cassettes of the invention may be employed in a method of altering the amount of a DNA repair polypeptide in a cell. The method comprises introducing into a host cell a DNA segment encoding p95, a biologically active subunit or variant thereof, or the complement thereof, operably linked to a promoter functional in the host cell, so as to yield a transformed host cell. The DNA segment is expressed in the transformed host cell as in an amount that alters the amount of the polypeptide produced by the transformed cell relative to the amount of the native p95 produced by a corresponding untransformed cell. If the DNA segment is operatively linked to the promoter in a sense orientation, the amount of the recombinant polypeptide produced by the transformed host cell is increased relative to the amount of the native polypeptide produced by the corresponding untransformed host cell. If the DNA segment is in an anti-sense orientation relative to the promoter, the amount of the native polypeptide produced by the transformed host cell is decreased relative to the amount of the native polypeptide produced by the corresponding untransformed host cell.

The invention further provides a method to produce a DNA repair polypeptide, comprising: culturing a host cell transformed with a DNA molecule comprising a DNA segment encoding a DNA repair polypeptide having a molecular weight of about 95000 Da, or a biologically active subunit or variant thereof, operably linked to a promoter, so that said host cell expresses said polypeptide. Preferably, the polypeptide is isolated from the host cell and purified. Therefore, the invention also provides isolated, purified p95, such as a polypeptide having SEQ ID NO:2), or a biologically active subunit or variant thereof. An isolated fusion polypeptide comprising SEQ ID NO:6 (Mre11), or a biologically active subunit or variant thereof, is also provided. The polypeptides of the invention are useful to detect antibodies that specifically react therewith, and in therapeutic applications.

The isolated polypeptide of the invention, preferably a fusion polypeptide comprising p95, a portion or a variant thereof, or a fusion polypeptide comprising Mre11, a portion or a variant thereof, is useful to prepare antisera specific for the polypeptide employed to raise the antisera. Thus, the isolated polypeptide of the invention is useful in an immunogenic composition or a vaccine, preferably in combination with a pharmaceutically acceptable carrier, which, when administered to an animal, induces the production of antibodies to said polypeptide. Hence, another embodiment of the invention is an isolated, purified antibody that specifically binds to a DNA repair polypeptide having a molecular weight of about 95000 Da. Antibodies within the scope of the invention include monoclonal antibodies and polyclonal antibodies. Also provided is a hybridoma cell line which produces a monoclonal antibody of the invention.

The invention also provides diagnostic and therapeutic methods. Diagnostic methods are useful to identify or detect a patient at risk of NBS, e.g., NBS heterozygotes, a mammal having an increased risk of cancer, or a mammal having an increased sensitivity to radiation or chemotherapy as a result of a decreased ability to repair DNA damage. For example, a diagnostic method for detecting nucleic acid encoding a DNA repair protein having a molecular weight of 95 kDa is provided. The method comprises contacting an amount of DNA obtained by reverse transcription of RNA from a mammalian, e.g., human, sample, such as a physiological sample, which comprises cells, with an amount of at least two oligonucleotides under conditions effective to amplify the DNA by a polymerase chain reaction so as to yield an amount of amplified DNA. At least one oligonucleotide is specific for the DNA encoding the DNA repair protein. Then the presence or absence of amplified p95 DNA is detected or determined.

Further provided is a method for detecting a predisposition for cancer in a human. The method comprises contacting an amount of DNA obtained by reverse transcription of RNA from a human physiological sample which comprises cells, with an amount of at least two oligonucleotides under conditions effective to amplify DNA encoding p95, or a subunit or variant thereof, by a polymerase chain reaction so as to yield an amount of amplified DNA. At least one oligonucleotide is specific for the DNA encoding the DNA repair protein. The presence or absence of the amplified DNA is detected or determined. A reduction in the amount of amplified DNA, relative to a control sample, is indicative of a predisposition to cancer in said human. The control sample can be cDNA obtained from human cells having and expressing two copies ("wild-type levels") of the p95 gene. Physiological samples useful in the methods of the invention include, but are not limited to, whole blood, fluid containing sperm, cells obtained by biopsy, e.g., tissues, such as chorionic villi or cultured cells.

Also provided is a method to detect a deletion in a gene encoding a DNA repair protein in a mammalian sample. The method comprises contacting a first amount of a labeled probe comprising at least a portion of a DNA encoding p95 with the test sample which comprises mammalian cells, for a sufficient time to form binary complexes between at least a portion of said amount of probe and a portion of the cells in the sample, wherein the DNA repair protein has a molecular weight of about 95000 Da. The amount of binary complexes is detected or determined and compared to the amount of binary complexes formed between a second amount of said probe and a control sample comprising mammalian cells, which cells contain two complete copies of the DNA repair protein gene, wherein a relative lesser amount of binary complexes formed with the test sample is indicative of deletion of at least a portion of the gene.

Yet another embodiment of the invention is a method to detect genetic modifications of a DNA repair protein gene in a mammalian biological or physiological sample. The method comprises contacting an amount of a labeled probe comprising at least a portion of DNA encoding the DNA repair protein with genomic DNA or RNA isolated from the mammalian physiological test sample, for a sufficient time to form binary complexes between at least a portion of said probe and a portion of the genomic DNA or RNA. The amount of binary complexes formed with the test sample is compared to the amount of binary complexes formed between a second amount of said probe and a genomic DNA or RNA sample from mammalian cells which contain and/or express two copies of the DNA repair protein gene, wherein a relative lesser amount of binary complexes formed with the test sample is indicative of deletion of the gene.

Another method to determine genetic modifications of a DNA repair protein gene in a mammalian physiological sample comprises subjecting DNA isolated from the test sample to a polymerase chain reaction using a plurality of primers under reaction conditions sufficient to amplify at least a portion of said gene to produce an amplification product, wherein the DNA repair protein has a molecular weight of about 95000 Da. Then it is determined whether the amplification product obtained from the test sample is different than an amplification product obtained by subjecting DNA isolated from a control sample which does not comprise genetic modifications of the gene to a polymerase chain reaction using the plurality of said primers under reaction conditions sufficient to amplify at least a portion of the gene. Preferably, the method further comprises analyzing the amplification product of the test sample to determine the presence or absence of a point mutation in the p95 gene.

Also provided is a method for detecting or determining a DNA repair protein in a mammalian physiological or biological sample comprising cells. The method contacting an amount of an agent which specifically reacts with the DNA repair protein with the sample to be tested for a sufficient time to allow the formation of binary complexes between at least a portion of said agent and a portion of said protein, wherein the DNA repair protein has a molecular weight of about 95000 Da. The presence or amount of the protein complexed with said agent is then detected or determined. Preferably, the sample is a mammalian tissue sample. It is preferred that the agent which specifically reacts with the DNA repair protein is an antibody of the invention, which optionally may be labeled or contain a detectable label. It is also preferred that the detection of complex formation is accomplished with a second agent comprising a detectable label or which binds to a detectable label, e.g., a labeled antibody, to form a detectable ternary complex.

Yet a further embodiment of the invention is method for detecting or determining a DNA repair protein in a sample of human physiological fluid comprising isolated polypeptides or proteins. This method comprises contacting an amount of an agent which specifically reacts with the DNA repair protein with the sample to be tested for a sufficient time to allow the formation of binary complexes between at least a portion of said agent and a portion of said protein, wherein the DNA repair protein has a molecular weight of about 95000 Da. The amount of complex formation is then detected or determined.

Therapeutic methods of the invention include methods to supplement a deficiency of p95, e.g., via gene therapy or administration of native or recombinant p95, or as a preventative therapy in "normal" individuals exposed to agents that mediate DNA damage. For example, patients having decreased amounts of p95, e.g., p95 heterozygotes, may have an increased risk of cancer when exposed to routine X-rays, e.g., mammography. Other therapeutic methods employ targeted delivery of inhibitors of p95 to inhibit or treat cancer. Thus, the administration of an inhibitor of p95 to tumor cells may increase tumor cell sensitivity to radiation ("radiosensitizers") or chemotherapy. To identify such inhibitors, methodologies including, but not limited to, phage display, may be employed to identify peptides or polypeptides that specifically bind to p95.

Also provided is a transgenic non-human animal, e.g., a rodent such as a mouse or rat, whose cells contain a chimeric DNA sequence, said chimeric DNA sequence comprising: a transcription control sequence and a DNA segment which encodes a DNA repair polypeptide having a molecular weight of about 95000 Da, or a biologically active subunit, wherein the transcription control sequence and the DNA segment are operatively linked to each other and are integrated into the genome of the animal, and wherein the DNA segment is expressed in the transgenic animal so as to result in said animal exhibiting increased amounts of the DNA repair polypeptide. Another embodiment of the invention is a transgenic non-human animal which expresses a DNA segment encoding a variant, or a subunit thereof, of the DNA repair polypeptide, which, when the variant p95 polypeptide or subunit thereof is present in the Mre11/Rad50 complex, disrupts the function of the complex and so results in an animal exhibiting aberrant or decreased DNA repair.

Further provided is a method to express of p95 in a transgenic non-human animal. The method comprises expressing a chimeric DNA sequence in the cells of a transgenic animal, wherein the chimeric DNA sequence comprises a transcription control sequence operatively linked to a DNA segment which encodes a DNA repair polypeptide having a molecular weight of about 95000 Da as determined by SDS-PAGE, wherein the chimeric DNA sequence is integrated into the genome of the animal, and wherein the DNA segment is expressed in the transgenic animal so as to result in said animal exhibiting increased amounts of the DNA repair polypeptide.

Yet another embodiment of the invention is a method of using a transgenic animal, e.g., a transgenic rodent, to screen for an agent that modulates a DNA repair polypeptide. The method comprises exposing or administering the agent to the transgenic rodent, wherein the transgenic rodent comprises a chimeric DNA sequence comprising a transcription control sequence operatively linked to a DNA segment which encodes a DNA repair polypeptide having a molecular weight of about 95000 Da as determined by SDS-PAGE, wherein the chimeric DNA sequence is integrated into the genome of the rodent, and wherein the DNA segment is expressed as the DNA repair polypeptide in the transgenic rodent. Then it is determined whether said agent modulates the amount of the DNA repair polypeptide in the transgenic rodent relative to a transgenic rodent which has not been administered the agent. Preferably, the agent inhibits or reduces the amount or activity of p95. Alternatively, the agent increases the amount or activity of p95.

The invention also provide a recombinant non-human animal, the genome of which does not encode a functional DNA repair protein having a molecular weight of about 95000 Da, e.g., a p95 "knock-out" mouse. The recombinant non-human animal is useful to study DNA repair, efficacy of radiotherapy and to test agents for their therapeutic potential.

BRIEF DESCRIPTION OF THE FIGURES

FIG. 12. Codons for specified amino acids.

FIG. 13. Exemplary and preferred amino acid substitutions.

FIG. 14. cDNA sequence of p95 (SEQ ID NO:1).

FIG. 15. Amino acid sequence of p95 SEQ ID NO:2.

DETAILED DESCRIPTION OF THE INVENTION

Definitions

Figure 1:
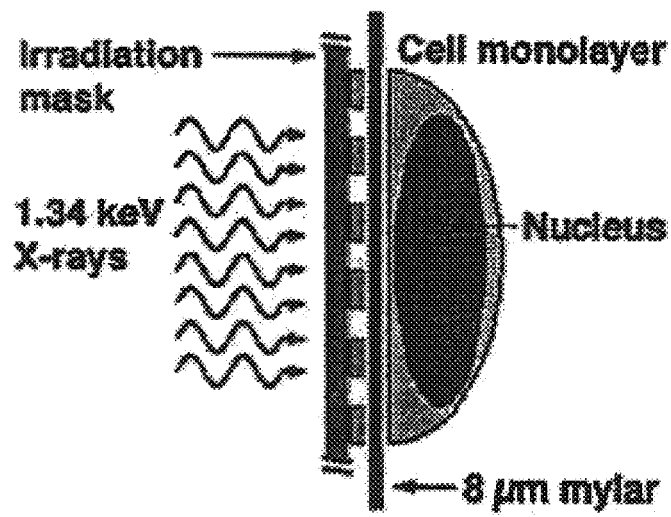
FIG. 1. (A) Diagram of the partial volume irradiation scheme. The thickness of the mylar surface (8 μm) is not drawn to scale. (B) Scanning electron micrograph of irradiation mask. Bar, 1 μm.
Figure 1:
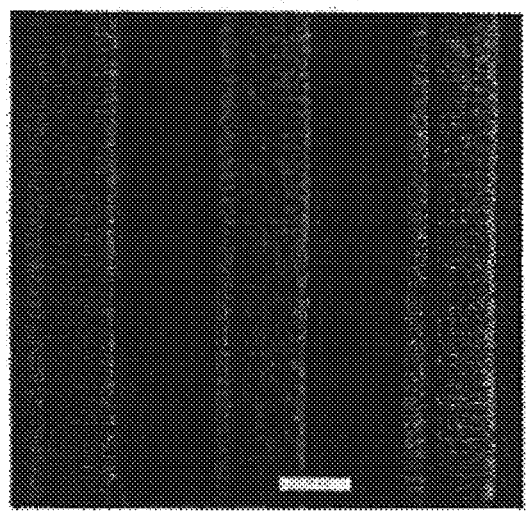

As used herein, the terms "isolated and/or purified" refer to in vitro preparation, isolation and/or purification of a nucleic acid molecule or polypeptide of the invention, so that it is not associated with in vivo substances.

As used herein, a "DNA repair polypeptide or protein having a molecular weight of 95000 Da" or "p95" refers to a polypeptide which is part of the mammalian Mre11/Rad50 complex that repairs DSB in DNA. p95 preferably has 100% amino acid sequence homology or identity to SEQ ID NO:2, or a biologically active subunit thereof. Moreover, it is envisioned that p95, or a subunit thereof, may comprise moieties other than the amino acid sequence having SEQ ID NO:2, e.g., amino acid residues not present in the native polypeptide (e.g., a fusion protein), nucleic acid molecules or targeting moieties such as antibodies or fragments thereof, so long as these moieties do not substantially reduce the biological activity of p95. A substantial reduction in activity means a reduction in activity of greater than about 50%.

A "variant" p95 is a polypeptide which has at least about 50%, preferably at least about 80%, and more preferably at least about 90%, but less than 100%, contiguous amino acid sequence homology or identity to the amino acid sequence corresponding to SEQ ID NO:2. Preferably, a variant polypeptide of the invention is biologically active. Thus, a variant p95 of the invention may include amino acid residues not present in SEQ ID NO:2, e.g., amino acid substitutions, and amino and/or carboxy, or internal, deletions or insertions, of amino acid residues relative to SEQ ID NO:2. Variant polypeptides of the invention can include polypeptides having at least one D-amino acid, as well as moieties other than the amino acid residues that correspond to SEQ ID NO:2, such as amino acid residues that form a part of a fusion protein, nucleic acid molecules or targeting moieties such as antibodies or fragments thereof, so long as these moieties do not substantially reduce the biological activity of a variant p95. p95 polypeptides or variants which are subjected to chemical modifications, such as esterification, amidation, reduction, protection and the like, are referred to as "derivatives."

Preferably, the polypeptides of the invention are "biologically active". A biologically active polypeptide of the invention has at least about 1%, more preferably at least about 10%, and more preferably at least about 50%, of the activity of a polypeptide having SEQ ID NO:2. The activity of a DNA repair polypeptide can be measured by methods well known to the art, some of which are described hereinbelow. The methods include DNA binding in vitro; DNA binding in cells as determined by nuclear focus formation or assessed by partial volume irradiation (see Example 1); physical association with the hMre11/hRad50 protein complex, as determined by biochemical or genetic means; or alteration in the nuclease activities mediated by the hMre11/hRad50 complex. A biologically active polypeptide of the invention also includes polypeptides that are immunogenic, i.e., they are useful to raise antisera specific for the immunogen.

A variant nucleic acid molecule of the invention has at least about 70%, preferably at least about 80%, and more preferably at least about 90%, but less than 100%, contiguous nucleotide sequence homology or identity to SEQ ID NO:1. A variant nucleic acid molecule of the invention may include nucleotide bases not present in SEQ ID NO:1, e.g., 5', 3' or internal deletions or insertions, such as the insertion of a restriction endonuclease recognition site.

A "recombinant" animal, e.g., a mouse, of the invention has a genome that has been manipulated in vitro so as to alter, e.g., decrease or disrupt, or, alternatively, increase, the function or activity of at least one copy of the p95 gene.

I. Identification of Nucleic Acid Molecules Falling within the Scope of the Invention A. Nucleic Acid Molecules of the Invention 1. Sources of the Nucleic Acid Molecules of the Invention Sources of nucleotide sequences from which the present nucleic acid molecules encoding p95, a subunit, a variant or the nucleic acid complement thereof, include total or polyA$^+$ RNA from any vertebrate, preferably mammalian, cellular source from which cDNAs can be derived by methods known in the art. Other sources of the DNA molecules of the invention include genomic libraries derived from any vertebrate cellular source.

2. Isolation of a Gene Encoding p95

A nucleic acid molecule encoding p95 can be identified and isolated using standard methods, as described by Sambrook et al., *Molecular Cloning A Laboratory Manual*, Cold Spring Harbor, N.Y. (1989). For example, reverse-transcriptase PCR (RT-PCR) can be employed to isolate and clone p95 cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other vertebrate, preferably mammalian, p95s. One primer is prepared which is predicted to anneal to the antisense strand, and another primer prepared which is predicted to anneal to the sense strand, of a DNA molecule which encodes p95.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode p95 is to screen a cDNA library. Screening for DNA fragments that encode all or a portion of a cDNA encoding p95 can be accomplished by probing the library with a probe which has sequences that are highly conserved between genes believed to be related to p95, e.g., the homolog of p95 from a different species, or by screening of plaques for binding to antibodies that specifically recognize p95 or by binding to proteins that interact with p95, e.g., mammalian, preferably human, Mre11/Rad50 complex. DNA fragments that bind to a probe having sequences which are related to p95, which are immunoreactive with antibodies to p95, or which bind to agents that specifically react with p95, can be subcloned into a suitable vector and sequenced and/or used as probes to identify other cDNAs encoding all or a portion of p95.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated, and/or expressed. For example, "isolated p95 nucleic acid" is RNA or DNA containing greater than 9, preferably 36, and more preferably 45 or more, sequential nucleotide bases that encode at least a portion of p95, or a variant thereof, or a RNA or DNA complementary thereto, that is complementary or hybridizes, respectively, to RNA or DNA encoding p95 and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated nucleic acid within the scope of the invention is RNA or DNA that encodes human p95 and shares at least about 80%, preferably at least about 90%, and more preferably at least about 95%, sequence identity with the polypeptide having SEQ ID NO:2, e.g., DNA corresponding to SEQ ID NO:1.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., Nucleic Acids Res., 9, 6103 (1981), and Goeddel et al., Nucleic Acids Res., 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3 Variants of the Nucleic Acid Molecules of the Invention

Nucleic acid molecules encoding amino acid sequence variants of p95 are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of p95.

Oligonucleotide-mediated mutagenesis is a preferred method for preparing amino acid substitution variants of p95. This technique is well known in the art as described by Adelman et al., DNA, 2, 183 (1983). Briefly, p95 DNA is altered by hybridizing an oligonucleotide encoding the desired mutation to a DNA template, where the template is the single-stranded form of a plasmid or bacteriophage containing the unaltered or native DNA sequence of p95. After hybridization, a DNA polymerase is used to synthesize an entire second complementary strand of the template that will thus incorporate the oligonucleotide primer, and will code for the selected alteration in the p95 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., Proc. Natl. Acad. Sci. U.S.A., 75, 5765 (1978).

The DNA template can be generated by those vectors that are either derived from bacteriophage M13 vectors (the commercially available M13 mp18 and M13mp19 vectors are suitable), or those vectors that contain a single-stranded phage origin of replication as described by Viera et al., Meth. Enzymol., 153, 3 (1987). Thus, the DNA that is to be mutated may be inserted into one of these vectors to generate single-stranded template. Production of the single-stranded template is described in Sections 4.21–4.41 of Sambrook et al., Molecular Cloning: A Laboratory Manual (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of p95, and the other strand (the original template) encodes the native, unaltered sequence of p95. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a DNA segment encoding SEQ ID NO:2, wherein the DNA segment comprises SEQ ID NO:1, or variants of SEQ ID NO:1, having nucleotide substitutions which are "silent" (see FIG. 12). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant of SEQ ID NO:1 at the twenty-second codon in the polypeptide (GTT in SEQ ID NO:1) includes the substitution of GTC, GTA or GTG for GTT. Other "silent" nucleotide substitutions in SEQ ID NO:1 which can encode SEQ ID NO:2 can be ascertained by reference to FIG. 12 and page D1 in Appendix D in Sambrook et al., *Molecular Cloning: A Laboratory Manual* (1989). Nucleotide substitutions can be introduced into DNA segments by methods well known to the art, to yield nucleic acid molecules of the invention having silent nucleotide substitutions, or to yield nucleic acid molecules having nucleotide substitutions that result in amino acid substitutions (see polypeptide variants hereinbelow).

II. Preparation of Molecules Useful to Practice the Methods of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding p95 is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species. In particular, a chimeric vector includes the linking of an open reading frame encoding at least a portion of p95, or a variant thereof, with another nucleic acid segment that encodes a peptide, e.g., GST or 6XHis, so as to encode a fusion polypeptide. The portion of the fusion polypeptide that is not p95 is useful to isolate the fusion polypeptide from other host cell polypeptides.

Aside from preselected DNA sequences that serve as transcription units for p95, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning A Laboratory Manual*, Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding p95 or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the p95 or its complement, which host cell may or may not express significant levels of autologous or "native" p95.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of p95, e.g., by immunological means (immunoprecipitations, immunoaffinity columns, ELISAs and Western blots) or by any other assay useful to identify molecules falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the peptide products of the introduced DNA sequences or evaluating the phenotypic changes brought about by the expression of the introduced DNA segment in the host cell.

B. Polypeptides

The present isolated, purified polypeptides, variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W.H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides and polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given p95 can be readily prepared. For example, amides of p95 or variants of the present invention may also be prepared by techniques well known in the art for converting a carboxylic acid group or precursor, to an amide. A preferred method for amide formation at the C-terminal carboxyl group is to cleave the peptide or polypeptide from a solid support with an appropriate amine, or to cleave in the presence of an alcohol, yielding an ester, followed by aminolysis with the desired amine.

Salts of carboxyl groups of p95 or a variant of the invention may be prepared in the usual manner by contacting the peptide or polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of p95 or variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. Formyl-methionine, pyroglutamine and trimethyl-alanine may be substituted at the N-terminal residue of the peptide or polypeptide. Other amino-terminal modifications include aminooxypentane modifications (see Simmons et al., *Science*, 276, 276 (1997)).

In addition, the amino acid sequence of p95 can be modified so as to result in a p95 variant. The modification includes the substitution of at least one amino acid residue in p95 for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, and tert-butylglycine.

One or more of the residues of the polypeptide can be altered, so long as the polypeptide variant is biologically active. It is preferred that the variant has at least about 10% of the biological activity of the corresponding non-variant polypeptide, e.g., a polypeptide having SEQ ID NO:2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 13 under the heading of exemplary substitutions. More preferred substitutions are under the heading of preferred substitutions. After the substitutions are introduced, the variants are screened for biological activity.

Amino acid substitutions falling within the scope of the invention are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptide variants with non-conservative substitutions. Non-conservative substitutions entail exchanging a member of one of the classes described above for another.

Acid addition salts of the polypeptide or variant polypeptide or of amino residues of the polypeptide or variant polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

C. Antibodies

The antibodies of the invention are prepared by using standard techniques. To prepare polyclonal antibodies or "antisera," an animal is inoculated with an antigen, i.e., a purified immunogenic p95 peptide or polypeptide, or a Mre11 peptide or polypeptide, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies against p95 or Mre11.

Following immunization, Ig is purified from the immunized bird or mammal, e.g., goat, rabbit, mouse, rat, or donkey and the like. For certain applications, particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to p95 or Mre11, or peptides thereof. Antibodies can be purified by affinity chromatography, using purified p95 or Mre11, or peptides thereof. Purification of antibodies by affinity chromatography is generally known to those skilled in the art (see, for example, U.S. Pat. No. 4,533,630). Briefly, the purified antibody is contacted with the purified p95 or Mre11, or peptide thereof, bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the F(ab) fragment scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

The antibodies of the invention are useful for detecting or determining the presence or amount of p95 or Mre11 polypeptide or protein in a sample, e.g., a physiological sample such as a mammalian tissue biopsy or a mammalian physiological fluid comprising cells, suspected of containing, or having reduced amounts of the polypeptide or protein. The antibodies are contacted with the sample for a period of time and under conditions sufficient for antibodies to bind to the polypeptide so as to form a binary complex between at least a portion of said antibodies and said polypeptide. Such times, conditions and reaction media can be readily determined by persons skilled in the art.

For example, the physiological sample which comprises cells may be obtained from a mammal, e.g., a human. The cells are lysed to yield an extract which comprises cellular proteins. Alternatively, intact cells, e.g., a tissue sample such as paraffin embedded and/or frozen sections of biopsies, are permeabilized in a manner which permits macromolecules, i.e., antibodies, to enter the cell. The antibodies of the invention are then incubated with the protein extract, e.g., in a Western blot, or permeabilized cells, e.g., prior to flow cytometry, so as to form a complex. The presence or amount of the complex is then determined or detected.

The antibodies of the invention may also be coupled to an insoluble or soluble substrate. Soluble substrates include proteins such as bovine serum albumin. Preferably, the antibodies are bound to an insoluble substrate, i.e., a solid support. The antibodies are bound to the support in an amount and manner that allows the antibodies to bind the polypeptide (ligand). The amount of the antibodies used relative to a given substrate depends upon the particular antibody being used, the particular substrate, and the binding efficiency of the antibody to the ligand. The antibodies may be bound to the substrate in any suitable manner. Covalent, noncovalent, or ionic binding may be used. Covalent binding can be accomplished by attaching the antibodies to reactive groups on the substrate directly or through a linking moiety.

The solid support may be any insoluble material to which the antibodies can be bound and which may be conveniently used in an assay of the invention. Such solid supports include permeable and semipermeable membranes, glass beads, plastic beads, latex beads, plastic microtiter wells or tubes, agarose or dextran particles, sepharose, and diatomaceous earth. Alternatively, the antibodies may be bound to any porous or liquid permeable material, such as a fibrous (paper, felt etc.) strip or sheet, or a screen or net. A binder may be used as long as it does not interfere with the ability of the antibodies to bind the ligands.

The invention also comprises reagents and kits for detecting the presence or amount of p95 or Mre11 in a sample. Preferably, the reagent or kit comprises the purified antibodies of the invention in a liquid that does not adversely affect the activity of the antibodies in the intended assay. Preferably, the liquid is saline solution. Alternatively, the reagent or kit may comprise the purified antibodies attached to a substrate as discussed above. Preferably, the substrate is an insoluble solid support, e.g., the well of a microtiter plate. An alternative preferred substrate is solid particles, most preferably latex beads.

The diagnostic kit comprises, in a container or packaging, one or more of the reagents of the invention and a means for detecting or measuring the formation of complexes created by the binding of polypeptide and the antibodies in the reagents. The detecting or measuring means is preferably an immunoassay, such radioimmunoassay, enzyme-linked immunosorbent assay (ELISA), or an immunofluorescence assay. Most preferably, the detecting or measuring means is a reagent capable of binding to the complexes formed by p95 or Mre11 and the antibodies and containing a detectable moiety. Such reagent may be the antibody of the invention conjugated with a detectable moiety. Alternatively, the antibody can be a second antibody, which is an antibody which binds to the antibodies of the invention, conjugated to a detectable moiety.

III. Transgenic and Recombinant Mice of the Invention

Trangenic mice and knock-out mice can be prepared by methods known to the art, see for example, Wagner et al. (U.S. Pat. No. 4,873,191), Neve (U.S. Pat. No. 5,672,805), Cordell et al. (U.S. Pat. No. 5,387,742), Brandon et al. (*Curr. Biol.*, 5, 758 (1995)), Gallafin et al. (U.S. Pat. No. 5,728, 533), Weintrab et al. (U.S. Pat. No. 5,695,995), Capecchi (*Science*, 244, 1288 (1989)), Li et al. (*Cell*, 80, 401 (1995)), Brandon et al. (*Curr. Biol.*, 5, 625 (1995)), Devries et al. (*Sem. in Cancer Biol.*, 7, 229 (1996)), Deng et al. (*Mol. Cell Biol.*, 13, 2134 (1993)), Majzoub et al. (*NEJM*, 334, 904 (1996)), Allemand et al. (*Biochimie*, 77, 826 (1995)), and Rosenberg (*Mol. Carcinogenesis*, 20, 262 (1997)), WO 98/03059, and WO 97/46669, the disclosures of which are incorporated by reference herein.

To prepare p95 knock-out mice, a targeting vector is constructed. For example, a targeting vector was constructed that deletes the 160 bp fourth exon of the murine NBS gene, which results in a frameshift mutation. This mutation is analogous to the most common nbs1 allele in NBS patients which creates a frameshift in exon six, and results in a complete lack of p95 protein. Homologous integration of the targeting construct replaces exon 4 of the mouse gene with the puromycin or neomycin phosphotransferase cassette under the control of the PGK promoter. The construct contains 5 kb of homology on the right arm, and 3.7 kb of homology on the left arm. In addition, a HSV thymidine kinase gene is situated at the left end of the construct so the non-homologous integrants can be selected against with gancyclovir. This construct efficiently disrupted the mouse locus, with a targeting frequency of at least 5%. It is envisioned that other targeting vectors may also be employed so as to result in disruption of the NBS gene. Therefore, murine cells and mice carrying the targeted mutation will be deficient in, and preferably completely lacking, p95.

IV. Identification of Agents that Alter p95 Expression or Activity

Agents that increase or decrease native p95 activity or expression may be identified using in vitro assays. For example, cells with wild-type p95 activity, or NBS cells, are stably transfected with recombinant plasmids that express p95. The resulting cell lines are then contacted with an agent and the amount or activity of p95 in the presence of the agent relative to cells not exposed to the agent is determined, and/or relative to non-transfected cells, using methods described herein. Moreover, direct interaction of an agent with p95 may be determined by binding assays utilizing purified, recombinant p95 polypeptide and labeled agent, or labeled p95 and the agent.

Agents that decrease or inhibit p95 activity or function are particularly useful in therapeutic methods which target tumor cells. Thus, targeting can result in an increased concentration of the agent at a specific anatomic location or cell type. Moreover, the linking of the agent to a targeting or binding moiety may increase the stability of the agent in vivo. For example, an inhibitor of p95 is linked to a moiety that targets tumor cells, e.g., an antibody or a fragment thereof that specifically binds to a cell surface antigen expressed on tumor cells, preferably an antigen that is exclusively expressed on tumor cells. The inhibitor and the targeting moiety may be either covalently or non-covalently linked. If the inhibitor and the targeting moiety are peptides or polypeptides, the covalent linkage may be via peptide bonds, e.g., via expression of a fusion polypeptide. Preferably, the targeting moiety is an antibody or a fragment thereof, e.g., NR-LU-10 (anti-carcinoma), NR-ML-5 (anti-melanoma) or anti-CO$_{45}$ (anti-lymphoma) antibodies.

To prepare immunoconjugates useful for targeting a malignant cell, an antibody or fragment thereof having a specificity for a surface antigen on a malignant cell is attached to an agent that effects the activity of p95. Preferably, the agent is attached via peptide bonds to the carboxy termini regions, e.g., CH3, of antibody heavy chains. More preferably, the agent is a peptide or polypeptide. Such immunoconjugates can be prepared by genetic engineering techniques, i.e., by forming a nucleic acid construct encoding the chimeric immunoconjugate. Preferably, the gene construct encoding the immunoconjugate includes, in 5' to 3' orientation, a DNA segment which encodes a heavy chain variable region, a DNA segment encoding the heavy chain constant region, and a DNA segment coding for the agent. The fused gene is inserted into an expression vector for transfection of the appropriate recipient cells where it is expressed. The hybrid chain can be combined with a light (or heavy) chain counterpart to form monovalent and divalent immunoconjugates.

The heavy chain constant region for the conjugates can be selected from any of the five isotypes: alpha, delta, epsilon, gamma or mu. Heavy chains or various subclasses (such as the IgG subclasses 1–4) can be used. The light chains can have either a kappa or lambda constant chain. DNA sequences for these immunoglobulin regions are well known in the art (see, e.g., Gillies et al., *J. Immunol., Meth.,* 125, 191 (1989)).

In preferred embodiments, the variable region is derived from an antibody specific for the target antigen (an antigen associated with a diseased cell such as a cancer cell), and the constant region includes the CH1, CH2 and CH3 domains. The gene encoding the agent is joined, e.g., by appropriate linkers, e.g., by DNA encoding (Gly$_4$-Ser)$_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the agent, can be designed to provide for proteolytic release of the agent at the target site. For example, it is well known that plasmin and trypsin cleave after lysine and arginine residues at sites that are accessible to the proteases. Many other site-specific endoproteases and the amino acid sequences they attack are well known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

Genes encoding appropriate variable regions can be obtained generally from Ig-producing lymphoid cells. For example, hybridoma cell lines producing Ig specific for tumor associated antigens can be produced by standard somatic cell hybridization techniques. These Ig-producing cell lines provide the source of variable region genes in functionally rearranged form. The variable region genes are typically of murine origin because the murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate polypeptide. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion (see Gillies et al., *Biotechnol.*, 7, 798–804 (1989)). Alternative methods include electroporation or calcium phosphate precipitation.

Other useful methods of producing the immunoconjugates include the preparation of an RNA sequence encoding the construct and its translation in an appropriate in vivo or in vitro system.

Methods for purifying recombinant immunoglobulins are well known. For example, a well known method of purifying antibodies involves protein A purification because of the propensity of protein A to bind the Fc region of antibodies. The antigen binding activity of the purified immunoconjugates can then be measured by methods well known to the art, such as described in Gillies et al. (*J. Immunol. Methol.*, 125, 191 (1989)). For example, immunoconjugate activity can be determined using antigen-coated plates in either a direct binding or competition assay format.

In particular, it is preferred that humanized antibodies are prepared and then assayed for their ability to bind antigen. Methods to determine the ability of the humanized antibodies to bind antigen may be accomplished by any of numerous known methods for assaying antigen-antibody affinity. For example, the murine antibody NR-LU-13 binds an approximately 40 kilodalton glycoprotein expressed on numerous carcinomas. This antigen has been characterized in Varki et al., *Cancer Res*, 44, 681 (1984); Okabe et al., *Cancer Res.*, 44, 5273 (1989). Thus, it is routine to test the ability of humanized antibodies to bind the NR-LU-13 antigen. Moreover, methods for evaluating the ability of antibodies to bind to epitopes of this antigen are known.

Humanized antibodies (or fragments thereof) are useful tools in methods for therapeutic purposes. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies can be found, for example, in U.S. Pat. Nos. 4,877,868, 5,175,343, 5,213,787, 5,120,526, and 5,202,169.

It will be recognized that the inventors also contemplate the utility of human monoclonal antibodies or "humanized" murine antibodies in therapeutic conjugates. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 0,411,893 A2. Humanized binding partners will be recognized to have the advantage of decreasing the immunoreactivity of the antibody or polypeptide in the host recipient, which may thereby be useful for increasing the in vivo half-life and reducing the possibility of adverse immune reactions. See also, N. Lonberg et al. (U.S. Pat. Nos. 5,625,126; 5,545,806; and 5,569,825); and Surani et al. (U.S. Pat. No. 5,545,807).

Useful binding peptides for cancer treatment embodiments of the present invention include those associated with cell membrane and cytoplasmic epitopes of cancer cells and the like. These binding peptides localize to the surface membrane of intact cells and internal epitopes of disrupted cells, respectively, and deliver the therapeutic agent for assimilation into the target cells. Minimal peptides, mimetic organic compounds and human or humanized antibodies that localize to the requisite tumor cell types are also useful as binding peptides of the present invention. Such binding peptides may be identified and constructed or isolated in accordance with known techniques.

Other methods useful to prepare conjugates are well known to the art. See, for example U.S. Pat. No. 5,650,150, the disclosure of which is incorporated by reference herein. Representative "coupling" methods for linking the agent through covalent or non-covalent bonds to the targeting moiety include chemical cross-linkers and heterobifunctional cross-linking compounds (i.e., "linkers") that react to form a bond between reactive groups (such as hydroxyl, amino, amido, or sulfhydryl groups) in an agent and other reactive groups (of a similar nature) in the targeting moiety. This bond may be, for example, a peptide bond, disulfide bond, thioester bond, amide bond, thioether bond, and the like. In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr, *J. of Immunol.* 133:i–vii, 1984). In another illustrative example where the conjugate contains a radionuclide cytostatic agent, U.S. Pat. No. 4,897,255, Fritzberg et al., incorporated herein by reference, is instructive of coupling methods that may be useful. In one embodiment, the conjugate contains a polypeptide targeting moiety coupled covalently to polypeptide inhibitor of p95. In this case, the covalent bond of the linkage may be formed between one or more amino, sulfhydryl, or carboxyl groups of the binding protein and the agent.

V. Dosages, Formulations and Routes of Administration of the Agents of the Invention The polypeptides of the invention may be administered at dosages of at least about 0.001 to about 100 mg/kg, more preferably about 0.01 to about 10 mg/kg, and even more preferably about 0.1 to about 10 mg/kg, of body weight, although other dosages may provide beneficial results. The amount administered will vary depending on various factors including, but not limited to, the agent chosen, the disease or condition, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556), or the administration of the nucleic acid molecule itself (see, for example, Felgner et al., U.S. Pat. No. 5,580,859, Pardoll et al., *Immunity*, 3, 165 (1995); Stevenson et al., *Immunol. Rev*, 145, 211 (1995); Molling, *J. Mol. Med.*, 75, 242 (1997); Donnelly et al., *Ann. N.Y. Acad. Sci.*, 722, 40 (1995); Yang et al., *Mol. Med. Today*, 2, 476 (1996); Abdallah et al., *Biol. Cell*, 85, 1 (1995)), or the nucleic acid molecule introduced into a viral vector or liposomes. Pharmaceutical formulations, dosages and routes of administration for nucleic acids are generally disclosed, for example, in Felgner et al., supra.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. When the agents of the invention are employed for prophylactic purposes, agents of the invention are amenable to chronic use, preferably by systemic administration.

One or more suitable unit dosage forms comprising the therapeutic agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other therapeutic agents, for example, bronchodilators.

The invention will be further described by, but is not limited to, the following examples.

EXAMPLE 1 hMre11 and hRad50 Nuclear Foci are Induced During the Response to DNA Double Strand Breaks Materials an Methods Cell lines, IMR90 primary diploid fibroblasts were obtained from the American Type Culture Collection and were used at passages 10 to 15, with equivalent results. 37Lu primary fibroblasts were also obtained from the American Type Culture collection and used at passages 3 to 7. 180BR primary fibroblasts were obtained from C. Arlett and were used at passages 8 to 13. GM00637G normal simian virus 40 (SV40)-transformed fibroblasts and the SV40-transformed ataxia-telangiectasia (AT) cell lines GM09607A and GM05849B were obtained from the Cornell Institute for Medical Research. M059J and M059K cells were obtained from M. J. Allalunis-Turner. Primary fibroblasts were grown in Dulbecco modified Eagle medium with 10% fetal calf serum (FCS), and SV40-transformed fibroblasts were grown in Dulbecco modified Eagle medium with 5% FCS and 5% Cosmic Calf serum (Hyclone, Logan, Utah). K562 CML cells (provided by Peggy Farnham) were grown in RPMI 1640 having 10% Cosmic Calf serum, 1% Pen-Strep and 2 mM L-glutamine. All cells were maintained at 37° C. in a 5% $CO_2$, 95% air humidified environment. All cells routinely tested negative for mycoplasmas with the MycoTect kit (Gibco, Grand Island, N.Y.).

Irradiation and drug treatment. Cells were irradiated in a Mark I$^{137}$ Cs source at a dose rate of approximately 2.5 Gy/minute. UV irradiation was done in a UV cross-linking instrument (Stratagene, La Jolla, Calif.). For drug treatment, cells were exposed to etoposide dissolved as a 50% solution in dimethyl sulfoxide (DMSO) or an equivalent amount of DMSO alone (both from Sigma, St. Louis, Mo.) in growth medium for 1 hour and then washed twice with phosphate-buffered saline (PBS) before replacement with drug-free medium.

Cell cycle analysis. Cell cycle analysis was performed with slight modifications to retain apoptotic cells. Log-phase cells grown on 60 mm diameter dishes were either untreated (t=0 hour) or irradiated and fixed at various time points after irradiation. Cells were trypsinized, collected along with the used medium, and washed once in PBS. The resulting cell pellet was suspended in 100 µl of 150 mM NaCl-10 mM Tris-HCl (pH 7.0) to which 900 µl of ice-cold 95% ethanol was added dropwise. Fixed cells were stored at 4° C. at least overnight, pelleted, and washed in phosphate-citrate buffer (192 mM $Na_2HPO_4$, 4 mM $Na_3C_6H_5O_7$). The final washed pellet was stained in a solution containing 33 µg of propidium iodide per ml, 0.3 mg of RNase A per ml, and 0.2% Nonidet P-40 in PBS. Cell cycle analysis was performed on an EPICS Profile II flow cytometer (Coulter, Miami, Fla.).

Antibodies. Affinity purification of hMre11 and hRad50 rabbit antisera has been described previously (Dolganov et al., 1996). The fluorescent dye Texas Red was directly conjugated to affinity-purified anti-hMre11 by using a Fluoreporter kit (Molecular Probes, Eugene, Ore.). Rabbit antiserum directed against hRad51 was provided by Charles Radding (Yale University).

Immunofluorescence. Fibroblasts were seeded on Teflon-coated six-well slides (Cel-Line Associates, Newfield, N.J.)

and allowed to adhere for at least 2 days prior to each experiment. Cells were irradiated or drug treated on slides, fixed at various time points in ice-cold methanol for 20 minutes at −20° C., and then permeabilized in ice-cold acetone for 10 seconds. Following fixation, slides were washed three times for 5 minutes each in PBS and blocked in 10% FCS-PBS for 1 hour at room temperature. Slides were incubated for 1 hour at 37° C. with hMre11 (1:150 dilution), hRad50 (1:150 dilution), or hRad51 (1:400 dilution) primary rabbit antiserum, followed by fluorescein isothiocyanate (FITC)-conjugated goat anti-rabbit secondary antiserum (1:200 dilution) (Pierce, Rockford, Ill.) for 1 hour at 37° C. All antisera were diluted in 1% bovine serum albumin in PBS. Slides were counterstained with 0.1 μg of DAPI (4', 6-diamidino-2-phenylindole) per ml for 1 minute, mounted in antifade solution (2.3% DABCO (1,4-diazabicyclo[2.2.2]octane), 0.1 M Tris-HCl (pH 8.0), 90% glycerol), and viewed via epifluorescence microscopy. After each blocking or antibody incubation step described above, slides were washed in PBS three times for 5 minutes.

For studies involving Texas Red-conjugated anti-hMre11, detection was performed as described above, followed by a 1 hour blocking step as described above with the addition of a 1:100 dilution of rabbit serum. The slides were washed with PBS and incubated with Texas Red-conjugated anti-hMre11 (diluted 1:200) prior to counterstaining and mounting as described above. Differential staining observed with hRad50 and hRad51 antisera in combination with the Texas Red-conjugated hMre11 antiserum (see below) demonstrates the specificity of this staining method.

IRIF quantification and image capture. Foci were scored by eye at a magnification of ×600. At least 200 nuclei per time point were examined for each antiserum. A nucleus was considered positive for hMre11 or hRad50 IRIF if it contained at least five discernible foci. Nuclei containing fewer than five foci were scored as negative; positive nuclei were further categorized as those with 5 to 20 foci or >20 foci. Positive nuclei were categorized as having 5 to 30 foci or >30 foci. For hRad51, a nucleus was considered positive if it contained at least 10 foci. Nuclear antibody staining was confirmed in each case with DAPI. Images were captured by using a cooled charge-coupled device (CCD) camera (Princeton Instruments, Trenton, N.J.) and grayscale images were processed by using Photoshop 4.0 (Adobe, San Jose, Calif.). Although images were captured with a CCD camera, all foci were readily observable by eye.

Comet assays. Cells were treated with etoposide or DMSO or were irradiated with 12 Gy or mock irradiated, trypsinized, and embedded in 1.5 ml of 1% agarose to yield a final density of approximately $10^4$ cells/slide. Neutral comet assays were then performed (Olive et al., 1991). Comets were viewed under a final magnification of ×400, and images were captured with a CCD camera. Percent DSBs remaining was calculated from tail moment values by using the formula (tail moment at 8 hours−control tail moment) (initial tail moment−control tail moment)×100.

Immunoblotting, immunoprecipitation, and metabolic labeling. Immunoblot analyses with hMre11 and hRad50 antisera were carried out as described previously (Dolganov et al., 1996). For metabolic labeling, irradiated (12 Gy) and mock-irradiated cells were labeled at 2 hours postirradiation with 80 μCi of [$^{35}$S]methionine (EasyTag; NEN, Boston, Mass.) per ml for 6 hours longer and then harvested for immunoprecipitation analyses as described previously (Dolganov et al., 1996). Immunoprecipitates were fractionated on sodium dodecyl sulfate/7% polyacrylamide gels. Gels were then fixed for 20 minutes in 30% methanol/10% acetic acid, incubated in 1 M Na salicylate for 20 minutes, and autoradiographed at −80° C. Autoradiograms were scanned and processed as described by Dolganov et al., 1996.

Results hMre11 and hRad50 form nuclear foci in response to ionizing radiation. To investigate whether ionizing radiation induced alterations in the subcellular distribution of hMre11 and hRad50 in the human fibroblast cell line IMR90, immunofluorescence methodologies were employed. Both hMre11 and hRad50 are abundant proteins that are uniformly distributed in the nuclei of unirradiated cells, with the exception of nucleoli. Following gamma irradiation, both hMre11 and hRad50 formed discrete nuclear foci, which are referred to as IRIF. Nuclear fluorescence was not observed in cells stained either with preimmune serum or with hMre11 antiserum that had been previously incubated with bacterially produced hMre11 protein. DAPI counterstaining of irradiated cells indicated that IRIF-containing nuclei were not grossly aberrant and did not show signs of apoptosis. Flow cytometric analyses of IMR90 cultures irradiated in parallel did not detect a significant population of apoptotic cells.

hMre11 and hRad50 IRIF formation was also observed in the primary fibroblast cell line 37Lu, the glioblastoma cell lines M059J and M059K, HeLa cells, and the SV40-transformed fibroblast cell line GM637.

hMre11 and hRad50 IRIF colocalize. Immunofluorescence was employed to determine whether hMre11 and hRad50 IRIF colocalize. Immunofluorescence analysis of irradiated 180BR fibroblasts was performed with anti-hRad50 antiserum followed by FITC-conjugated goat anti-rabbit anti-serum to detect bound antibody. Slides were washed, treated with blocking solution, and stained with Texas Red-conjugated anti-hMre11 antiserum. Images of nuclei were first captured with FITC filters (hRad50), and then images of the same nuclei were captured with the Texas Red (hMre11) and DAPI (chromatin) filter sets. Merging of the three images revealed that hMre11 and hRad50 IRIF colocalize within the nucleus. Colocalization of hMre11 and hRad50 IRIF has also been observed in IMR90 and 37Lu fibroblasts.

The human Rad51 homolog, hRad51, has also been shown to form nuclear foci following DNA damage. It was determined that hMre11 and hRad51 IRIF do not colocalize. Irradiated IMR90 fibroblasts were stained with anti-hRad51 antiserum and Texas Red-conjugated anti-hMre11 antiserum, as described above. Contrary to the results obtained with anti-hRad50 and Texas Red-conjugated anti-hMre11 antisera, distinct localization patterns for hRad51 and hMre11 nuclear foci were observed. Nuclei that contain hRad51 foci did not contain hMre11 IRIF. Conversely, nuclei positive for hMre11 IRIF did not contain hRad51 foci. In two independent experiments (792 nuclei examined), 123 nuclei were hRad51 IRIF positive, 236 nuclei were hMre11 IRIF positive, and none were positive for both types of IRIF. Therefore, irradiated fibroblasts that contained nuclear foci were positive for either hMre11 foci or hRad51 foci, but not both.

hMre11 and hRad50 IRIF are specific to DNA DSBs and form in a dose-dependent manner. Based on the involvement of yeast Mre11 and Rad50 in DSB repair and the lack of hMre11-hRad50 foci in unirradiated cells, it was postulated that hMre11 and hRad50 IRIF were formed specifically in response to ionizing-radiation-induced DNA DSBs. Ionizing radiation has been shown to induce DNA DSBs in a dose-dependent, linear fashion. To examine the dose dependence of hMre11-hRad50 IRIF formation in IMR90 cells, cells were irradiated with 4, 8, or 12 Gy and evaluated at 8 hours postirradiation. Nuclei were then scored for the number of observed hMre11 IRIF and placed in three categories: less than 5 (negative), 5 to 20, or >20 IRIF per nucleus. It was found that the mean number of IRIF in the 5-to-20 class increased with the radiation dose, as did the number of nuclei that fell into the >20 class. An average of 6 IRIF per positive nucleus were observed at a dose of 4 Gy, and this increased to an average of over 12 IRIF per positive nucleus after 12 Gy. The percentage of nuclei that contained hMre11 IRIF also increased with the dose, from less than 10% after 4 Gy to over 50% after 12 Gy.

The response of hMre11 and hRad50 to other DNA-damaging agents to define the types of lesions that lead to IRIF formation was analyzed. IMR90 fibroblasts were treated with the topoisomerase II inhibitor etoposide, a potent inducer of DNA DSBs. Etoposide treatment (1001 g/ml) induced the formation of hMre11 foci indistinguishable from IRIF; 28% of nuclei examined were positive for foci at 8 hours post-treatment. Control cells treated with DMSO alone did not exhibit foci. The neutral comet assay was used to show that this etoposide dose induced DNA DSBs and that 69% of these breaks remained unrepaired at 8 hours post-treatment. In contrast to ionizing radiation and etoposide treatment, no hMre11 or hRad50 foci were observed following UV irradiation at a dose of 16 J/m$^2$. This evidence suggests that hMre11-hRad50 IRIF form specifically in response to DNA DSBs.

The time course of IRIF formation following exposure to ionizing radiation was determined. Log-phase IMR90 fibroblasts were irradiated with 12 Gy and fixed at 4, 8, and 24 hours postirradiation. Independent slides were stained for hMre11 or hRad50. The percentage of nuclei with hMre11 and hRad50 IRIF increased to a maximum of greater than 60% at 8 hours postirradiation, with a subsequent decrease in the percentage of IRIF-positive cells by 24 hours. Similar kinetics have been observed in other DSB repair-proficient cells (see below). Thirty-two percent of nuclei were positive for hRad51 foci at 4 and 8 hours. These results were similar to those reported previously (Haaf et al., 1995) but distinct from those for hMre11 and hRad50.

The hMre11-hRad50 IRIF response is altered in DNA DSB repair-deficient and cell cycle checkpoint mutant cells. The cell line 180BR is acutely sensitive to the effects of ionizing radiation (Badie et al., 1995b). Due to a defect in the ability to repair DNA DSBs, the half-life of DSBs is extended in 180BR relative to that in repair-proficient cells (Badie et al., 1995a). Thus, it was of interest to determine whether hMre11 and hRad50 IRIF formation was altered in these cells and whether the persistence of DNA DSBs in this cell line would alter the hMre11-hRad50 IRIF response. The multiplicity of IRIF in 180BR cells was increased for both hMre11 and hRad50, as measured by the number of IRIF observed in positive nuclei. Whereas only 12% of IMR90 cells that were positive for IRIF at 8 hours after 12 Gy had greater than 30 foci per positive nucleus, 77% of 180BR cells at the equivalent time and dose exhibited greater than 30 foci per positive nucleus. Neutral comet assays carried out on irradiated 180BR cells confirmed that the majority of initial DSBs were unrepaired at 8 hours postirradiation. In contrast, greater than 90% of the initial DSBs were repaired by 8 hours in IMR90 fibroblasts. Immunoblotting and immunoprecipitation analyses revealed that hMre11 and hRad50 expression and interaction appeared normal in 180BR cells and were unchanged with ionizing radiation. Consistent with the previously observed exclusivity of hMre11-hRad50 and hRad51 IRIF formation, the percentage of hRad51 IRIF-positive nuclei was reduced in 180BR relative to that in IMR90.

Cells from AT patients have mutations in the ATM gene, which encodes a PI-3-like protein kinase. ATM mutant cells do not appear to be DSB repair deficient per se; rather, they appear to be deficient in signaling the presence of DNA damage. As a result, AT cells exhibit radioresistant DNA synthesis and are sensitive to killing by ionizing radiation. To examine the dependence of hMre11 and hRad50 IRIF formation on the ATM-controlled response to DNA damage, the kinetics of hMre11 and hRad50 IRIF formation in two SV40-transformed AT cell lines, GM5849 and GM9607, was compared to those in the SV40-transformed normal human cell line GM637. When stained independently for either hMre11 or hRad50, IRIF-positive nuclei were observed in 25% of the GM637 cells examined at 10 hours after 12 Gy, whereas the hMre11 and hRad50 response in both AT cell lines was drastically reduced. No more than 4% of nuclei were positive for hRad50 IRIF at any time in either AT cell line tested. For hMre11, a maximum of 6.8% of nuclei that contained hMre11 IRIF in GM5849 was observed. In GM9607, the percentage of hMre11 IRIF-positive nuclei was similar to that in GM637, but the GM9607 hMre11 foci were atypical in size and fluorescence intensity. This difference presumably reflects the absence of hRad50 in the hMre11 IRIF. Importantly, hRad50 and hMre11 are present at normal levels in GM9607, and their abundance is unaffected by irradiation. In addition, irradiation does not induce alteration of the apparent stoichiometry of the hMre11-hRad50 complex. Approximately 47% of the initial DSBs were unrepaired in irradiated GM9607 cells, compared to less than 1% unrepaired DSBs in irradiated GM637 control cells.

Since the AT cell lines examined were deficient in the hMre11-hRad50 IRIF response, it was unclear whether AT cells were also deficient in the hRad51 focus-forming response to ionizing radiation. Anti-hRad51 antiserum was used to examine the kinetics of hRad51 focus formation in AT cells. GM637 cells exhibited a normal hRad51 response following gamma irradiation. At 24 hours postirradiation, only 10% of GM637 cells were positive for hRad51 foci. However, in contrast to hMre11 and hRad50 IRIF formation, 45 and 75% of the GM5849 and GM9607 AT cells, respectively, were positive for hRad51 at 24 hours. hRad51 protein levels are increased in SV40-transformed normal and AT cells relative to those in 180BR and IMR90 primary fibroblasts, but the abundance of hRad51 in GM637 and GM9607 cells is unaffected by irradiation. Flow cytometry profiles indicated that the majority of AT cells had accumulated in G$_2$/M at 24 hours following irradiation, as observed previously (Ford et al., 1984). Thus, AT cells failed to respond to ionizing radiation with hMre11-hRad50 foci but maintained a distinct and elevated hRad51 IRIF response.

Discussion

Immunofluorescence analysis in situ offers a way to correlate various metabolic processes with the locations of specific proteins and has provided evidence that certain functions may be regulated by their association with particular sites or structures within the nucleus. Immunofluorescence has been used to describe compartmentalization of nuclear proteins of unknown function into novel focal structures (e.g., PML; polymorphic interphase karyosomal association [PIKA]) and has provided evidence that diverse processes, including DNA replication, RNA splicing, and DNA repair, may be compartmentalized within the nucleus.

This experimental approach has also uncovered previously unsuspected roles for certain proteins, such as BRCA1, ATM, and ATR, in meiosis.

In this study, immunofluorescence was used to describe the redistribution of hMre11 and hRad50 to discrete foci within the nucleus following DNA damage. hRad50 and hMre11 steady-state protein levels were not altered following ionizing radiation or by changes in cell cycle position. Therefore, IRIF formation results from changes in the location rather than the abundance of hMre11 or hRad50. The hMre11-hRad50 IRIF response is a dose-dependent, dynamic process. hMre11 and hRad50 IRIF colocalize, whereas hMre11 and hRad51 foci do not, supporting genetic evidence of their independent roles in DSB repair. The formation of hRad50-hMre11 and hRad51 foci is altered in cell lines deficient in the cellular response to DNA damage. These studies suggest that the localization of recombinational DNA repair proteins to discrete nuclear foci is part of the normal DNA damage response.

IRIF formation is dependent upon DSBs. hMre11-hRad50 foci are specifically induced by DNA DSB-inducing agents. The induction of DNA DSBs by ionizing radiation is linearly dependent upon the radiation dose. The number of IRIF per nucleus also increases with dose, indicating that the number of DNA DSBs initially formed determines the multiplicity of the hMre11-hRad50 IRIF response. Treatment with etoposide, which induces DNA DSBs by trapping topoisomerase II complexes, also induced hMre11 foci. Etoposide preferentially induces damage in S and $G_2$, presumably due to higher expression of topoisomerase II during the S and $G_2$ phases. The number of hMre11 focus-positive nuclei following etoposide treatment corresponded approximately to the percentage of S- and $G_2$-phase cells in log-phase IMR90 fibroblasts. These observations support the interpretation that IRIF formation is dependent upon the induction of DSBs.

This assertion is further supported by the hMre11-hRad50 IRIF response in the DSB repair-deficient cell line 180BR. Ionizing radiation-induced DSBs in 180BR cells are 6- to 10-fold longer lived than those in normal cells, and these cells are extremely sensitive to the induction of chromosome aberrations by ionizing radiation ($\geq 45\%$ aberrant metaphases induced by 2 Gy). The molecular defect in this cell line is unknown; however, hMre11 and hRad50 expression and interaction are unaltered in 180BR cells. The persistence of unrepaired DSBs in 180BR cells at the time point examined (8 hours) thus results in greater numbers of hMre11-hRad50 IRIF in these cells. Together, these results are consistent with the hypothesis that hMre11-hRad50 foci form following the induction of DSBs and argue that focus formation reflects hMre11-hRad50 function in the normal cellular response to DSBs.

Independent formation of hMre11-hRad50 and hRad51 IRIF. Genetic analyses with *S. cerevisiae* indicate that there is minimal functional overlap in the proteins that mediate homologous recombination (e.g., Rad51) and nonhomologous end joining (e.g., hMre11 and Rad50). Colocalization of hMre11 and hRad50 IRIF is consistent with the idea that hMre11 and hRad50 function together in a protein complex during DSB repair. hMre11 (and therefore hRad50) IRIF form independently of hRad51 IRIF, consistent with the finding that hRad51 is not coimmunoprecipitable with the hMre11-hRad50 complex. Further supporting the functional distinction between hRad51 and hMre11-hRad50 is that hRad51 forms nuclear foci in undamaged cells in the S phase of the cell cycle, whereas hMre11-hRad50 foci form only in response to DNA damage. Thus, the focus-forming response of these DSB repair proteins confirms the expectation from *S. cerevisiae* that hMre11-hRad50 and hRad51 mediate distinct functions in DNA metabolism and repair.

IRIF formation is not uniform in the irradiated population. hMre11-hRad50 and hRad51 IRIF do not form in the same nuclei, indicating that a given cell in the irradiated population is competent to form only one class of focus. This result may suggest that a given irradiated cell is restricted to either homologous recombination or nonhomologous end joining for the repair of DSBs. hMre11-hRad50 or hRad51 IRIF formation may be governed by cell cycle status. Analysis of DSB repair-deficient rodent cells demonstrate the existence of distinct, cell cycle-specific pathways of DSB repair. Further, the requirement for a sister chromatid in homologous recombination suggests that this mode of DSB repair would be preferentially utilized in $S/G_2$. Asynchronous fibroblast cultures were employed. The maximal percentage of hMre11 and hRad50 IRIF-positive cells roughly corresponds to the percentage of cells in $G_1$ at the time of irradiation. Similarly, the percentage of cells in which hRad51 foci are observed roughly corresponds to the initial $G_2$ population. This correlation is supported by the observation that hRad51 expression is restricted to the S and $G_2$ phases of the cell cycle. Furthermore, recent work has demonstrated that synchronized CHO cells irradiated in $G_1$ do not form hRad51 IRIF.

The formation of hMre11-hRad50 versus hRad51 foci also appears to be governed by other factors. The percentage of hMre11-hRad50 IRIF-positive nuclei increases as a function of dose. Dose dependence has similarly been observed for hRad51 foci. Thus, IRIF formation depends upon the initial state of the cell, as well as a state that is induced by DNA damage in a dose-dependent fashion.

IRIF formation is altered in AT cells. The ATM gene encodes a PI-3-like protein kinase that mediates signal transduction functions upstream of p53 in the DNA damage response. Loss of ATM signaling function in AT cells impairs cell cycle checkpoint regulation and leads to ionizing radiation sensitivity. The radiosensitivity of AT cells cannot be attributed solely to the lack of checkpoint regulation; increased chromosomal damage is observed in cells held in $G_0/G_1$, and chemically induced cell cycle arrest fails to mitigate the ionizing radiation sensitivity of AT cells. These data suggest that ATM controls the processing of chromosomal damage in parallel with its function(s) in cell cycle regulation. In this study, it was shown that hMre11 and hRad59 IRIF formation is markedly reduced in both AT mutant cell lines tested but that the hRad51 IRIF response is highly elevated. Both homologous recombination and non-homologous end joining are utilized in mammalian DSB repair. If signaling by ATM is important for the function of the hMre11-hRad50 protein complex in the repair of chromosomal damage, the dramatically increased hRad51 response may indicate that DSBs normally repaired by the hMre11-hRad50 protein complex must be repaired by homologous recombination in AT cells. Interestingly, the spontaneous rate of homologous recombination in AT cells appears to be significantly increased. The data presented here support the hypothesis that the increased sensitivity of AT cells to cell killing and induction of chromosome aberrations following ionizing radiation treatment is at least partially attributable to misregulation of DSB repair processes.

In this regard, it is important that hMre11-hRad50 and hRad51 IRIF are not dependent on p53, as IRIF form in cells with virally inactivated p53. This implies a direct link between DSB repair and the ATM signaling pathway that is upstream of p53 cell cycle checkpoint functions. The existence of such a link is also supported by the observation that chromosome aberrations are induced by ionizing radiation in noncycling AT cells.

hMre11-hRad50 IRIF are also independent of DNA-PK$_{CS}$, which is implicated in nonhomologous end joining. hMre11-hRad50 IRIF were observed in DNA-PK$_{CS}$-null cells (M059J) and DNA-PK$_{CS}$-positive cells (M059K). Further, DNA-PK$_{CS}$ and Ku proteins do not coimmunoprecipitate with the hMre11-hRad50 protein complex.

The kinetics of IRIF formation resemble those of misrepair and chromosome rearrangement. Previous studies utilizing IMR90 fibroblasts and other repair-proficient cells demonstrate two kinetically distinct modes of DSB repair: a fast component in which >75% of initial DSBs are repaired and a slow component. Utilizing a hybridization-based assay, Lobrich et al. (1995) determined that the slower-rejoining component consisted of primarily incorrect rejoining events and proceeded over a period of 2 to 48 hours postirradiation. Premature chromosome condensation assays, in conjunction with fluorescent in situ hybridization, have been used to examine the kinetics of chromosome exchanges and DSB rejoining in irradiated normal fibroblasts. The data suggest that the number of cells with multiple chromosomal exchange events reaches a maximum between 6 to 12 hours after irradiation with 10 Gy. hMre11-hRad50 IRIF formation follows similar kinetics, with maximal induction at 8 hours postirradiation. In this study, neutral comet analyses were used to confirm that maximal IRIF formation occurs after the majority of DSBs are repaired. Thus, whereas the induction of IRIF is dependent upon DSBs, hMre11-hRad50 IRIF may not show a strict relationship with DSBs per se. Given the proposed function of hMre11-hRad50 in recombinational DNA repair and the dependence of IRIF on the prior induction of DNA DSBs, hMre11-hRad50 IRIF may correspond to these exchange or misrepair events.

Conclusion. These studies support the inferred role of the hMre11-hRad50 protein complex in DSB repair. As shown above, hMre11-hRad50 IRIF form as part of the normal cellular response to DNA damage. Within an asynchronous culture, cells appear to be committed to the formation of either hMre11-hRad50 or hRad51 IRIF, suggesting a commitment to either nonhomologous end joining or homologous recombination for the repair of DSBs. The hMre11-hRad50 IRIF response is abrogated in AT cells but is unaffected by loss of p53. This may suggest a p53-independent function for ATM that is directly linked to the regulation of recombinational DNA repair. Further assessment of the function of hMre11-hRad50 IRIF awaits the ability to identify DNA DSBs in situ and thereby localize hMre11-hRad50 IRIF to sites of damage. Elucidation of the biochemical activities and composition of the hMre11-hRad50 protein complex will also provide important insight.

EXAMPLE 2

In Situ Visualization of DNA Double Strand Break Repair in Human Fibroblasts

Proteins that mediate certain aspects of DNA metabolism, such as DNA replication, appear to be compartmentalized within the nucleus. DNA replication therefore requires the movement of DNA to and from established sites within the nuclear matrix (Hozak et al., 1993; Strougolis et al., 1996). Cytologic analyses have revealed that the DSB repair proteins hRad51 and the hMre11-hRad50 complex assemble in discrete nuclear foci as part of the normal cellular response to DNA damage (Haaf et al., 1995; Scully et al., 1997; and Park et al., 1996). These findings may indicate that DNA repair does not entail the movement of DNA double strand breaks (DSBs) to pre-existing intranuclear sites. Rather, they suggest that DNA repair proteins move to sites of DNA damage.

To address this, a method was developed to examine the temporal and spatial nature of DSB repair within the context of the intact cell. This method relies on synchrotron-generated ultrasoft X-rays (<5000 electron-volts (5 keV)), a multilayer monochromator for tunable ultrasoft x-ray energies with sufficient intensity for irradiation of live human fibroblasts (MacKay et al., 1998), and micro-fabricated irradiation masks to induce DNA damage in discrete subnuclear regions of irradiated cells (FIG. 1) (Nelms et al., 1998). The irradiation masks were fabricated with x-ray lithography and consist of gold strips, 1.85 μm-wide with 1.35 μm separation, deposited on thin $Si_2N_4$ membranes (Nelms et al., supra). Dosimetric analyses with the irradiation mask showed that gold-shielded regions receive approximately 0.5% of the dose absorbed by the non-shielded regions (Nelms et al., supra). Irradiated cells thus absorb ultrasoft X-rays in 1.35 μm-wide stripes separated by 1.85 μm gaps that remain essentially unirradiated.

The 1.34 keV ultrasoft x-rays used in these experiments act almost exclusively through photoelectric interactions in biological material (Virsik-Peuckert, 1983), resulting in low-energy electrons that have very short track lengths (<50 μm), comparable to the dimensions of biologically relevant structures such as chromatin (Goodhead et al., 1993). These properties suggested that photo- and Auger-electrons as well as free radicals resulting from absorption of ultrasoft X-rays would induce DNA damage almost exclusively within the 1.35 μm stripes imposed by the grids.

Log phase 37Lu human fibroblasts which had been plated on 8 μm mylar were irradiated with a mean nuclear dose (D) of 100 Gray (Nelms et al., supra). The dose was calculated using the known entrance dose ($D_e$), the attenuation coefficient (μ) of 1.34 keV X-rays in cells (0.19 mm$^{-1}$), and the estimated cell thickness [$T_n$=nuclear thickness (5 μm), $T_c$=cytoplasmic thickness (0.5 μm)] in the equation $D=(D_e/\mu T_n)(e^{-\mu Tc}-e^{-\mu(Tc+Tn)})$.

Cells were fixed and permeabilized at 30 minutes, 90 minutes, or 5 hours post-irradiation as described in Kodym and Hurth (1995). Cells were briefly washed in ddH$_2$O and incubated for 60 minutes at 37° C. in labeling mix [100 mM sodium cacodylate (pH 7.6), 1 mM CoCl$_2$, 0.2 mM dithiotreitol, 0.005% Triton X-100, 45 nmol/ml 5-bromo-2'-deoxyuridine 5'-triphosphate (BrdU), 250 units/ml terminal deoxytransferase (Promega, Madison, Wis.)]. Labeling reactions were stopped by rinsing with Tris-buffered saline [TBS; 100 mM Tris-HCl (pH 7.5), 150 mM NaCl] and cells were incubated for 20 minutes at 37° C. in a blocking solution consisting of 2% bovine serum albumin (BSA) and 0.3% Triton X-100 in TBS, followed by a 30 minute incubation at 37° C. with 6.25 mg/ml fluorescein isothiocyanate (FITC)-conjugated anti-BrdU (Becton Dickinson) in blocking solution. Cells were washed for 10 minutes in three changes of fresh TBS, counterstained with 4,6-diamidino-2-phenylindole (0.1 μg/ml), and mounted in anti-fade solution [2.3% diazabicyclo {2.2.2} octane, 90% glycerol, 10 mM Tris-HCl (pH 7.5)] (Li et al., 1995; and Kodym and Hurth, 1995).

Optical sectioning was carried out with a BioRad MRC600 confocal microscope system (using the FITC filter set; 60×1.4 N.A. objective). Z-series (in the plane perpendicular to the x-ray beam direction) were collected with a step size of 0.5 µm starting from the plating surface (beam proximal). The average cell thickness was about 5 to 5.5 µm. The resulting stacks were viewed and contrast enhanced with NIH Image 1.61 (ftp://codon/nih.gov/pub/nih-image/). Individual sections were then extracted into Photoshop 4.0 (Adobe).

Figure 2:
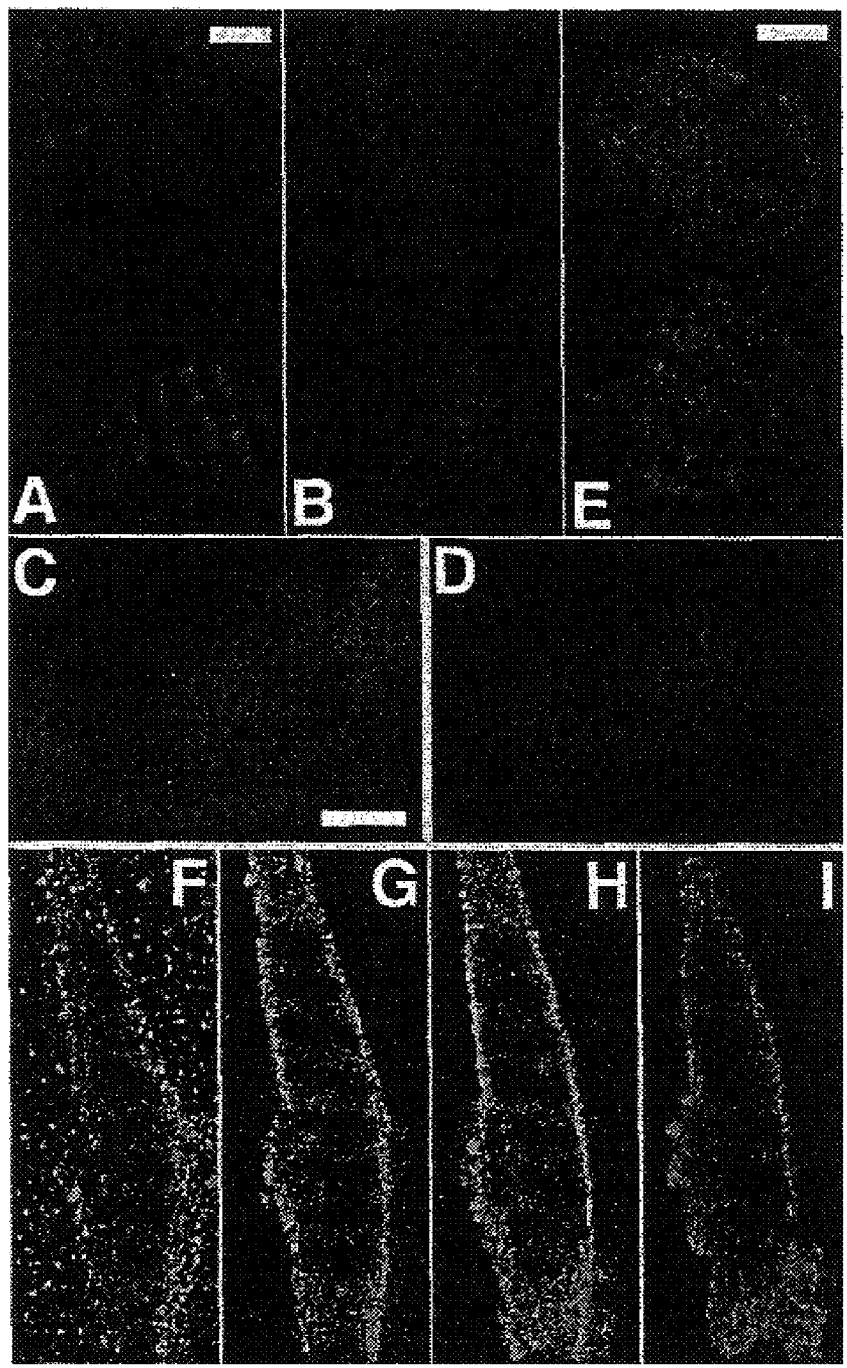
FIG. 2. Partial volume irradiation of 37Lu or 180BR human fibroblasts. The cells were labeled for DSBs with BrdU and FITC-conjugated anti-BrdU mAb (A, C, E), followed by DAPI (13, D) counterstaining. (A, B) 37Lu, 30 minutes post-irradiation; bar, 5 μm; (C, D) 37Lu, 90 minutes post-irradiation; bar 5 μm; (E) 180 BR, 5 hours post-irradiation; Bar, 5 μm; (F–I) Optical sections of a partially irradiated 37Lu nucleus labeled for DSBs with BrdU. Representative images separated by 1.0 μm are shown, with increasing distance from the X-ray beam from (F) to (I). The high background observed in (F) is caused by autofluorescence from the Mylar plating surface.

Under the conditions used, TdT does not label single-strand DNA nicks (Kodym and Hurth, 1995). Nuclei observed at 30 minutes post-irradiation (IR) displayed a strong FITC signal in parallel stripes corresponding to BrdU incorporation at DNA ends (FIG. 2A). Each pair of unirradiated/irradiated stripes is 3.2 µm wide (1.85 µm unirradiated+1.15 µm irradiated). Hence, most nuclei (average diameter 15–20 µm) contained 6–7 FITC-staining stripes (FIG. 2A). Confocal microscopy demonstrated that parallel stripes of BrdU incorporation were uniform throughout the volume of the nucleus at this timepoint (FIGS. 2F–I). These data indicate that ultrasoft X-rays induce highly localized DNA damage in living cells.

The FITC signal corresponding to BrdU-labeled DSBs disappeared between 90 (FIG. 2C) and 300 minutes after irradiation. Single cell electrophoresis (comet) assays revealed that the failure to detect FITC stripes at later time points was due to repair rather than redistribution of the DSBs. Neutral comet assays (Example 1) were carried out on human 37Lu fibroblasts after partial volume irradiation. The level of DSBs remaining in cells observed at 5 hours after irradiation (mean tail moment, 11.5) was comparable to that in unirradiated controls (mean tail moment, 12.9), and reduced from the level of DSBs observed at 30 minutes post-irradiation (mean tail moment, 50.8). Thus, single cell electrophoresis assays revealed that the failure to detect FITC stripes at later time points was due to repair rather than redistribution of the DSBs. Similar DSB repair kinetics were previously observed after ultrasoft X-irradiation without an irradiation mask (Botchway et al., 1997).

If DSBs were largely stationary prior to repair, their persistence in a DNA repair-deficient cell would lead to the persistence of DSB stripes. To test this hypothesis, the DSB repair-deficient human fibroblast cell line, 180BR (Badie et al., 1995), was stripe-irradiated, contacted with BrdU and TdT, and stained with FITC-α-BrdU to visualize DSBs. In contrast to 37Lu cells, in which BrdU incorporation was undetectable by 90 minutes post-irradiation, the 180BR cells had readily observable FITC-α-BrdU stripes as late as 300 minutes post-irradiation (FIG. 2E). Previous analyses had shown that minimal DSB repair occurs over this time course in 180BR cells (Example 1; Badie et al., 1995). These data indicate that DSBs are held in a relatively fixed position, at least in the early stages of DNA repair, and suggest that the bulk of DSB repair does not involve movement of DNA lesions through intranuclear space. In this regard, DSB repair differs from DNA replication, which is mediated by compartmentalized nuclear proteins (Hozak et al., 1993; Example 1). Instead, the spatial behavior of DSBs suggested that DSB repair requires the recruitment of DSB repair proteins to sites of damaged DNA.

Several criteria indicate that DSB repair complexes, one that includes hMre11 and hRad50 and another that includes hRad51, both of which form nuclear foci in response to the induction of DSBs (Example 1; Haaf et al., 1995), play distinct roles in DSB repair. The hMre11-hRad50 complex exhibits sequence similarity to the bacterial exonuclease SbcCD (Leach et al., 1994; Sharples et al., 1995; and Connelly and Leach, 1996), suggesting that this complex functions as an exonuclease that may be involved in the processing of DNA ends prior to strand exchange and religation (Kanaar et al., 1997; Szostak et al., 1983; Sugawara et al., 1992; Ivanov et al., 1994; and Petrini et al., 1997). Since hRad51, a human RecA homolog, mediates DNA strand exchange (Sung et al., 1995; Baumann et al., 1996; and Gupta et al., 1997), its action is likely to be required later than that of the hMre11-hRad50 protein complex in DSB repair. Null Scmre11 and Scrad51 mutations in *Saccharomyces cerevisiae* indicate that the yeast Mre11-Rad50-Xrs2 complex, but not ScRad51, plays an important role in nonhomologous endjoining in this organism (Kanaar et al., 1997; Petrini et al., 1997). Finally, both biochemical and cytologic experiments indicate that hRad51 is not physically associated with the hMre11-hRad50 complex (Example 1).

To determine whether partial volume irradiation could distinguish the actions of hRad51 and hMre11 in intact nuclei, DSBs in cells were stained with FITC-anti-BrdU, the cells were then washed in phosphate buffered saline, blocked and stained with α-hMre11 as described in Example 1, except that lissamine rhodamine-conjugated antibody to rabbit immunoglobulin (IgG) (Jackson ImmunoResearch, West Grove, Pa.) was substituted for FITC-conjugated secondary antisera.

Figure 3:
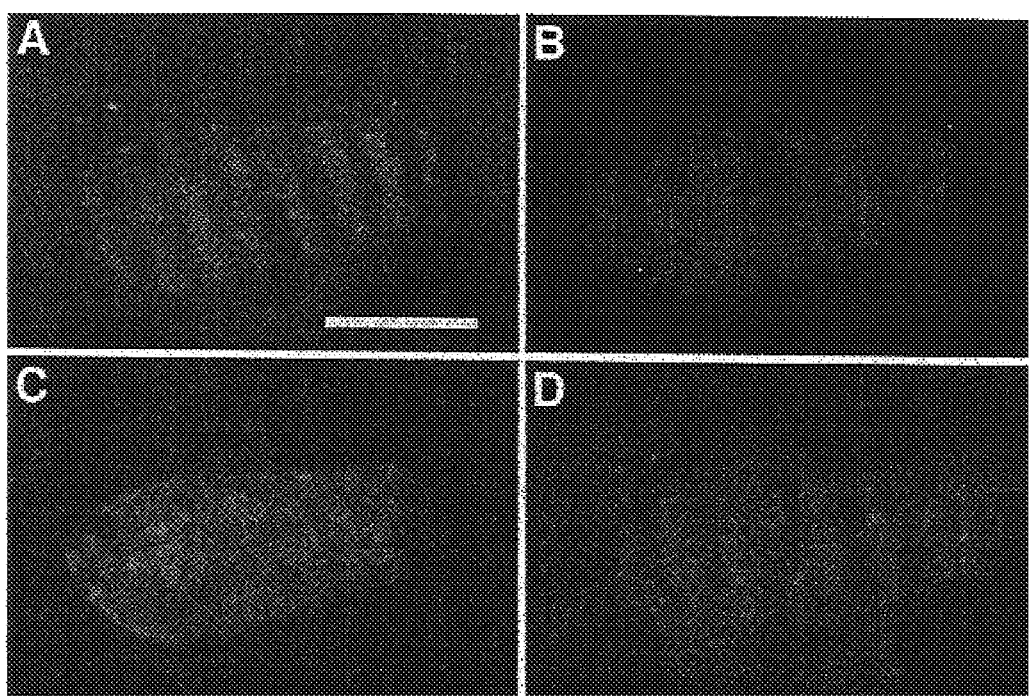
FIG. 3. Colocalization of BrdU incorporation and hMre11 stripes. At 30 minutes post-irradiation, 37Lu fibroblasts were sequentially labeled to detect (A) BrdU (FITC-conjugated anti-BrdU mAb), (B) hMre11, and (C) DNA (DAPI). (D) Merged image of (A) to (C), Bar, 10 μm.

Analysis of stripe-irradiated doubly stained 37Lu cells revealed that as early as 30 minutes post-irradiation, the BrdU-labeled DSBs and hMre11 protein colocalized (FIG. 3). The abundance and composition of the hMre11-hRad50 complex are identical in irradiated and unirradiated cells (Example 1; Dolganov et al., 1996). Hence, the association of these proteins with damaged DNA was due to migration of existing hMre11-hRad50 complexes. Optical sectioning of hMre11-stripe positive nuclei revealed that hMre11 protein was localized in stripes throughout the nuclear volume. FITC signal (corresponding to DSBs) disappeared by 90 to 300 minutes after irradiation, whereas hMre11 staining became diffuse, as it is in unirradiated cells.

Figure 4:
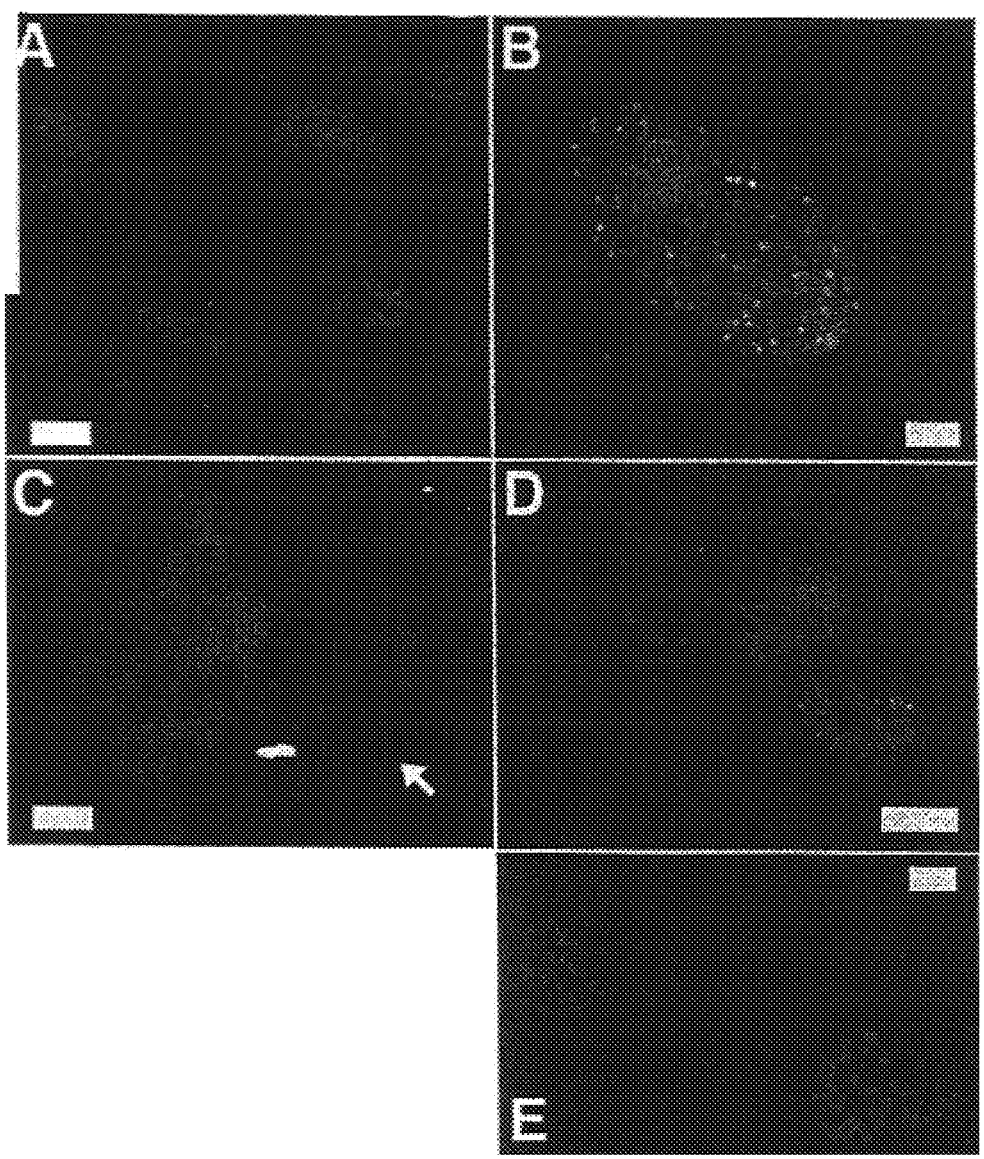
FIG. 4. Localization of hMre11 to stripes after partial volume irradiation. 37Lu (A to D) or 180BR (E) fibroblasts were fixed after partial volume irradiation and stained for hMre11 or hRad 51. (A) anti-hMre11, 30 minutes post-irradiation; (B) anti-hRad51, 30 minutes post-irradiation; (C) anti-hMre11, 5 hours post-irradiation; note that one nucleus (arrow) shows a weak stripe pattern; (D) anti-hRad51, 5 hours post-irradiation; (E) anti-hMre11 in 180BR cells, 5 hours post-irradiation. Bar in (A) and (D), 10 μm; in (B), (C) and (E), 5 μm.

Vestigial hMre11 stripes persisted in approximately 5% of nuclei examined at 300 minutes (FIG. 4C). Previous studies of DSB repair in human cells have indicated that the bulk of ionizing radiation-induced DSBs are repaired within the first 60 minutes post-irradiation, and that a more slowly repaired population of DSBs persists for 24–48 hours (Botchway et al., 1997; Cornforth et al., 1983). The data described above suggest that the hMre11-hRad50 complex functions in the fast component of DSB repair. Since it was previously shown that these proteins also function in the slower component of DSB repair (Example 1), the residual hMre11 stripes may indicate that the number of slowly repaired DSBs falls below the limit of TdT detection whereas immunofluorescent detection of hMre11 is sufficiently sensitive to identify these slower repair events.

To determine if localization of hMre11 was attributable to the presence of DSBs, irradiated DSB repair-deficient 180BR cells were analyzed for extended hMre11 localization. It was observed that the hMre11 stripes were present in the majority of irradiated 180BR cells as late as 300 minutes post-irradiation (FIG. 4E), in contrast to the results with 37Lu cells. Thus, DSBs appear to constitute the signal for hMre11 localization.

Next, it was investigated whether hMre11 and hRad51 colocalized at sites of DNA damage in stripe-irradiated 37Lu cells. 37Lu or 180BR fibroblasts were plated and irradiated. At 30 or 300 minutes after irradiation, cells were fixed in 4% paraformaldehyde in 200 mM sucrose/PBS (pH 7.4) for 5 minutes, and then permeabilized for 5 minutes (Scully et al., 1997). Cells were incubated in blocking solution and then treated with α-hMre11 antiserum, α-hRad51 antiserum, or double labeled with α-hRad51 antiserum plus Texas Red conjugated α-hMre11 (Example 1). Images were captured under epifluorescence using a cooled charge-coupled device camera and images were processed using Photoshop 4.0 (Adobe).

As above, at 30 minutes post-irradiation, the majority (>90%) of nuclei exhibited a striped pattern of hMre11 localization (FIG. 4A). Approximately 10% of cells contained hRad51 foci at 30 and 300 minutes post-irradiation, but these foci did not form a striped pattern at either time point (FIGS. 4B and 4D). The failure of hMre11 and hRad51 to colocalize in irradiated stripes supports the assertion that these proteins mediate distinct functions in the DSB repair process, consistent with our previous cytologic analyses (Example 1). The fraction of hRad51 focus-positive irradiated cells observed in these experiments was somewhat lower than in previous studies, presumably reflecting the low levels of hRad51 expression in the primary fibroblasts used for this study (Example 1; Haaf et al., 1995; Yamamoto et al., 1997; and Flygare et al., 1996).

These observations confirm that biologically relevant interactions of ultrasoft X-rays are confined to small intranuclear volumes (Virsik-Peuckert, 1983; Cox et al., 1977; Goodhead et al., 1979), and provide physical evidence that the hMre11-hRad50 protein complex localizes to the sites of DNA damage. These findings indicate that the activation of DNA repair must include relocalization of repair proteins to the sites of DNA damage. DNA repair enzymes thus appear to resemble transcription factors and RNA processing enzymes which are proposed to migrate within the nucleus, but are distinct from enzymes that mediate DNA replication from stationary replication factories (Hosak et al., 1993; Strouboulis et al., 1996; Singer et al., 1997).

Relocalization of the hMre11/hRad50 protein complex may indicate that signals originate from the site of DNA damage to recruit DNA repair enzymes. In this regard, the signal that activates DNA repair may be analogous to those that activate DNA damage-dependent cell cycle checkpoint functions (Nelson et al., 1994; and Huang et al., 1996). It has been suggested that the DNA-activated Protein Kinase trimeric complex (Ku70/Ku86/DNA-PKcs), which binds to DNA ends in vitro and induces protein phosphorylation activity, may act to signal the presence of DNA damage (Hoekstra, 1997; Jackson, 1996; Jeggo et al., 1995, and Weaver 1995). Based on the failure to suppress DNA synthesis after ionizing radiation of cells established from ataxia telangiectasia patients, a similar function has been proposed for ATM (Shiloh, 1997). The use of mutants such as dna-pk and ATM in partial volume irradiation assays may help to define defects in signaling functions required for relocalization of DSB repair proteins.

EXAMPLE 3

Linkage of Double Strand Break Repair to the Cellular DNA Damage Response

Materials and Methods

Cell Lines. HeLa S3 cells were obtained from the University of California-Berkeley Tissue Culture Center. Cell lines derived from patients with Nijmegen breakage syndrome were obtained from K. Sullivan (Children's Hospital of Philadelphia) and P. Concannon (Virginia Mason Research Center, Seattle, Wash.). Ataxia telangiectasia primary fibroblasts (AT3BI) were obtained from J. Murnane (University of California, San Francisco). IMR90, 37Lu, TK6, and K562 cell lines were grown as previously described (Example 1). HeLa cells were grown in Joklik's MEM containing 5% newborn calf serum, 50 IU/ml penicillin and 50 µg/ml streptomycin. AT3BI and NBS primary fibroblasts (lines KW and WI 799) were grown in DMEM/10% FCS/5% Fetal Clone III (Hyclone, Logan Utah) and NBS lymphoblasts (lines JS, GM7078, and DST) were grown in RPMI 1640/15% FCS.

Protein Purification. Crude HeLa extract was prepared essentially as described (Nishida et al., 1988). All procedures were carried out at 4° C. A 20% to 50% $(NH_4)_2SO_4$ fraction was loaded on to a DEAE-sephacel column equilibrated in 50 mM Tris-HCl (pH 8.0), 1 mM DTT, 10% glycerol and 50 mM NaCl (TDG+50). The column was eluted with a 50 mM to 500 mM NaCl gradient. hMre11 and hRad50 co-eluted at 180 mM NaCl. Pooled fractions were concentrated by $(NH_4)_2SO_4$ precipitation and resuspended in TDG+200.

hMre11 immunoaffinity reagent was constructed by crosslinking affinity-purified hMre11 antiserum with dimethylpimelimidate to protein A-agarose as described (Harlow and Lane, 1988). Pooled DEAE-sephacel fractions were incubated with the α-hMre11 beads in 300 mM NaCl. Beads were washed, and bound proteins quantitatively eluted with Acti-Sep elution media (Sterogene Carlsbad, Calif.). Eluted proteins were dialyzed into 10 mM Tris-8.0, 25 mM NaCl, and fractionated by SDS-PAGE. Proteins were visualized with colloidal Coomassie blue and the unique 95 kDa band was excised for mass spectrometry analysis.

For gel filtration, pooled DEAE-sephacel column fractions derived as above were subjected to gel filtration on Superose 6 FPLC column (Pharmacia, Piscataway, N.J.). Fractions were analyzed by Western blotting with p95, hMre11, and hRad50 antisera.

Mass Spectrometry. Proteins were subjected to in-gel trypsin digestion (Shevchenko et al., 1996). Microelectrospray columns were constructed from 360 micron O.D.×100 micron I.D. fused silica capillary with the column tip tapered to a 5–10 micron opening. The columns were packed with Perceptive Biosystems (Framingham, Mass.) POROS 10 R2, a 10 micron reversed-phase packing material, to a length of 10–12 cm. The flow from the HPLC pumps (typically 150 microliters/minute) was split precolumn to achieve a flow rate of 500 nL/minute. The mobile phase used for gradient elution consisted of (A) 0.5% acetic acid, and (B) acetonitrile/water 80:20 (v/v) containing 0.5% acetic acid. The gradient was linear from 0–40% B in 50 minutes followed by 40–80% B in 10 minutes or 0–60% B in 30 minutes. Mass spectra were recorded on an LCQ ion trap mass spectrometer (Finnigan MAT, San Jose, Calif.) equipped with a microelectrospray ionization source (Gatlin et al., 1998). Electrospray was performed at a voltage of 1.6 kV. Tandem mass spectra were acquired automatically during the entire gradient run as previously described (Link et al., 1997). Tandem mass spectra of peptides from p95 were compared to the protein and gene sequence using the computer program SEQEST (Eng et al., 1994; Yates et al., 1995). Sequences for potential contaminants such as human keratin and bovine trypsin were added to the database.

Two-Hybrid Interaction. hMre11 (nucleotides 160 to 2298 of hMre11 gene encoding the full length hMre11 polypeptide) was expressed as a GAL4 DNA binding domain fusion protein from pAS1 (Durfee et al., 1993) in the yeast strain, PJ69-4A (James et al., 1996). Following introduction of a human B-lymphoblastoid cell cDNA library into the vector pACT, cDNAs encoding hMre11 interactors were selected for by growth in the absence of adenine. Apparent adenine prototrophic colonies were retested on plates lacking histidine or adenine, and pACT cDNA clones were isolated from yeast exhibiting adenine and histidine prototrophy and analyzed by DNA sequencing.

Hybridizations. Multiple Tissue Northern Blots (Clontech, Palo Alto, Calif.) were probed as previously described (Dolganov et al., 1996) utilizing a NBS1 or hMRE11 cDNA labeled by random priming as the probe. The Zoo-Blot Southern blot was obtained from Clontech (Palo Alto, Calif.) and probed by standard procedures utilizing the NBS1 cDNA as a probe.

Immunoblotting and Immunoprecipitation. p95 antiserum was raised in a rabbit against a fusion protein comprising amino acids 399–751 of human p95 fused to glutathione-S-transferase (GST). Affinity purification of anti-p95 antiserum was performed (Dolganov et al., 1996) over GST (to remove GST reactivity from the antiserum) and GST-p95 columns constructed with actigel resin (Sterogene, Carlsbad, Calif.). The hMre11 monoclonal antibody was derived from a mouse immunized with a 6X-His-hMre11 fusion protein (the fusion protein included the complete hMre11 polypeptide) in the University of Wisconsin Hybridoma facility.

Whole cell extracts (from $3 \times 10^5$ cells) were prepared (Dolganov et al., 1996) and fractionated in 7.5% SDS-PAGE gels. Proteins were transferred to nitrocellulose and immunoblots were performed (Dolganov et al., 1996) with p95, hMre11, and hRad50 antisera on the same filter in succession. Immunoprecipitations were performed on K562 lysates with p95, hMre11, hRad50 or the respective pre-immune antisera (Dolganov et al., 1996). Immunoprecipitates were fractionated, transferred to nitrocellulose and immunoblotted as above.

Chromosomal localization of p95. Metaphase chromosomes were prepared from phytohemagglutin-stimulated peripheral blood lymphocytes from a normal human subject. The NBS1 probes (clones 926991 and 1083839) were biotin-labeled by nick translation using Bio-16-dUTP (Enzo Diagnostics, Farmingdale, N.Y.) and fluorescence in situ hybridization was performed (Rowley et al., 1990). Hybridization was detected with fluorescein-conjugated avidin (Vector Laboratories, Burlingame, Calif.), and chromosomes were identified by staining with 4,6-diamidino-2-phenylindole-dihydrochloride (DAPI).

Immunofluorescence. Primary fibroblasts were grown on glass slides, irradiated and fixed (Example 1). For double immunolabeling, cells were fixed in 3.5% paraformaldehyde and permeabilized (Scully et al., 1997). Cells were incubated with affinity-purified rabbit p95 antiserum (as above) and a 1:50 dilution of anti-hMre11 monoclonal ascites (line 8F3) for 1 hour at room temperature. After washing in PBS, cells were incubated with FITC-conjugated goat anti-rabbit and Texas Red-conjugated donkey anti-mouse antisera (Jackson Immunoresearch, West Grove, Pa.) for 1 hour at room temperature. Cells were then washed, counterstained with DAPI, and mounted (Example 1).

In IRIF assays, a minimum of 200 nuclei were analyzed for each cell line, treatment, and antibody examined (Example 1). Unirradiated samples were fixed and processed as above along with irradiated samples. Mutant NBS cells and normal controls were processed simultaneously and treated identically.

Results

Purification of the hMre11/hRad50 Complex from HeLa Extract

Figure 5:
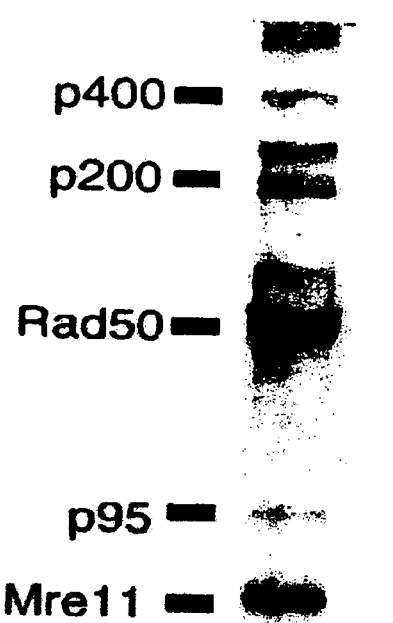
FIG. 5. Purification of hRad50/hMre11 complex. The eluent from the anti-hMre11 protein A-agarose beads was separated by SDS-PAGE and stained with colloidal coomassie blue. The five specific bands that purify with the complex are indicated.

The 95 kDa and 200 kDa components of the hMre11/hRad50 protein complex were purified from a HeLa cell extract for direct protein sequencing. A 20% to 50% $(NH4)_2SO_4$ precipitate was separated by anion-exchange chromatography, and fractions containing hRad50 and hMre11 were identified by Western blotting. The hRad50/hMre11 complex was further purified from peak fractions by immunoaffinity chromatography and fractionated by SDS-PAGE. The hMre11/hRad50 protein complex includes five proteins of 81 kDa, 95 kDa, 150 kDa, 200 kDa, and approximately 400 kDa, which are immunoprecipitable by hMre11 antiserum (Dolganov et al., 1996). As expected, these proteins were readily visible on a Coomassie-stained gel (FIG. 5). The 95 kDa and 200 kDa bands (referred to henceforth as p95 and p200) were excised from the gel and subjected to mass spectroscopic analysis.

Mass Spectrometry of Purified Proteins

The p95 protein was digested with trypsin and analyzed by LC/MS/MS to acquire tandem mass spectra for sequence analysis. A tandem mass spectrum for a peptide of molecular weight 1,420.2 Da was interpreted to represent the sequence NPSGLNDDYGQLK (SEQ ID NO:5). A tBLASTx search of dbEST found a match to the sequence NPSGLND-DYGQLK (SEQ ID NO:5) in human EST 926991.

A similar analysis of the p200 band identified this protein as fatty-acid synthase (FAS) (Jayakumar et al., 1996). Since subsequent gel filtration chromatography indicated that FAS did not co-elute with the hRAD50/hMre11 complex, it was concluded that the presence of FAS among the immunoaffinity purified proteins was an artifact of the isolation procedure.

Cloning of the NBRS1 cDNA

Figure 6:
FIG. 6. Structure of the p95 cDNA. (A) The schematic diagram represents the structure of the p95 cDNA. The entire 4,483 basepair (bp) cDNA is represented by the thin line and the rectangular box is the 754 amino acid (aa) open reading frame (ORF) (SEQ ID NO:2). Within the ORF the grey box indicates the N-terminal region showing homology to S. cerevisiae Xrs2. The solid line above the ORF indicates the region cloned by two-hybrid screen utilizing hMre11 as bait. (B) N-terminal alignment of p95 (SEQ ID NO:3) with Xrs2 (SEQ ID NO:4). The shaded boxes indicate the regions of similarity. The two proteins show 28% identity and 46% similarity over the region displayed. The following amino acids were considered similar: {D, E, N, Q} {F, W, Y} {I, L, V} {K, R} {A, G} {S, T} {C} {H} {M} {P}. (C) A Zoo-Blot Southern blot (Clontech, Palo Alto, Calif.) of EcoRI digested DNA from various species was probed with the NBS1 cDNA. Lane 1, human; lane 2, monkey; lane 3, rat; lane 4, mouse; lane 5, dog; lane 6, cow; lane 7, rabbit; lane 8, chicken; and lane 9, yeast. The position of size markers (in kilobase pairs) is indicated on the left.

The EST cDNA clone encoding p95 peptides (Table 1) was obtained from the IMAGE consortium (clone identification number 926991 [EST 11]. This clone, and a second overlapping human EST, 1083839 [EST30], were sequenced in their entirety. The combined DNA sequence spanned 4,483 bp (SEQ ID NO:1; FIG. 14) and contained a 2,265 bp open reading frame, sufficient to encode a protein with a predicted molecular weight of 85 kDa (SEQ ID NO:2; FIG. 15). The resulting cDNA has been designated NBS1 (for Nijmegen breakage syndrome). Comparison of the open reading frame with tandem mass spectra obtained from purified p95 identified 16 additional peptide matches (Table 1). The predicted protein has no homology to any known proteins. Contrary to expectations, the predicted p95 protein is essentially unrelated to the S. cerevisiae Xrs2 protein; the two proteins share only modest homology (28% identity) over the N-terminal 115 amino acids (FIG. 6).

TABLE 1

Peptides Obtained From Mass Spectrometry Analysis

| Peptide[a] | Position[b] | SEQ ID NO: |
|---|---|---|
| —QPPQIESFYPPLDEPSIGSK— | 189–209 | 9 |
| —LSSAVVFGGGEAR— | 238–251 | 10 |
| —WIQSIMDMLQR— | 289–299 | 11 |
| —QGLRPIPEAEIGLAVIFMTTK— | 300–320 | 12 |
| —TTTPGPSLSQGVSVDEK— | 335–351 | 13 |
| —MLSQDAPTVKE— | 395–404 | 14 |
| —TSSNNNSMVSNTLAK— | 409–423 | 15 |

TABLE 1-continued

Peptides Obtained From Mass Spectrometry Analysis

| Peptide[a] | Position[b] | SEQ ID NO: |
|---|---|---|
| —IPNYQLSPTKLPSINK— | 426–441 | 16 |
| —NYFQPSTKK— | 458465 | 17 |
| —NKEQHLSENEPVDTNSDNNLFTDTDLK— | 503–529 | 18 |
| —EMDDVAIEDEVLEQLFK— | 552–558 | 19 |
| —MDIETNDTFSDEAVPESSK— | 595–613 | 20 |
| —ELKEDSWAK— | 625–635 | 21 |
| —KLLLTEFR— | 653–660 | 22 |
| —NPSGINDDYGQLK—[c] | 671–683 | 23 |
| —EESLADDLFR— | 736–745 | 24 |

[a]Mass spectrometry is unable to distinguish L/I and Q/K. The indication of L, I, Q, and K residues in the peptide sequences is based on the p95 ORF.
[b]Numbering system is based on the ORF of the p95 cDNA.
[c]This peptide was sequenced by tandem mass spectrometry and used for EST database searches. The remaining peptides corresponded to the derived amino acid sequence from the p95 ORF.

Two-Hybrid Interaction of $p^{95}$ and hMre11

In parallel with the approach described above, a two hybrid interaction screening was employed to identify hMre11-interacting proteins. The hMRE11 cDNA was cloned into the vector pAS1 as an in-frame fusion with the Ga14 DNA binding domain (Durfee et al., 1993), and cDNAs encoding interacting proteins were isolated from a human B lymphoblastoid cDNA library by two hybrid screening. DNA sequence and hybridization analyses revealed that twenty independent NBS1 cDNA clones were among the interactors. The largest NBS1 cDNA obtained in this screen (FIG. 6) began at amino acid position 363 of the p95 protein.

Expression of NBS1

Figure 7:
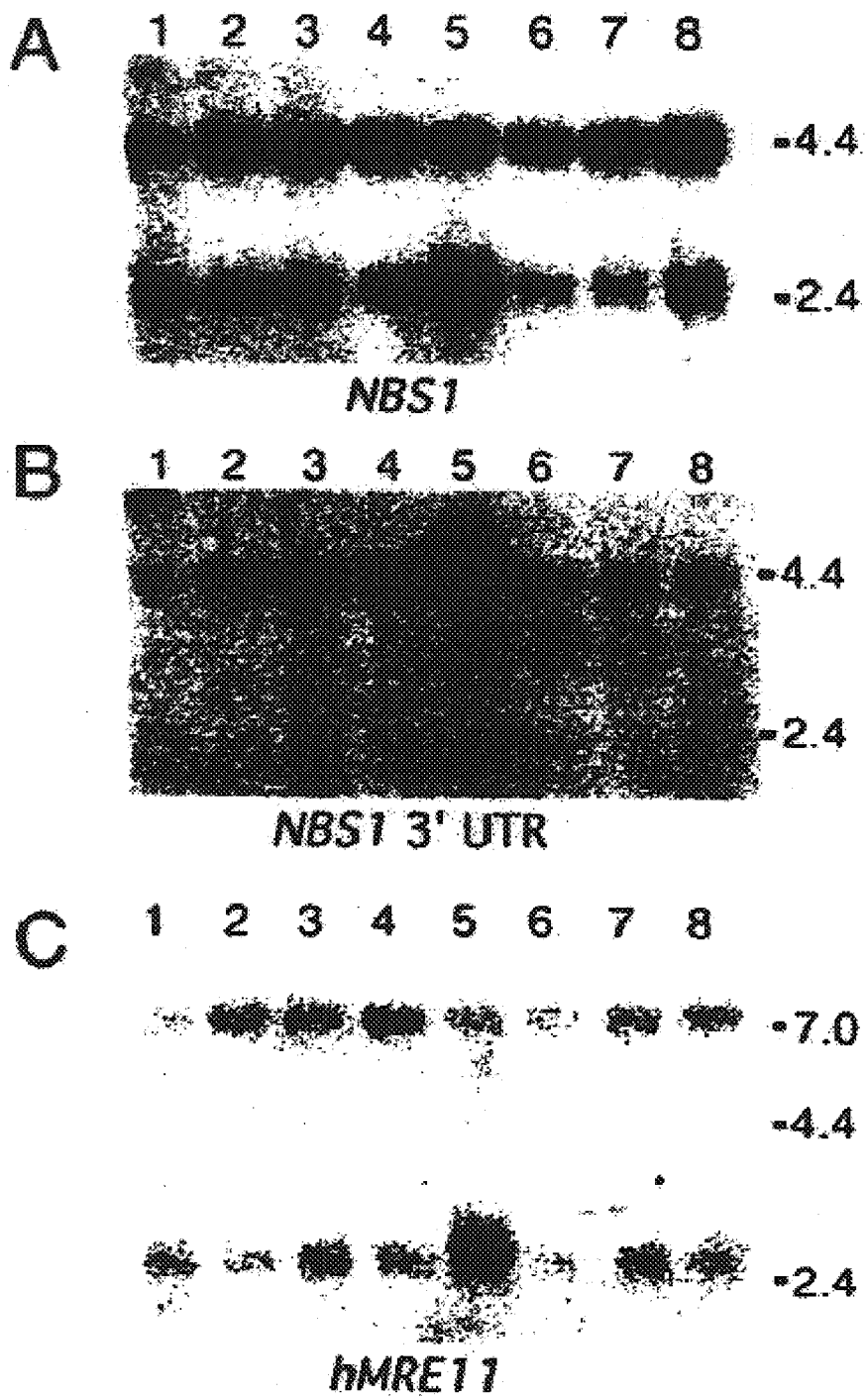
FIG. 7. Northern blot analysis of p95 and hMRE11. (A) A human multiple tissue Northern blot was probed with a cDNA fragment corresponding to bp 1-535 of the NBS1 cDNA. Lane 1, peripheral blood lymphocytes; lane 2, colon; lane 3, small intestine; lane 4, ovary; lane 5, testis; lane 6, prostate; lane 7, thymus; and lane 8, spleen. The positions of the size markers is indicated at right. (B) the blot in (A) was stripped and reprobed with a cDNA fragment from the 3'-UTR of the NBS1 cDNA corresponding to bp 3449-4385. The lanes and markers are identical to (A). (C) The blot from (A) was stripped and reprobed with the human MRE11 cDNA.

Northern blot analysis with an NBS1 cDNA probe revealed two NBS1 mRNAs, a 4.4 kb transcript that was relatively abundant in all tissues, and a 2.6 kb transcript that was present at high levels in testis (FIG. 7A). The 4.4 kb mRNA, and not the 2.6 kb mRNA, was detected with a probe from the 3' non-coding segment of the NBS1 cDNA (FIG. 7B), indicating that the two transcripts arise from the same locus, but differ in the amount of 3' untranslated sequence that they contain. The same Northern blot filter was hybridized to an hMRE11 cDNA probe (FIG. 7C). Two hMRE11 mRNA species were detected; a 6.6 kb mRNA that was present in all tissues, and a 2.4 kb mRNA that was most abundant in testis. This pattern of expression is analogous to that of the murine MRE11 gene (Petrini et al., 1995). The expression patterns of the NBS1 2.6 kb mRNA and the 2.4 kb hMRE11 mRNA were identical, consistent with the observation that their respective protein products function together in the same complex.

Interaction of p95 with the hRad50/hMre11 Complex

Figure 8:
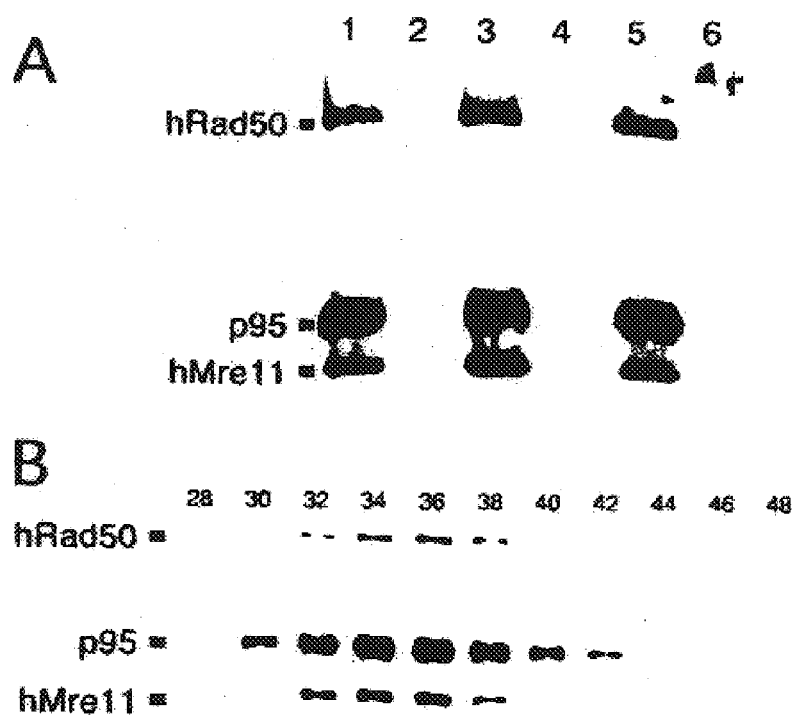
FIG. 8. Interaction of p95 with the hRad50 hMre11 complex. (A) Immunoprecipitations were carried out using K562 crude extract and subjected to Western blot analysis. The Western blot was probed with hRad50, hMre11, and p95 antisera. Lanes 1, 3, and 5 are immunoprecipitates with hRad50, hMre11, and p95 antisera, respectively, and lanes 2, 4, and 6 are the corresponding preimmune sera. (B) Fractions from a Superose 6 FPLC separation of an aliquot of DEAE pool were subjected to Western blot analysis using hRad50, hMre11, and p95 antisera. The numbers at the top are the fraction numbers and the positions of the three proteins are indicated on the left.

To confirm the results of the immunoaffinity purification, a series of immunoprecipitations was performed using K562 cell extracts with hMre11, hRad50, and p95 antisera (Dolganov et al., 1996). Immunoprecipitates were subsequently analyzed by Western blotting with the same antisera. All three proteins (hRad50, hMre11, and p95) were precipitated with the three respective antisera but not with the corresponding pre-immune sera (FIG. 8A, lanes 1–6).

The association of these three proteins was also confirmed by gel filtration chromatography. hMre11/hRad50-containing fractions from the DEAE-sephacel column described above were pooled and separated on a Superose 6 gel filtration column. Western blotting of fractions from the sizing column with hMre11, hRad50, and p95 antisera was carried out. The three proteins co-chromatographed in a single peak corresponding to a molecular weight of approximately 1,600 kDa (FIG. 7B). hMre11, hRad50, or p95 proteins were not detected in later column fractions corresponding to lower molecular weight species. This observation suggests that the vast majority of hMre11, hRad50, and p95 in the cell are present in the high molecular weight complex.

Conservation of p95

Figure 9:
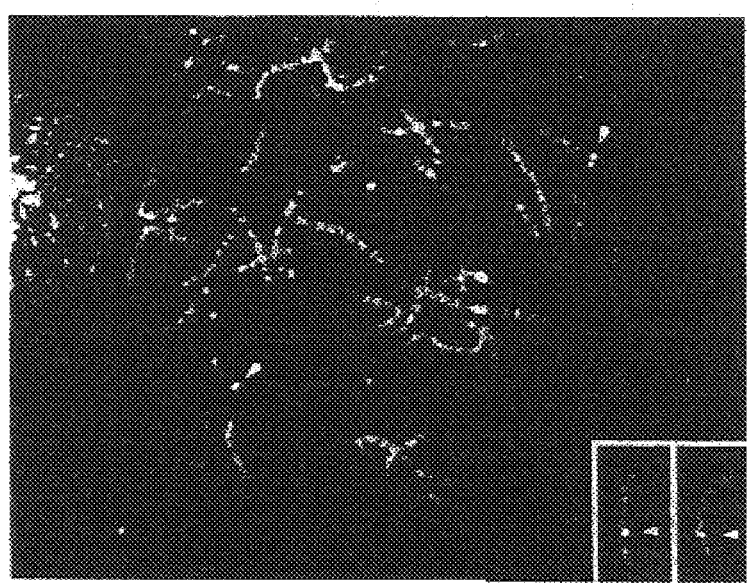
FIG. 9. FISH localization of NBS1 to 8q21.3. Biotin-labeled p95 cDNA probe was hybridized to human metaphase cells from phytohemagglutin-stimulated peripheral blood lymphocytes. The chromosome 8 homologues are identified with arrows; specific labeling was observed at 8q21.3. The inset shows partial karyotypes of two chromosome 8 homologues illustrating specific labeling at 8q21.3 (arrowheads). Images were obtained using a Zeiss Axiophot microscope coupled to a cooled charge coupled device (CCD) camera. Separate images of DAPI stained chromosomes and the hybridization signal merged using image analysis software (NU200 and Image 1.57).

Human metaphase cells were used for fluorescence in situ hybridization (FISH) with the NBS1 cDNA. Co-hybridization of probes EST11 and EST30 resulted in specific labeling only of chromosome 8 (FIG. 9). Specific labeling of 8q21.2–22.1 was observed on four (2 cells), three (5 cells), two (12 cells), or one (6 cells) chromatid(s) of the chromosome 8 homologues in 25 cells examined. Of 61 signals observed, 53 (87%) were located at 8q21.2–22.1. Of these, 4 (7.5%) signals were located at 8q21.3, 46 (87%) signals were located at 8q21.3, and 3 (5.5%) signals were located at 8q22. 1. Eight background signals were observed at other chromosomal sites. Six of these were single signals, and none of these chromosomal bands were labeled more than once. Doublet signals were observed once at 5q14. A specific signal was observed at 8q21.3 in an additional hybridization experiment using this probe. These results suggest that the gene coding for p95 is localized to chromosome 8, band q21.3. Previous studies have demonstrated that the gene defective in the chromosome instability syndrome, Nijmegen Breakage Syndrome (NBS), maps to this locus (Matsuura et al., 1997; Saar et al., 1997).

To determine whether p95 protein was present in cell lines established from NBS patients, extracts were prepared from cell lines from five patients and subjected to Western blot analysis with p95 antiserum. p95 was not detected in any of the patient samples examined (FIG. 10A), although the levels of hMre11 and hRad50 were normal. These data suggest that NBS is attributable to deficiency in the gene encoding p95.

Figure 10:
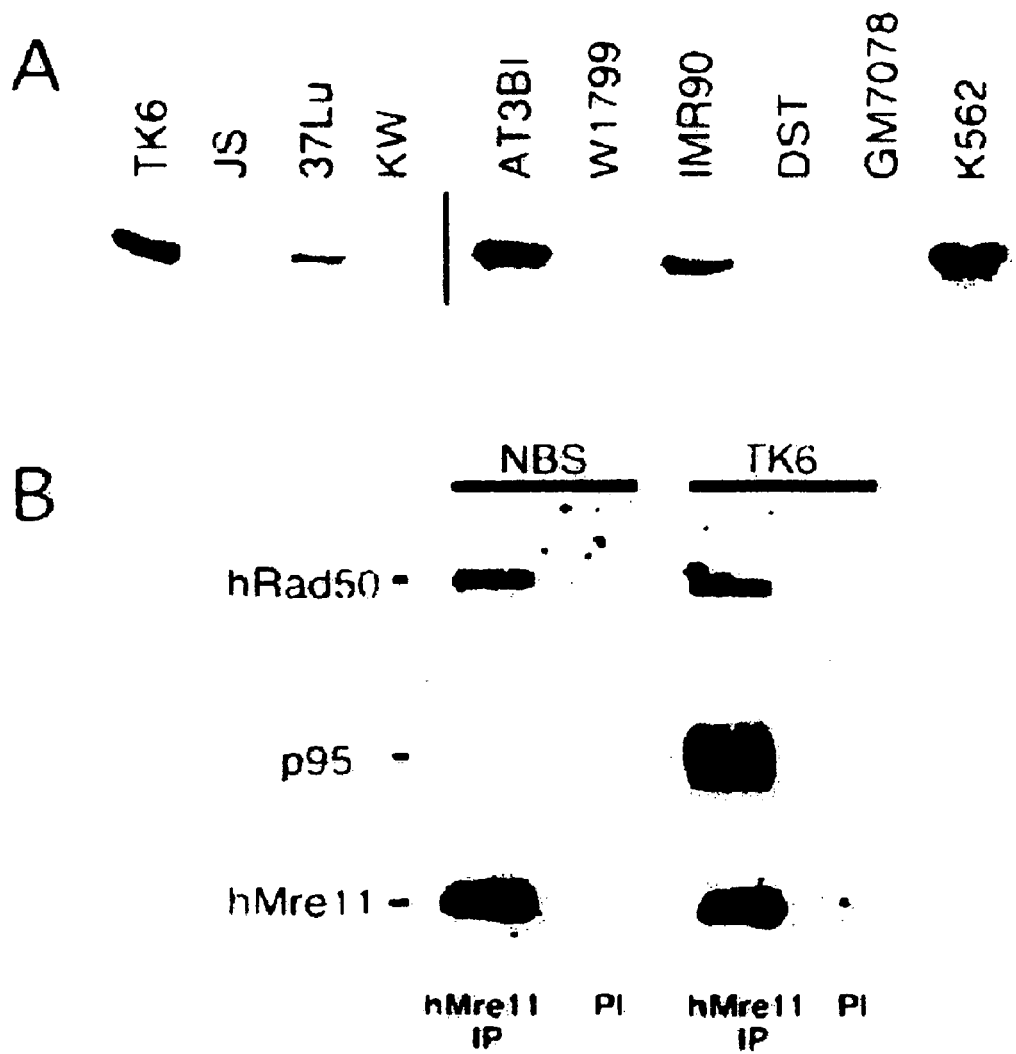
FIG. 10. Analysis of p95 and the hRad50/hMre11 complex in NBS cells. (A) Crude extracts of normal cells (TK6, 37Lu, IMR90, and K562), an AT cell line (AT3BI), and NBS cells (JS, KW, W1799, DST, GM7078) were subjected to Western blot with p95 antiserum. (B) Immunoprecipitations were carried out on crude extracts from JS cells (NBS) and control cell line TK6 hMre11 antiserum (hMre11 IP) or preimmune serum (PI). The resulting precipitates were subjected to Western blotting analysis with hMre11, hRad50, and p95 antisera. The positions of the three proteins are indicated on the left.
Figure 11:
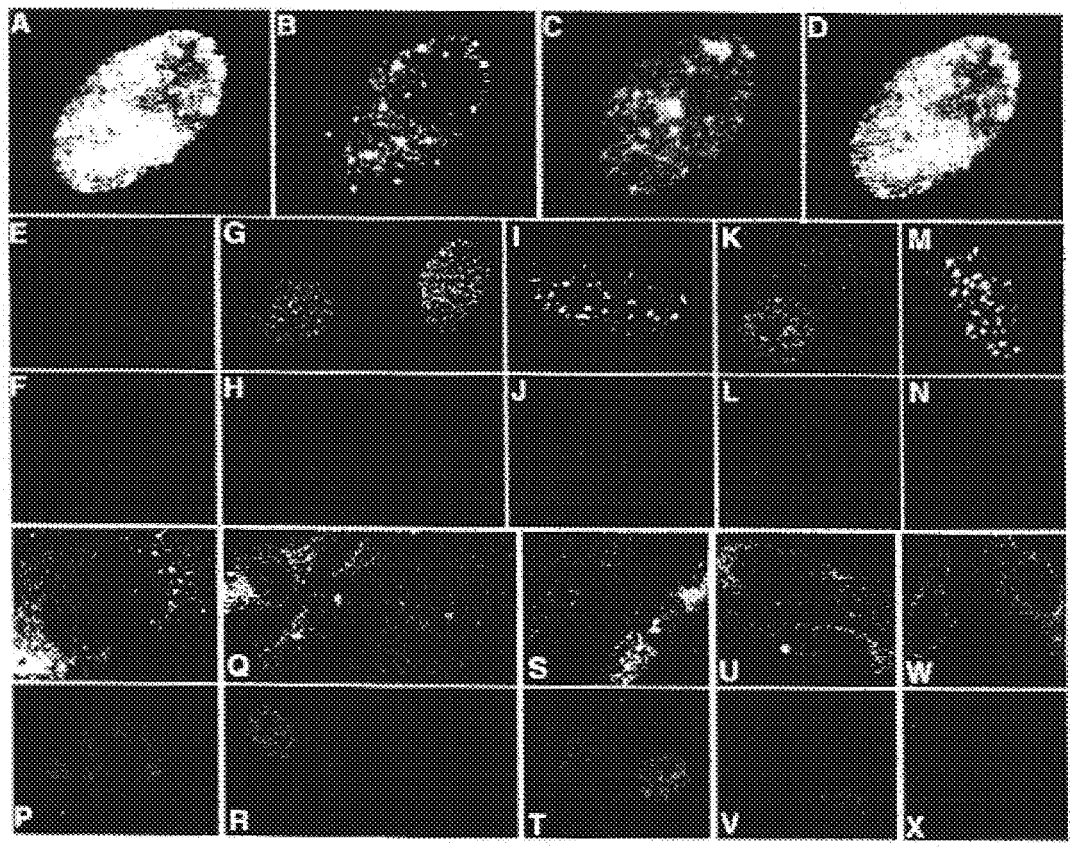
FIG. 11. Ionizing Radiation Induced Foci (IRIF) formed by p95 and hMre11 in 37Lu and NBS cells. Irradiated 37Lu primary fibroblasts were harvested at 8 hours post-irradiation, fixed, and probed with p95 antiserum and hMre11 mAb 8F3 (A→D). Images were captured of the same nuclei under FITC (11A, p95), Texas Red (11B, hMre11), DAPI (11C) filters and merged (11D) in Adobe Photoshop. Normal IMR90 fibroblasts (E-N) and WI 799 NBS fibroblasts (M-X) were assessed for the ability to form IRIF. Unirradiated (E-H, K-L, O-R, U, V) or irradiated (I-J, M-N, S-T, W-X) cells were harvested at 8 hours post-treatment, fixed, and stained with DAPI and three different antibodies. Panels F, O are p95 preimmune serum; F, L are the corresponding DAPI stains. Panels G, I, Q, S, are stained with p95 antiserum; H, J, R, T are the corresponding DAPI stains. Panels K, M, U, W are stained with hMre11 antiserun; L, N, V, X are the corresponding DAPI stains.

To assess whether hRad50 and hMre11 interact in the absence of p95, immunoprecipitations with anti-hMre11 antibody were carried out using crude extracts from a representative NBS cell line (JS; FIG. 10B). It was found that hMre11 and hRad50 were co-immunoprecipitated by anti-hMre11 antibody from NBS extracts and control TK6 extracts (FIG. 10B). The hMre11/hRad50 interaction is unaffected by the absence of p95, indicating that these two proteins interact directly.

Radiation Induced Foci

In human cells, hMre11 and hRad50 colocalize in large nuclear foci following treatment with agents that induce DSBs (Example 1). To examine whether p95 is also present in ionizing radiation induced foci (IRIF), 37Lu (normal diploid fibroblasts) were plated on glass slides, irradiated at a does of 12 Gy, and doubly strained with hMre11 and p95 antisera at 8 hours post-irradiation. hMre11 and p95 IRIF colocalized in irradiated cells, whereas diffuse nuclear staining with both antisera was observed in unirradiated control cells (FIG. 11 and FIGS. 13A–F). As expected from Western blotting (FIG. 10B), p95 was not detectable in NBS cell lines by immunofluorescence (FIGS. 13K–P). This observation is consistent with the notion that hMre11, hRad50, and p95 function in the same protein complex during the normal cellular response to DNA damage.

Normal DNA damage responses such as cell cycle arrest, inhibition of DNA synthesis, and the induction of p53 are abrogated in NBS cells (Jongmans et al., 1997; Sullivan et al., 1997). Therefore, to determine whether the hMre11 IRIF response was intact in cell lines established from NBS patients, NBS fibroblasts (WI 799 and KW) and normal control fibroblasts (IMR90 and 37Lu) were plated on slides as above, irradiated, and stained with hMre11 or p95 antiserum. The hMre11 and p95 IRIF responses of normal cells were consistent with previous studies (Example 1), i.e., 64% to 85% of irradiated cells were positive for IRIF at 8 hours post-irradiation. However, immunofluorescence analysis of over 1500 NBS cells showed that, in contrast to normal cells, the intranuclear levels of hMre11 and hRad50 were drastically reduced n both NBS cell lines, irrespective of prior irradiation (FIGS. 13Q–T). Thus, hMre11-hRad50 IRIF do not form in the absence of p95.

Discussion

Nijmegen Breakage Syndrome is an autosomal recessive disorder characterized by developmental abnormalities, variable immune deficiency, and marked predisposition to malignancy. Cells established from NBS patients are sensitive to IR, exhibit chromosome fragility, and fail to activate cell cycle checkpoints in response to DNA damage (reviewed in Shiloh, 1997; van der Burgt et al., 1996; and Weemaes et al., 1994). With respect to these features, the mutations that result in NBS and AT have essentially identical phenotypic outcomes. This suggests that the NBS1 and ATM gene products effect the same or closely related functions in the cellular DNA damage response (Shiloh, 1997).

As shown above, deficiency in a member of the hMre11/hRad50 protein complex, p95, is the cause of NBS. The evidence for this is: 1) the p95 locus maps to 8q21.3 (FIG. 9), the region to which the NBS locus was previously localized (Matsuura et al., 1997; Saar et al., 1997); 2) the NBS1 and p95 cDNA sequences are identical; and 3) the p95 protein is absent from extracts of NBS cell lines that harbor NBS1 mutations (FIG. 11A). In light of the defects associated with NBS, these findings indicate that the hMre11/hRad50 protein complex is intimately involved in initiating the cellular DNA damage response.

The hMre11/HRad50 Protein Complex May Function as a Sensor of DNA Damage

The hMre11/hRad50 protein complex forms discrete nuclear foci (IRIF) following the induction of DSBs by ionizing radiation in normal cells (Example 1). In contrast, IRIF do not form in NBS cells (FIG. 12), suggesting that p95 is required for the relocalization of the hMre11/hRad50 protein complex to DSBs. This observation raises the possibility that p95 regulates the hMre11/hRad50 protein complex by transducing a signal originating from the site(s) of DNA damage. In normal cells, this signal leads to relocalization of the complex, whereas the signal is not transduced in NBS cells and so movement of the complex does not occur. A similar, though less severe defect was observed in SV-40 transformed AT cell lines (Example 1; Shiloh, 1997). These observations are consistent with the hypothesis that mutations in NBS and AT affect proximate functions in the DNA damage response.

However, the defect revealed by this aberrant IRIF response cannot account for the absence of DNA damage dependent cell cycle checkpoints and diminished p53 responses observed in NBS cells (Jongmans et al., 1997; Shiloh, 1997; Sullivan et al., 1997). These aspects of the NBS phenotype indicate that p95, and by extension, the hMre11/hRad50 protein complex, are an integral part of the signal that activates the cellular DNA damage response. In this regard, recent cytologic analyses of the hMre11/hRad50 protein complex in normal human cells are significant. DNA damage was induced in discrete subnuclear volumes, and DNA repair at those sites was monitored. hMre11 associated with DSBs within thirty minutes of their induction, and uniform distribution of the protein was restored upon subsequent DSB repair (Example 1). The observed behavior of hMre11 at the sites of DNA damage is consistent with the notion that the hMre11/hRad50 protein complex functions as a DNA damage sensor, and readily accounts for the DNA damage-dependent cell cycle checkpoint defects associated with NBS. The DNA repair functions of the hMre11/hRad50 protein complex are thus physically associated with the activation of other aspects of the cellular DNA damage response.

The hMre11/hRad50 Protein Complex in NBS Cells

The physical association of hMre11 and hRad50 is unaffected by the absence of p95 (FIG. 10B). Similarly, the association of ScMre11 and ScRad50 does not appear to depend upon ScXrs2 (Johzuka and Ogawa, 1995; Ogawa et al., 1995). However, cytologic analyses reveal that the disposition of hMre11 and hRad50 is abnormal in NBS cells. The uniform nuclear distribution typical of hMre11 and hRad50 in unirradiated normal cells is not seen in NBS cells (Example 1). Instead, the intranuclear abundance of hMre11/hRad50 appears to be reduced with a concomitant increase in the cytoplasmic level (FIGS. 13Q–T). Western blotting of fractionated NBS cell extracts shows that the protein is readily detectable in the nuclear fraction, though its level is somewhat diminished. This is expected, since in murine embryonic stem cells, muMre11 is required for viability (Xiao and Weaver, 1997). Whereas loss of p95 may decrease the intranuclear abundance of hMre11 and hRad50, the levels of these proteins must be sufficiently high to support cell viability.

Divergence of the hRad50/hMre11 Protein Complex hRad50 and hMre11 are human homologues of the *E. coli* proteins SbcC and SbcD (Sharples and Leach, 1995). SbcC and SbcD function in a protein complex, SbcCD, that possesses ATP-dependent double-stranded exonuclease activity and ATP independent single-strand endonuclease activity (Connelly et al., 1997; Connelly and Leach, 1996; and Gibson et al., 1992). Genetic evidence from *S. cerevisiae* suggests that the hMre11/Rad50/Xrs2 protein complex functions as a nuclease in that organism (Ivanov et al., 1996; Ivanov et al., 1994; and Tsubouchi and Ogawa, 1998). The biochemical activities of the hMre11/hRad50 protein complex have not been established, but the conservation of hMre11 and hRad50 suggests that they also encode nuclease activity.

It was found that p95 was not the human Xrs2 homologue. The replacement of Xrs2 by p95 in humans may indicate that the function(s) mediated by these proteins are not conserved. This seems an unlikely possibility in light of the conservation of Mre11 and Rad50, particularly since neither Xrs2 nor p95 appears to function outside of its respective complex (Example 1; Petrini et al., 1997). An alternative interpretation based on the NBS phenotype is that Xrs2 and p95 link the conserved activities of Mre11/Rad50 to the cellular DNA damage response in their respective organisms. In this sense, these divergent proteins could be considered functional analogues. The lack of similarity between p95 and Xrs2 would therefore reflect those features of the DNA damage response, and the roles of the hMre11/Rad50 nuclease within it, that are unique to each organism.

Phenotypic Similarity of *S. cerevisiae* and Human Mutants

The phenotypic features of *S. cerevisiae* mre11/rad50/xrs2 mutants are reminiscent of those observed in a number of human chromosomal instability syndromes such as NBS, AT, and Bloom syndrome (Bigbee et al., 1989; Bubley and Schnipper, 1987; Chaganti et al., 1974; Hojo et al., 1995; Langlois et al., 1989; Meyn, 1993). The chromosome fragility of NBS cells demonstrates that defects in the hMre11/hRad50 protein complex can result in similar phenotypic outcomes in mutant human cells.

Analogy of the *S. cerevisiae* and human phenotypes might also include DNA recombination defects, raising the possibility that immune dysfunction in NBS patients is attributable to DNA recombination defects. This interpretation is supported by the preponderance of chromosomal rearrangements involving chromosomes 7 and 14 in peripheral blood lymphocytes (reviewed in Weemaes et al., 1994). If the hMre11/hRad50 protein complex mediates single-strand DNA endonuclease activity similar to that of SbcCD (Connelly and Leach, 1996), the complex might be important for the resolution of hairpin intermediates generated in the V(D)J recombination process (Gellert, 1997).

In this regard, it is noteworthy that similar fragility of chromosomes 7 and 14 is seen in AT patients, yet the immune defects observed in that disease do not appear to result from defects in V(D)J recombination (Hsieh et al., 1993). Immunoglobulin heavy chain rearrangements in the NBS lymphoblastoid cell line, GM7078, have been analyzed by DNA sequencing and found to be normal (Petrini et al., 1994). However, quantitative analysis of V(D)J recombination in NBS cells is required to adequately address the role of the hMre11/hRad50 protein complex in this process. Lymphocyte-specific recombination is also required for immunoglobulin class switching (reviewed in Stavnezer, 1996), and it is conceivable that this process is also affected in NBS patients. Furthermore, DNA recombination in other contexts, such as in meiotic recombination, may also be affected by mutation of NBS1.

P95 Links Recombinational DNA Repair to Cancer Predisposition

Genomic instability is frequently observed in human cancer predisposition syndromes (Cleaver, 1989; German, 1983; Jackson, 1995; Kolodner, 1995; and Timme and Moses, 1988). Among such syndromes are congenitally acquired deficiencies in nucleotide excision repair and DNA mismatch repair. Since chromosomal rearrangements and changes in chromosome number are common features of malignant cells, errors in recombinational DNA repair are likely to play an important role in neoplasia (reviewed in Rabbitts, 1994; and Rowley, 1994). The implication of p95 and the hMre11/hRad50 protein complex in NBS constitutes an important link between congenital recombinational DNA repair deficiency and genomic instability associated with the predisposition to malignancy.

EXAMPLE 4

Bacterially Expressed Mre11

The hMre11 gene, nucleotides #1 to #1921 (SEQ ID NO:7) encoding SEQ ID NO:6, was cloned into an expression vector and expressed so as to generate an immunogen. Hybridoma lines were prepared that produced antibodies that recognized hMRE11. The resulting antiserum detects hMRE11, which is regulated in response to DNA damage, and may be relevant to tumorigenesis. Such antibodies may be of significant utility in clinical diagnosis as a predictive tool and for therapeutic applications.

REFERENCES

Ajimura, M., Leem, S. H., and Ogawa, H. Identification of new genes required for meiotic recombination in *Saccharomyces cerevisiae*. *Genetics*, 133:51–66 (1993).

Badie, C., Iliakis, G., Foray, N., Alsbeih, G., Cedervall, B., Chavaudra, N., Pantelias, G., Arlett, C. and Malaise, E. P. Induction and rejoining of DNA double-strand breaks and interphase chromosome breaks after exposure to X rays in one normal and two hypersensitive human fibroblast cell lines. *Radiat. Res.*, 144:26–35 (1995).

Badie, C., Iliakis, G., Foray, N., Alsbeih, G., Pantellias, G. E., Okayasu, R., Cheong, N., Russell, N. S., Begg, A. C., Arlett, C. F., and Malaise, E. P. Defective repair of DNA double-strand breaks and chromosome damage in fibroblasts from a radiosensitive leukemia patient. *Cancer Res.*, 55:1232–1234 (1995).

P. Baumann, F. Benson, and S. C. West, *Cell*, 87:757 (1996).

Bigbee, W. L., Langlois, R. G., Swift, M., and Jensen, R. H. Evidence for an elevated frequency of in vivo somatic cell mutations in ataxia telangiectasia. *Am. J. Hum. Genet.*, 44:402–408 (1989).

Blocher, D., Sigut, D., and Hannan, M. A. Fibroblasts from ataxia telangiectasia (AT) and AT heterozygotes show an enhanced level of residual DNA double-strand breaks after low dose-rate gamma-irradiation as assayed by pulsed field gel electrophoresis. *Int. J. Radiat. Biol.*, 60:791–802 (1991).

S. W. Botchway, D. L. Stevens, M. A. Hill, T. J. Jenner, and P. O'Neill. Induction and rejoining of DNA double-strand breaks in Chinese hamster V79-4 cells irradiated with characteristic aluminum K and copper L ultrasoft X rays. *Radiat. Res.*, 148:317–24 (1997).

Bubley, G. J. and Schnipper, L. E. Effects of Bloom's syndrome fibroblasts on genetic recombination and mutagenesis of herpes simplex virus type 1. *Somat. Cell Mol. Genet.*, 13, 111–7 (1987).

Chaganti, R. S. K., Schonberg, S., and German, J. A. A many fold increase in sister chromatid exchange in Bloom's syndrome lymphocytes. *Proc. Natl. Acad. Sci., USA*, 71:4508–4512 (1974).

Cleaver, J. E. DNA repair in man. *Birth Defects*, 25:61–82 (1989).

Connelly, J. C., de Leau, E. S., Okely, E. A., and Leach, D. R. Overexpression, purification, and characterization of the SbcCD protein from *Escherichia coli*. *J. Biol. Chem.*, 272:19819–26 (1997).

Connelly, J. C. and Leach, D. R. F. The sbcC and sbcD genes of *Escherichia coli* encode a nuclease involved in palindrome inviability and genetic recombination. *Genes to Cells*, 1:285–291 (1996).

Cornforth, M. N. and Bedford, J. S. X-ray-induced breakage and rejoining of human interphase chromosomes. *Science*, 222:1141–1143 (1983).

Cornforth, M. N. and Bedford, J. S. On the nature of a defect in cells from individuals with ataxia-telangiectasia. *Science*, 227:1589–1591. (1985).

R. Cox, J. Thacker, and D. T. Goodhead, Inactivation and mutation of cultured mammalian cells by aluminum characteristic ultrasoft X-rays. II Dose-responses of Chinese hamster and human diploid cells to aluminum X-rays and radiations of different LET. *Int. J. Radiat. Biol.,* 31:561–76 (1977).

Dolganov, G. M., Maser, R. S., Novikov, A., Tosto, L., Chong, S., Bressan, D. A., and petrini, J. H. H. Human Rad50 is physically associated with hMre11: identification of a conserved multiprotein complex implicated in recombinational DNA repair. *Mol Cell. Biol.,* 16:4832–4841(1996).

Durfee, T., Becherer, K., Chen, P.-L., Yeh, S.-H., Yang, Y., Kilbum, A. E., Lee, W. H., and Elledge, S. J. The retinoblastoma protein associates with the protein phosphatase type 1 catalytic subunit. *Genes &Dev.,* 7:555–569 (1993).

Ellis, N. A. DNA helicases in inherited human disorders. *Curr. Opin. Genet. Dev.,* 7:354–63 (1997).

Eng, J., McCormack, A. L., and Yates, J. R. III. An approach to correlate MS/MS data to amino acid sequences in protein database. *J. Am. Soc. Mass Spectrom.,* 5:976–989 (1994).

Flygare, J., Benson, F., and Hellgren, D. Expression of the human RAD51 gene during the cell cycle in primary human peripheral blood lymphocytes. *Biochim. Biophys. Acta,* 1312:231–236 (1996).

Ford, M. D., Martin, L., and Lavin, M. F. The effects of ionizing radiation on cell cycle progression in ataxia telangiectasia. *Mutat. Res.,* 125:115–122 (1984).

Fukuchi, K.-I., Martin, G. M., and Monnat, R. J. Mutator phenotype of Werner syndrome is characterized by extensive deletions. *Proc, Natl. Acad., Sci., USA,* 86:5893–5897 (1989).

Game, J. C. DNA double strand breaks and the RAD50–RAD57 genes in *Saccharomyces.* Cancer Biol., 4:73–83 (1993).

Gatlin, T., Gleeman, G., Hays, L. G., and Yates, J. R. III. Protein identification at the low femtomole level from silver stained gels using a new fritless electrospray interface for microLC/microESI/MS/MS. *Anal. Biochem.* (1998). Submitted.

Gatti, R. A., Boder, E., Vinters, H. V., Sparkes, R. S., Norman, A., and Lange, K. Ataxia-telangiectasia: an interdisciplinary approach to pathogenesis. *Medicine,* 70:99–117 (1991).

Gellert, M. Recent advances in understanding V(D)J recombination. *Adv. Immunol.,* 64:39–64 (1997).

German, J. Patterns of neoplasia associated with the chromosome-breakage syndromes. *In Chromosome Mutation &Neoplasia,* J. German, ed. (New York: Alan R. Liss), pp. 11–21.

Gibson, F. P., Leach, D. R. F., and Lloyd, R. G. Identification of sbcD mutations as cosuppressors of recBC that allow propagation of DNA palindromes in *Escherichia coli* K-12. *J. Bacteriol.,* 174:1222–1228 (1992).

Goodhead, D. T., J. Thacker, and R. Cox. Effectiveness of 0.3 kcV carbon ultrasoft X-rays for the inactivation and mutation of cultured mammalian cells. 1 *Int. J. Radiat., Biol,* 36:101–14 (1979).

Goodhead, D. T., J. Thacker, and R. Cox. Weiss Lecture. Effects of radiations of different qualities on cells: molecular mechanisms of damage and repair. *Int. J. Radiat. Biol.,* 63:543–56 (1993).

Gupta, R. C., L. R. Bazemore, E. I. Golub, and C. M. Radding. Activities of human recombination protein Rad51 *Proc Natl. Acad. Sci. U.S.A.,* 94:463–68 (1997).

Haaf, T., Golub, E. I., Reddy, G., Radding, C. M., and Ward, D. C. Nuclear foci of mammalian Rad51 recombination protein in somatic cells after DNA damage and its local-ization in synaptonemal complexes. *Proc. Natl. Acad. Sci. U.S.A.,* 92:2298–2302 (1995).

Harlow, E., and Lane, D. Antibodies: A laboratory manual (Cold Spring Harbor: Cold Spring Harbor Publications) (1988).

Hoekstra, M. F. Responses to DNA damage and regulation of cell cycle checkpoints by the ATM protein kinase family. *Curr. Opin. Genet. Dev.,* 7:170–5 (1997).

Hojo, E. T., van Diemen, P. C., Darroudi, F., and Natarajan, A. T. Spontaneous chromosomal aberrations in Fanconi anaemia, ataxia telangiectasia fibroblast and Bloom's syndrome lymphoblastoid cell lines as detected by conventional cytogenetic analysis and fluorescence in situ hybridisation (FISH) technique. *Mut. Res.,* 334:59–69 (1995).

Hozak, P., Hassan, A. B., Jackson, D. A., and Cook, P. R. Visualization of replication factories attached to a nucleoskeleton. *Cell,* 73:361–373 (1993).

Hsieh, C.-L, Arlett, C. F., and Leiber, M. R. V(D)J recombination in ataxia telangiectasia, Bloom's syndrome, and a DNA ligase I-associated immunodeficiency disorder. *J. Biol. Chem.,* 268:20105–20109 (1993).

L. C. Huang, K. C. Clarkin, and G. M. Wahl. Sensitivity and selectivity of the DNA damage sensor responsible for activating p53-dependent G1 arrest. *Proc. Natl. Acad. Sci. U.S.A.,* 93:4827–32 (1996).

Ivanov, E. L., Sugawara, N., Fishman-Lobell, J., and Haber, J. E. Genetic requirements for the single-strand annealing pathway of double-strand break repair in *Saccharomyces cerevisiae. Genetics,* 142:693–704 (1996).

Ivanov, E. L., Sugawara, N., White, C. I., Fabre, F., and Haber, J. E. Mutations in XRS2 and RAD50 delay but do not prevent mating-type switching in *Saccharomyces cerevisiae. Mol. Cell. Biol.,* 14:3414–25 (1994).

Jackson, S. P. DNA damage detection by DNA dependent protein kinase and related enzymes. *Cancer Surv.,* 28:261–279 (1996).

Jackson, S. P. and Jeggo, P. A. DNA double-strand break repair and V(D)J recombination: involvement of DNA-PK. *Trends Biochem. Sci.,* 20:412–415 (1995).

Jung, M., Kondratyev, A., Lee, S. A., Dimichev, A., and Dritschilo, A. ATM gene product phosphorylates 1κB-α. *Cancer Res.,* 57:24–27 (1997).

Jackson, S. P. Cancer predisposition. Ataxia-telangiectasia at the crossroads. *Curr. Biol.,* 5:1210–1212 (1995).

James, P., Halladay, J., and Craig, E. A. Genomic libraries and a host strain designed for highly efficient two-hybrid selection in yeast. *Genetics,* 144:1425–36 (1996).

Jayakumar, A., Huang, W. Y., Raetz, B., Chirala, S. S., and Wakil, S. J. Cloning and expression of the multifunctional human fatty acid synthase and its subdomains in *Escherichia coli. Proc. Natl. Acad. Sci. USA,* 93:14509–14 (1996).

Jeggo, P., G. E. Taccioli, and S. P. Jackson. Menage a trois: double strand break repair, V(D)J recombinantion and DNA-PK. *Bioessays,* 17:949–57 (1995).

Johzuka, K., and Ogawa, H. Interaction of Mre11 and Rad50: Two proteins required for DNA repair and meiosis-specific double-strand break formation in *Saccharomyces cerevisiae. Genetics,* 139:1521–1532 (1995).

Jongmans, W., Vuillaume, M., Chrzanowska, K., Smeets, D., Sperling, K., and Hall, J. Nijmegen breakage syndrome cells fail to induce the p53-mediated DNA damage response following exposure to ionizing radiation. *Mol. Cell. Biol.,* 17:5016–22 (1997).

Kanaar, R. and J. H. J. Hoeijmakers. Recombination and joining: different menas to the same ends. *Genes &Function,* 1:165–174 (1997).

Keegan, K. S., Holtzman, D. A., Plug, A. W., Christenson, E. R., Brainerd, E. E., Flaggs, G., Bentley, N. J., Taylor, E. M., Meyn, M. S., Moss, S. B., Carr, A. M., Ashley, T., and Hoekstra, M. F. The Atr and Atm protein kinases associate with different sites along meiotically pairing chromosomes. *Genes Dev.,* 10:2423–2437 (1996).

Kodym, R. and E. Hurth. Determination of rediation-induced DNA strand breaks in individual cells by non-radioactive labelling of 3'OH ends. *Int. J. Radiat. Biol.,* 68:133–139 (1995).

Kolodner, R. D. Mismatch repair: mechanisms and relationship to cancer susceptibility. *Trends Biochem. Sci.,* 20:397–401 (1995).

Langlois, R. G., Bigbee, W. L., Jensen, R. H., and German, J. Evidence for increased in vivo mutation & somatic recombination in Bloom's syndrome. *Proc. Natl. Acad. Sci. USA,* 86:670–674 (1989).

Leach, D. R. Long DNA palindromes, cruciform structures, genetic instability and secondary structure repair. *Bioessays,* 16: 893–900 (1994).

Li, X. and Z. Darzynkiewicz. Labelling DNA strand breaks with BrdUTP. Detection of apopotosis and cell proliferation. *Cell Prolif.,* 28:571–79 (1995).

Link, A. J., Hays, L. G., Carmack, E. B., and Yates, J. R. III. Identifying the major proteome components of *Haemophilus influenzae* type-strain NCTC 8143. *Electrophoresis,* 18:1314–34 (1997).

Lobrich, M., Rydberg, B., and Cooper, P. K. Repair of x-ray induced DNA double strand breaks in specific Not I restriction fragments in human fibroblasts: joining of correct and incorrect ends. *Proc. Natl. Acad. Sci. U.S.A.,* 92:12050–12054 (1995).

MacKay, J. F., D. W. Pearson, B. E. Nelms, P. M. DeLuca, M. N. Gould and M. G. Lagally. A double mirror W/C multilayer monochromator for radiation biology applications. *Med. Phys.,* 1998.

Maser, R. S., Monsen, K. J., Nelms, B. E., and Petrini, J. H. J. hMre11 and hRad50 nuclear foci are induced during the normal cellular response to DNA double strand breaks. *Mol. Cell. Biol.,* 17:6087–6097 (1997).

Matsuura, S., Weemaes, C., Smeets, D., Takami, H., Kondo, N., Sakamoto, S., Yano, N., Nakamura, A., Tauchi, H., Endo, S., Oshimura, M., and Komatsu, K. Genetic mapping using microcell-mediated chromosome transfer suggests a locus for Nijmegen breakage syndrome at chromosome 8q21–24. *Am. J. Hum. Genet.* 60:1487–94 (1997).

Meyn, M. S. Ataxia-telangiectasia and cellular responses to DNA damage. *Cancer Res.,* 55:5991–6001 (1995).

Meyn, M. S. High spontaneous rates of intrachromosomal recombination in ataxia-telangiectasia. *Science,* 260:1327–1330 (1993).

Murnane, J. P. Cell cycle regulation in response to DNA damage in mammalian cells: A historical perspective. *Cancer Met. Rev.,* 14: 17–29 (1995).

Nelms, B. E., Mackie, T. R., MacKay, J. F., Hill, C. K., DeLuca, P. M., Lindstrom, M. J., Deasy, J. and M. N. Gould. A comparison of cytotoxicity following whole versus partial cell irradiation with syncotron-produced ultrasoft X rays. *Radiat. Res.,* 1998.

Nelson, W. G. and M. B. Kastan. DNA strans breaks: the DNA template alterations hat trigger p53-dependent DNA damage response pathways. *Mol. Cell. Biol.,* 14:1815 (1994).

Nevaldine, B., Longo, J. A., King, G. A., Vilenchik, M., Sagerman, R. H., and Hahn, P. J. Induction and repair of DNA double-strand breaks. *Radiat. Res.,* 133:370–374 (1993).

Nishida, C., Reinhard, P., and Linn, S. DNA repair synthesis in human fibroblasts requires DNA polymerase delta. *J. Biol. Chem.,* 263:501–10 (1988).

Ogawa, H., Johzuka, K., Nakagawa, T., Leem, S., and Hagihara, A. Functions of the yeast meiotic recombination genes, MRE11 and MRE2. *Adv. Biophys.,* 31:67–76 (1995).

Olive, P. L., Wlodek, D., and Banath, J. P. DNA double-strand breaks measured in individual cells subjected to gel electrophoresis. *Cancer Res.,* 51:4671–4676 (1991).

Pandita, T. K., and Hittelman, W. N. Initial chromosome damage but not DNA damage is greater in ataxia telangiectasia cells. *Radiat. Res.,* 130:94–103 (1992).

Park, M. S., Knauf, J. A., Pendergrass, S. H., Coulon, C. H., Strniste, G. F., Marrone, B. L., and MacInnes, M. A. Ultraviolet-induced movement of the human DNA repair protein, *Xeroderma pigmentosum* type G, in the nucleus. *Proc. Natl. Acad. Sci. U.S.A.,* 93:8368–8373 (1996).

Perez-Vera, P., Gonzalez-del Angel, A., Molina, B., Gomez, L., Frias, S., Gatti, R. A., and Carnevale, A. Chromosome instability with bleomycin and X-ray hypersensitivity in a boy with Nijmegen breakage syndrome. *Am. J. Med. Genet.,* 70:24–7 (1997).

Petrini, J. H., Bressan, D. A., and Yao, M. S. The RAD52 epistasis group in mammalian double strand break repair. *Semin. Immunol.,* 2:181–8 (1997).

Petrini, J. H. J., Donovan, J. W., DiMare, C., and Weaver, D. T. Normal V(D)J coding junction formation in DNA ligase I deficiency syndromes. *J. Immunol.,* 152:176–183 (1994).

Petrini, J. H. J., Walsh, M. E., Di Mare, C., Korenberg, J. R., Chen, X.-N, and Weaver, D. T. Isolation and Characterization of the Human MRE11 homologue. *Genomics,* 29:80–86 (1995).

Rabbitts, T. H. Chromosomal translocations in human cancer. *Nature,* 372:143–9 (1994).

Rowley, J. D. Chromosome translocations: dangerous liaisons. *Leukemia,* S1–6 (1994).

Rowley, J. D., Diaz, M. O., Espinosa, R., Patel, Y. D., van Melle, E., Ziemin, S., Taillon-Miller, P., Lichter, P., Evans, G. A., Kersey, J. D., Ward, D. C., Domer, P. H., and Le Beau, M. M. Mapping chromosome band 11q23 in human acute leukemia with biotinylated probes: Identification of 11q23 translocation break points with a yeast artificial chromosome. *Proc. Natl. Acad. Sci. USA,* 81:9358–9362 (1990).

Saar, K., Chrzanowska, K. H., Stumm, M., Jung, M., Nurnberg, G., Wienker, T. F., Seemanova, E., Wegner, R. D., Reis, A., and Sperling, K. The gene for the ataxia-telangiectasia variant, Nijmegen breakage syndrome, maps to a 1-cM interval on chromosome 8q21. *Am. J. Hum. Genet.,* 60:605–10 (1997).

Savitsky, K., Bar-Shira, A., Gilad, S., Rotman, G., Ziv, Y., Vanagaite, L., Tagle, D. A., Smith S., Uziel, T., Sfez, S., Ashkenazi, M., Pecker, I, Frydman, M., Harnik, R., Patanjall, S. R., Simmons, A., Clines, G. A., Sartiel, A., Gatti, R. A., Chessa, L., Sanal, O., Lavin, M. F., Jaspers, N. G. J., Taylor, A. M. R., Arlett, C. F., Miki, T., Weissman, S. M., Lovett, M., Collins, F. S., and Shiloh, Y. A single ataxia telangiectasia gene with a product similar to PI-3 kinase. *Science,* 268:1749–1753 (1995).

Scully, R., Chen, J., Plug, A., Xiao, Y., Weaver, D., Feunteun, J., Ashley, T., and Livingston, D. M. Association of BRCA1 with Rad51 in mitotic and meiotic cells. *Cell*, 88:265–75 (1997).

Scully, R., Chen, J., Ochs, R. L., Keegan, K., Hoestra, M., Feunteun, J. and D. M. Livinston. Dynamic changes in BRAC1 subnuclear location and phosphorylation state are initiated by DNA damage. *Cell*, 90:425–35 (1997).

Sharples, G. J. and Leach, D. R. Structural and functional similarities between the SbcCD proteins of *Escherichia coli* and the RAD50 and MRE11 (RAD32) recombination and repair proteins of yeast. *Mol. Microbiol.*, 17:1215–1217 (1995).

Shevchenko, A., Wilm, M., Vorm, O., and Mann, M. Mass spectrometric sequencing of proteins from silver-stained polyacrylamide gels. *Anal. Chem.*, 68:850–858 (1996).

Shiloh, Y. Ataxia-telangiectasia and the Nijmegen breakage syndrome: related disorders but genes apart. *Annu. Rev. Genet.*, 31:635–62 (1997).

Singer, R. H. and M. R. Gree. Compartmentalization of eukaryotic gene expression: causes and effects. *Cell*, 91:291–4 (1997).

Stavnezer, J. Antibody class switching. *Adv. Immunol.*, 61:79–146 (1996).

Strouboulis, J. and A. P. Wolffe. Functional compartmentalization of the nucleus. *J. Cell Sci.*, 109, 1991–2000 (1996).

Stumm, M., Sperling, K., and Wegner, R. D. Noncomplementation of radiation-induced chromosome aberrations in ataxia-telangiectasia/ataxia-telangiectasia-variant heterodikaryons [letter]. *Am. J. Hum., Genet.*, 60:1246–51 (1997).

Sugawara, N. and J. E. Habe. Characterization of double-strand break-induced recombination: homology requirements and singel-stranded DNA formation. *Mol. Cell. Biol.*, 12:563–75 (1992).

Sullivan, K. E., Veksler, E., Lederman, H., and Lees-Miller, S. P. Cell cycle checkpoints and DNA repair in Nijmegen breakage syndrome. *Clin. Immunol. Immunopathol*, 82:43–8 (1997).

Sung, P. and D. L. Robberson. DNA strand exchange mediated by RAD51-ssDNA nucleoprotein filament with polarity opposite to that of RecA. *Cell*, 82:453–61 (1995).

Szostak, J. W., T. L. Orr-Weaver, R. J. Rothstein, and F. W. Stahl. The double-strand break repair model for recombination. *Cell*, 33:25–35 (1983).

Taalman, R. D., Jaspers, N. G., Scheres, J. M., de Wit, J., and Hustinx, T. W. Hypersensitivity to ionizing radiation, in vitro, in a new chromosomal breakage disorder, the Nijmegen Breakage Syndrome. *Mut. Res.*, 112:23–32 (1983).

Timme, T. L., and Moses, R. E. Diseases with DNA damage-processing defects. *Amer. J. Med. Sci.*, 295:40–48 (1988).

Tsubouchi, H., and Ogawa, H. A novel mre11 mutation impairs processing of double-strand breaks of DNA during both mitosis and meiosis. *Mol, Cell. Biol.*, 18:260–8 (1998).

van der Burgt, I., Chrzanowska, K. H., Smeets, D., and Weemaes, C. Nijmegen breakage syndrome. *J. Med. Genet.*, 33:153–6 (1996).

Virsik-Peuckert, R. P. in *Radiation-Induced Chromosome Damage in Man*, I. Ishihara and M. S. Sasaki, eds. (Alan Liss, Inc., New York, 1983), vol. 4, pp. 51–69.

Weaver, D. T. What to do at an end: DNA double-strand break repair. *Trends Genet.*, 11:388–392 (1995).

Weemaes, C. M., Hustinx, T. W., Scheres, J. M., van, M. P., Bakkeren, J. A., and Taalman, R. D. A new chromosomal instability disorder: the Nijmegen breakage syndrome. *Acta. Paediatr. Scand.*, 70:557–64 (1981).

Weemaes, C. M., Smeets, D. F., and van der Burgt, C. J. Nijmegen Breakage syndrome: a progress report. *Int. J. Radiat. Biol*, 66:S185–8 (1994).

Xiao, Y., and Weaver, D. T. Conditional gene targeted deletion by Cre recombinase demonstrates the requirement for the double-strand break repair Mre11 protein in murine embryonic stem cells. *Nucleic Acids Res.*, 25:2985–91 (1997).

Yamamoto, A., Taki, T., Yagi, H., Habu, T., Yoshida, K., Yoshimura, Y., Yamamoto, K., Matsushiro, A., Nishimune, Y., and Morita, T. Cell cycle-dependent expression of the mouse Rad51 gene in proliferating cells. *Mol. Gen. Genet.*, 251:1–12 (1996).

Yates, J. R. III., Eng, J., and McCormack, A. L. Mining Genomes: Correlating tandem mass spectra of modified and unmodified peptides to nucleotide sequences. *Anal. Chem.*, 67:3203–3210 (1995).

Young, B. R. and Painter, R. B. Radioresistant DNA synthesis and human genetic diseases. *Hum, Genet.*, 82:113–7 (1989).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified nucleic acid molecule encoding a vertebrate DNA repair polypeptide having SEQ ID NO:2, wherein the polypeptide has a molecular weight of about 95000 Da as determined by SDS-PAGE.

2. The nucleic acid molecule of claim 1 which has SEQ ID NO:1.

3. An isolated and purified DNA molecule consisting of SEQ ID NO:1, or a DNA molecule which is fully complementary thereto.

4. An isolated nucleic ad molecule comprising a promoter operably linked to a nucleic acid segment encoding SEQ ID NO:2.

5. The nucleic acid molecule of claim 4 wherein the nucleic acid segment has SEQ ID NO:1.

6. An expression vector comprising a promoter operably linked to a nucleic acid segment which encodes a fusion polypeptide comprising at least a portion of a DNA repair polypeptide which binds an antibody specific for SEQ ID NO:2, wherein the portion of the DNA repair polypeptide includes residues 399 to 751 of SEQ ID NO:2.

7. An isolated and purified nucleic acid molecule encoding a vertebrate DNA repair polypeptide, wherein the polypeptide has a molecular weight of about 95000 Da as determined by SDS-PAGE, wherein the nucleic acid molecule has SEQ ID NO:1.

8. The nucleic acid molecule of claim 1, 3, 4, 6 or 7 which is labeled.

9. The nucleic acid molecule of claim 6 wherein the fusion polypeptide is a fusion of glutathione S-transferase and at least a portion of the DNA repair polypeptide.

10. The nucleic acid molecule of claim 6 wherein the fusion polypeptide is a fusion of a histidine tag and at least a portion of the DNA repair polypeptide.

11. The nucleic acid molecule of claim 1 wherein SEQ ID NO:2 is immunogenic, binds DNA, forms a complex with hMre11/hRad50, or has nuclease activity when associated with hMre11/hRad50.

* * * * *

UNITED STATES PATENT AND TRADEMARK OFFICE
CERTIFICATE OF CORRECTION

| | | |
|---|---|---|
| PATENT NO. | : 7,091,037 B1 | Page 1 of 2 |
| APPLICATION NO. | : 09/837602 | |
| DATED | : August 15, 2006 | |
| INVENTOR(S) | : Petrini et al. | |

It is certified that error appears in the above-identified patent and that said Letters Patent is hereby corrected as shown below:

Title page, in field (75), in "Inventors", in column 1, lines 2–3, before "Richard" delete "William Francis Morgan, Mill Valley, CA (US);".

Title page, in field (75), in "Inventors", in column 1, line 4–5, after "WI (US);" delete "James Patrick Carney, El Cerrito, CA (US)".

Title page, in field (56), under "Other Publications", in column 1, line 2, after "et al." insert -- , --.

Title page, in field (56), under "Other Publications", in column 1, line 2, after "Biology" insert -- , --.

Title page, in field (56), under "Other Publications", in column 1, line 3, delete "(Bowie et al." and insert -- Bowie et al., --, therefor.

Title page, in field (56), under "Other Publications", in column 2, line 1, delete "Saccharomyces" and insert -- saccharomyces --, therefor.

Title page, in field (56), under "Other Publications", in column 2, line 2, delete "Escherichia" and insert -- escherichia --, therefor.

Title page, in field (56), under "Other Publications", in column 2, line 4, delete "1991-197," and insert -- 191-197, --, therefor.

Title page, in field (56), under "Other Publications", in column 2, line 6, after "7" insert -- , --.

Title page, in field (56), under "Other Publications", in column 2, line 17, delete "characterizatio" and insert -- characterization --, therefor.

Title page, in field (56), under "Other Publications", in column 2, line 20, delete "Nex" and insert -- Next --, therefor.

Title page, in field (56), under "Other Publications", in column 2, line 22, delete "Targeted" and insert -- targeted --, therefor.

UNITED STATES PATENT AND TRADEMARK OFFICE
CERTIFICATE OF CORRECTION

PATENT NO. : 7,091,037 B1
APPLICATION NO. : 09/837602
DATED : August 15, 2006
INVENTOR(S) : Petrini et al.

It is certified that error appears in the above-identified patent and that said Letters Patent is hereby corrected as shown below:

Title page, in field (56), under "Other Publications", in column 2, line 25, delete "Nuclecid" and insert -- Nucleic --, therefor.

Title page, in field (56), under "Other Publications", in column 2, line 31, after "Syndrome" insert -- : --.

Title page, in field (56), under "Other Publications", in column 2, line 34, after "et al." insert -- , --.

Title page, in field (74), in "Attorney, Agent, or Firm", in column 2, line 1, delete "Schweggman" and insert -- Schwegman --, therefor.

Title page, in field (74), in "Attorney, Agent, or Firm", in column 2, line 2, after "Kluth" insert -- , --.

In column 79, line 46, in Claim 4, delete "ad" and insert -- acid --, therefor.

Signed and Sealed this

Sixth Day of February, 2007

JON W. DUDAS
*Director of the United States Patent and Trademark Office*